US 11,864,744 B2

(12) United States Patent
Clements et al.

(10) Patent No.: US 11,864,744 B2
(45) Date of Patent: Jan. 9, 2024

(54) DUAL MOVABLE BLADE BIOPSY TOOL WITH STYLET

(71) Applicant: Crux Medical Innovations, Inc., Issaquah, WA (US)

(72) Inventors: Robert M. Clements, Issaquah, WA (US); Andrew R. Face, Issaquah, WA (US)

(73) Assignee: CRUX MEDICAL INNOVATIONS, INC., Issaquah, WA (US)

( * ) Notice: Subject to any disclaimer, the term of this patent is extended or adjusted under 35 U.S.C. 154(b) by 188 days.

(21) Appl. No.: 17/348,269

(22) Filed: Jun. 15, 2021

(65) Prior Publication Data
US 2021/0307734 A1  Oct. 7, 2021

Related U.S. Application Data

(62) Division of application No. 15/727,362, filed on Oct. 6, 2017, now Pat. No. 11,076,841, which is a division
(Continued)

(51) Int. Cl.
*A61B 10/04* (2006.01)
*A61B 10/02* (2006.01)
(Continued)

(52) U.S. Cl.
CPC .......... *A61B 10/04* (2013.01); *A61B 10/0266* (2013.01); *A61B 10/0283* (2013.01);
(Continued)

(58) Field of Classification Search
CPC ...... A61B 10/04; A61B 10/02; A61B 10/0266
See application file for complete search history.

(56) References Cited

U.S. PATENT DOCUMENTS

| 2,493,979 A | 1/1950 | Rudolph |
| 4,640,296 A | 2/1987 | Schnepp-Pesch et al. |

(Continued)

FOREIGN PATENT DOCUMENTS

| EP | 1792574 A1 | 6/2007 |
| WO | 1995008291 A1 | 3/1995 |

(Continued)

OTHER PUBLICATIONS

International Application No. PCT/2010/058115, International Search Report and Written Opinion dated Feb. 18, 2011, 15 pages.
(Continued)

*Primary Examiner* — Marjan Fardanesh
(74) *Attorney, Agent, or Firm* — BROOKS KUSHMAN PC

(57) ABSTRACT

A biopsy device comprises a sheath equipped with a removable stylet. The sheath including a terminus with a distal chamber configured with a forward facing cutting edge comprising a plurality of movable blades. The plurality of movable blades including two counter rotating blades configured perpendicular or beveled relative to a long axis of the distal chamber, each counter rotating blade configured to pivot from a separate axis. The biopsy device further comprises a manipulation end controllable by a user to plunge the forward facing cutting edge at a sampling locus after removal of the removable stylet at a depth and to engage a cutting action by the plurality of movable blades at the depth selected to acquire at least one specimen storable in the distal chamber.

19 Claims, 46 Drawing Sheets

Related U.S. Application Data of application No. 12/954,584, filed on Nov. 24, 2010, now abandoned.

(60) Provisional application No. 61/264,628, filed on Nov. 25, 2009.

(51) Int. Cl.
*A61B 10/06* (2006.01)
*A61B 10/00* (2006.01)
*A61B 90/00* (2016.01)

(52) U.S. Cl.
CPC ....... *A61B 10/06* (2013.01); *A61B 2010/0093* (2013.01); *A61B 2010/0225* (2013.01); *A61B 2090/033* (2016.02); *A61B 2090/062* (2016.02)

(56) References Cited

U.S. PATENT DOCUMENTS

| | | | |
|---|---|---|---|
| 4,682,606 | A | 7/1987 | DeCaprio |
| 5,171,255 | A | 12/1992 | Rydell |
| 5,195,533 | A | 3/1993 | Chin et al. |
| 5,217,458 | A | 6/1993 | Parins |
| 5,542,432 | A | 8/1996 | Slater et al. |
| 5,562,102 | A | 10/1996 | Taylor |
| 5,573,008 | A | 11/1996 | Robinson et al. |
| 5,618,293 | A | 4/1997 | Sample et al. |
| 5,636,639 | A | 6/1997 | Turturro et al. |
| 5,638,827 | A | 6/1997 | Palmer et al. |
| 5,683,388 | A | 11/1997 | Slater |
| 5,746,216 | A | 5/1998 | Turturro et al. |
| 5,762,069 | A | 6/1998 | Kelleher et al. |
| 5,779,648 | A | 7/1998 | Banik et al. |
| 5,951,488 | A | 9/1999 | Slater et al. |
| 6,083,150 | A | 7/2000 | Aznoian et al. |
| 6,110,127 | A | 8/2000 | Suzuki |
| 6,142,957 | A | 11/2000 | Diamond et al. |
| 6,383,145 | B1 | 5/2002 | Worm et al. |
| 6,419,640 | B1 | 7/2002 | Taylor |
| 6,572,578 | B1 | 6/2003 | Blanchard |
| 7,278,971 | B2 | 10/2007 | Reydel |
| 8,052,659 | B2 | 11/2011 | Ravenscroft et al. |
| 8,097,012 | B2 | 1/2012 | Kagarise |
| 2002/0010483 | A1 | 1/2002 | Follmer et al. |
| 2002/0143270 | A1 | 10/2002 | Miller |
| 2002/0156395 | A1 | 10/2002 | Stephens et al. |
| 2003/0208209 | A1 | 11/2003 | Gambale et al. |
| 2005/0119652 | A1 | 6/2005 | Vetter et al. |
| 2005/0165329 | A1 | 7/2005 | Taylor et al. |
| 2005/0261604 | A1 | 11/2005 | Stephens et al. |
| 2005/0277829 | A1 | 12/2005 | Tsonton et al. |
| 2006/0084885 | A1 | 4/2006 | Reydel |
| 2006/0084886 | A1 | 4/2006 | Reydel |
| 2007/0055215 | A1 | 3/2007 | Tran et al. |
| 2007/0213631 | A1 | 9/2007 | Kondo et al. |
| 2008/0058672 | A1 | 3/2008 | Shabaz et al. |
| 2008/0132930 | A1 | 6/2008 | Lubock et al. |
| 2008/0154151 | A1 | 6/2008 | Ritchart et al. |
| 2008/0234698 | A1 | 9/2008 | Oostman et al. |
| 2008/0306406 | A1 | 12/2008 | Thompson et al. |
| 2008/0319341 | A1 | 12/2008 | Taylor et al. |
| 2009/0018467 | A1 | 1/2009 | Chiu et al. |
| 2009/0118641 | A1 | 5/2009 | Dam et al. |
| 2009/0137928 | A1 | 5/2009 | Quick et al. |
| 2009/0187118 | A1 | 7/2009 | Kim et al. |
| 2009/0204023 | A1 | 8/2009 | Goldenberg |
| 2009/0227893 | A1 | 9/2009 | Coonahan et al. |
| 2009/0228034 | A1 | 9/2009 | Sauer |
| 2009/0259223 | A1 | 10/2009 | Eggers et al. |

FOREIGN PATENT DOCUMENTS

| | | |
|---|---|---|
| WO | 1995008292 A1 | 3/1995 |
| WO | 2002032293 A2 | 4/2002 |

OTHER PUBLICATIONS

U.S. Appl. No. 12/954,584, Final Office Action dated Aug. 1, 2016, 11 pages.
U.S. Appl. No. 12/954,584, Final Office Action dated Nov. 24, 2014, 11 pages.
U.S. Appl. No. 12/954,584, Non-Final Office Action dated Apr. 7, 2017, 10 pages.
U.S. Appl. No. 12/954,584, Non-Final Office Action dated Oct. 9, 2015, 18 pages.
U.S. Appl. No. 12/954,584, Non-Final Office Action dated Jan. 16, 2014, 11 pages.
U.S. Appl. No. 15/727,362, Final Office Action dated Dec. 24, 2020, 95 pages.
U.S. Appl. No. 15/727,362, Notice of Allowance dated Mar. 16, 2021, 103 pages.
U.S. Appl. No. 15/727,362, Restriction Requirement dated Sep. 12, 2019, 5 pages.

1) Closed Position

2) Depth stop wires deployed (highlighted in black)

Stop wires travel down tubes (see detail drawing call out to Fig. 11A) toward ends and lock into position 3) Biopsy core advanced

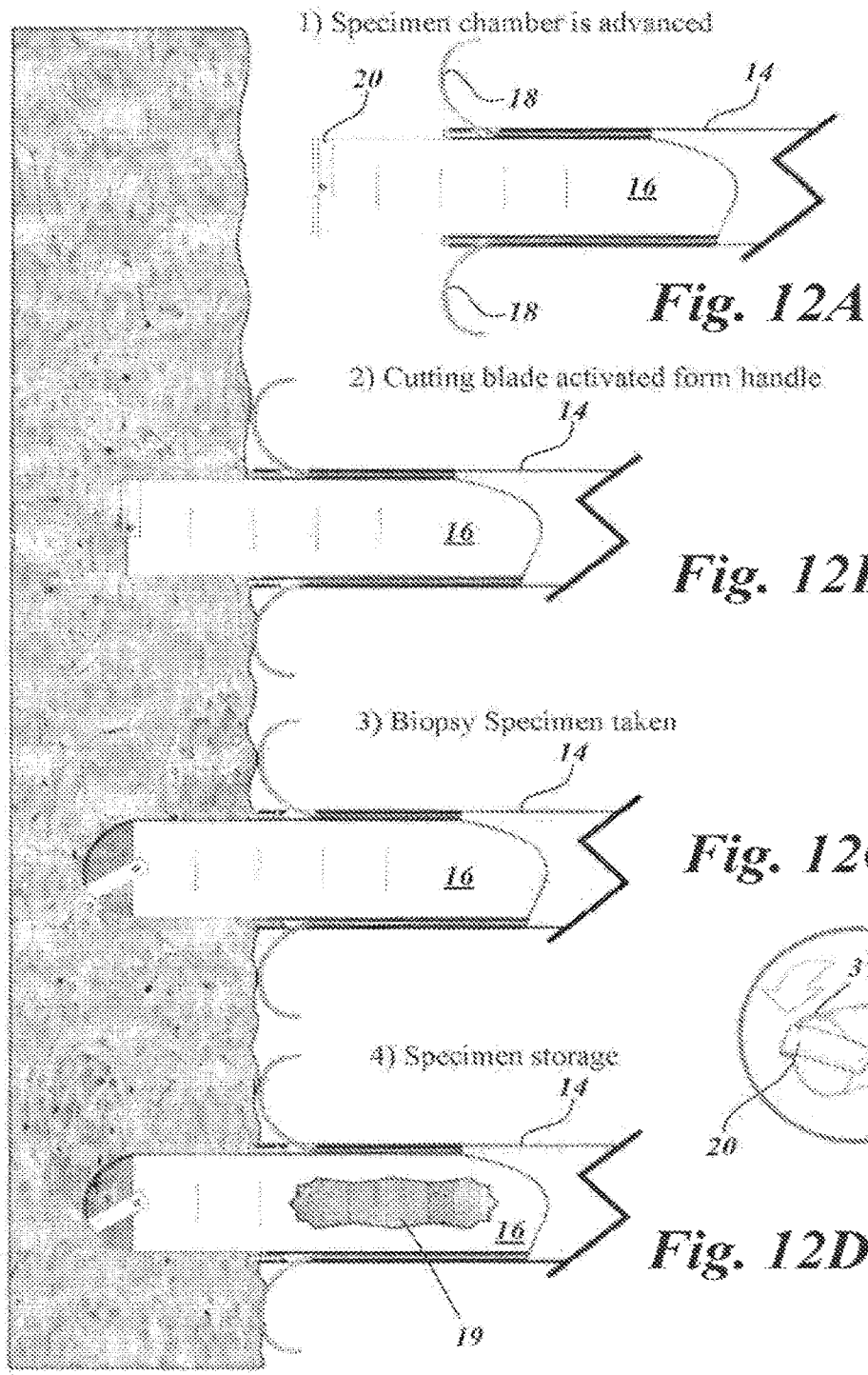

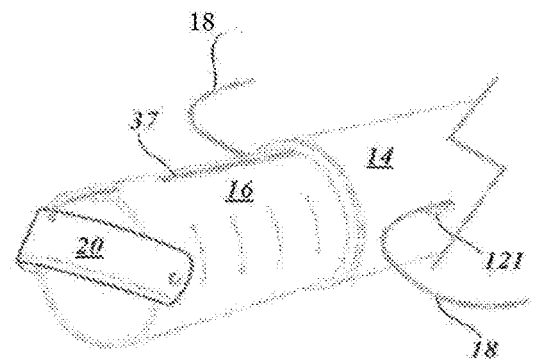 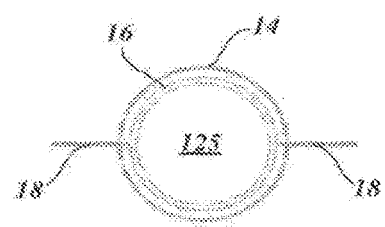
*Fig. 19A*
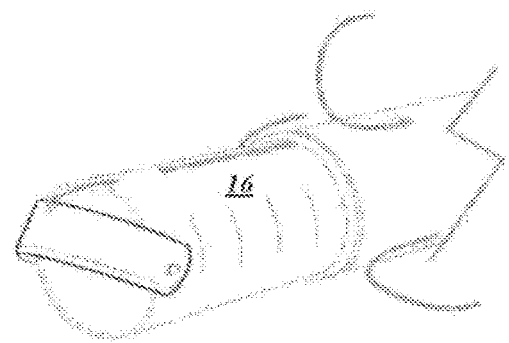 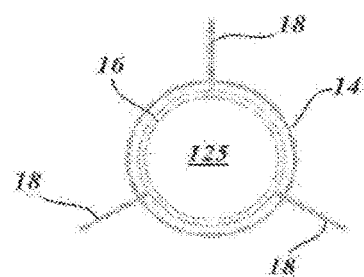
*Fig. 19B*
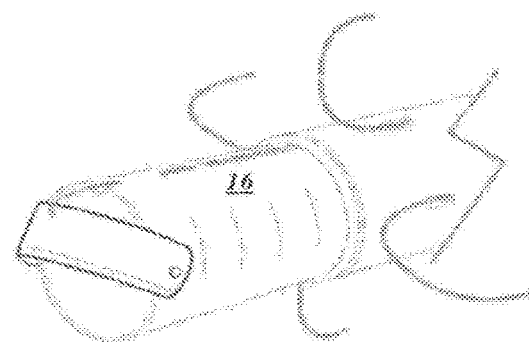 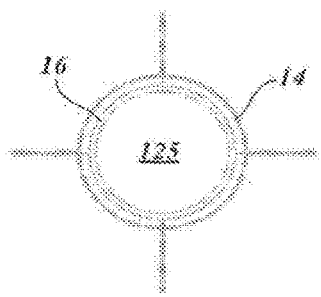
*Fig. 19C*
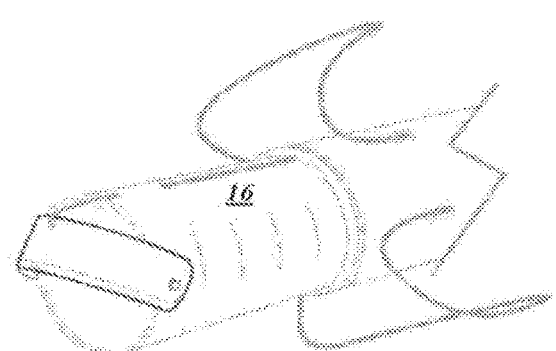 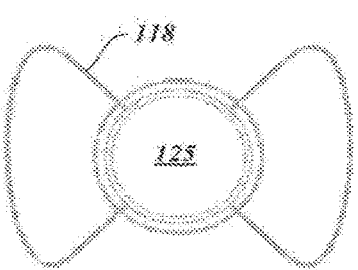
*Fig. 19D*

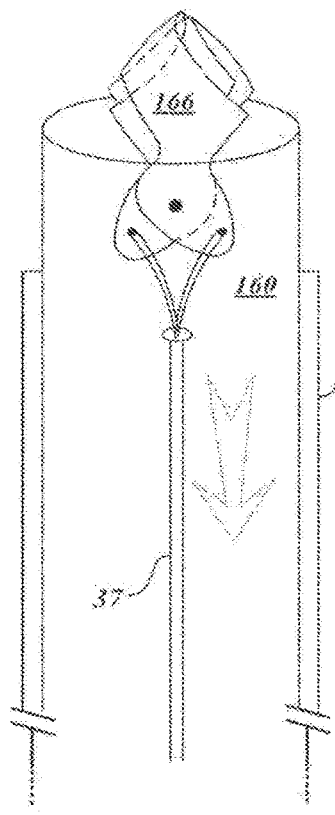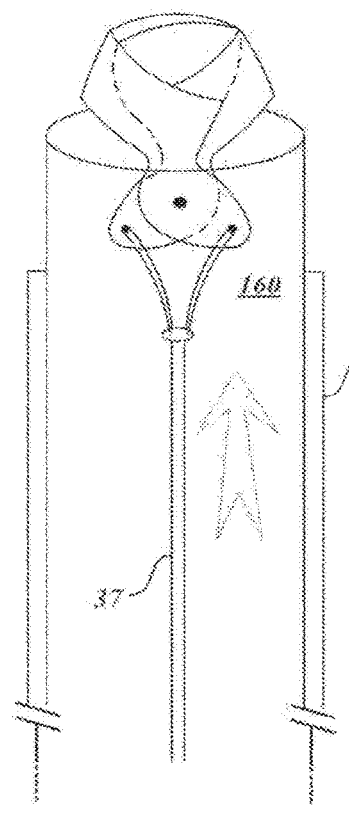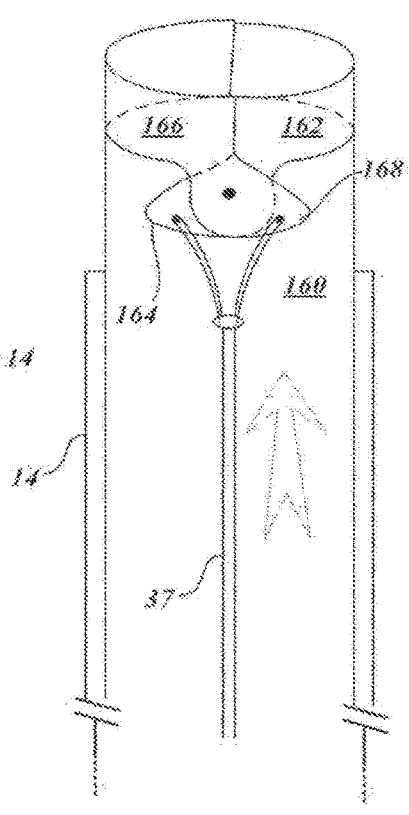
*Fig. 21B*  *Fig. 21C*  *Fig. 21D*

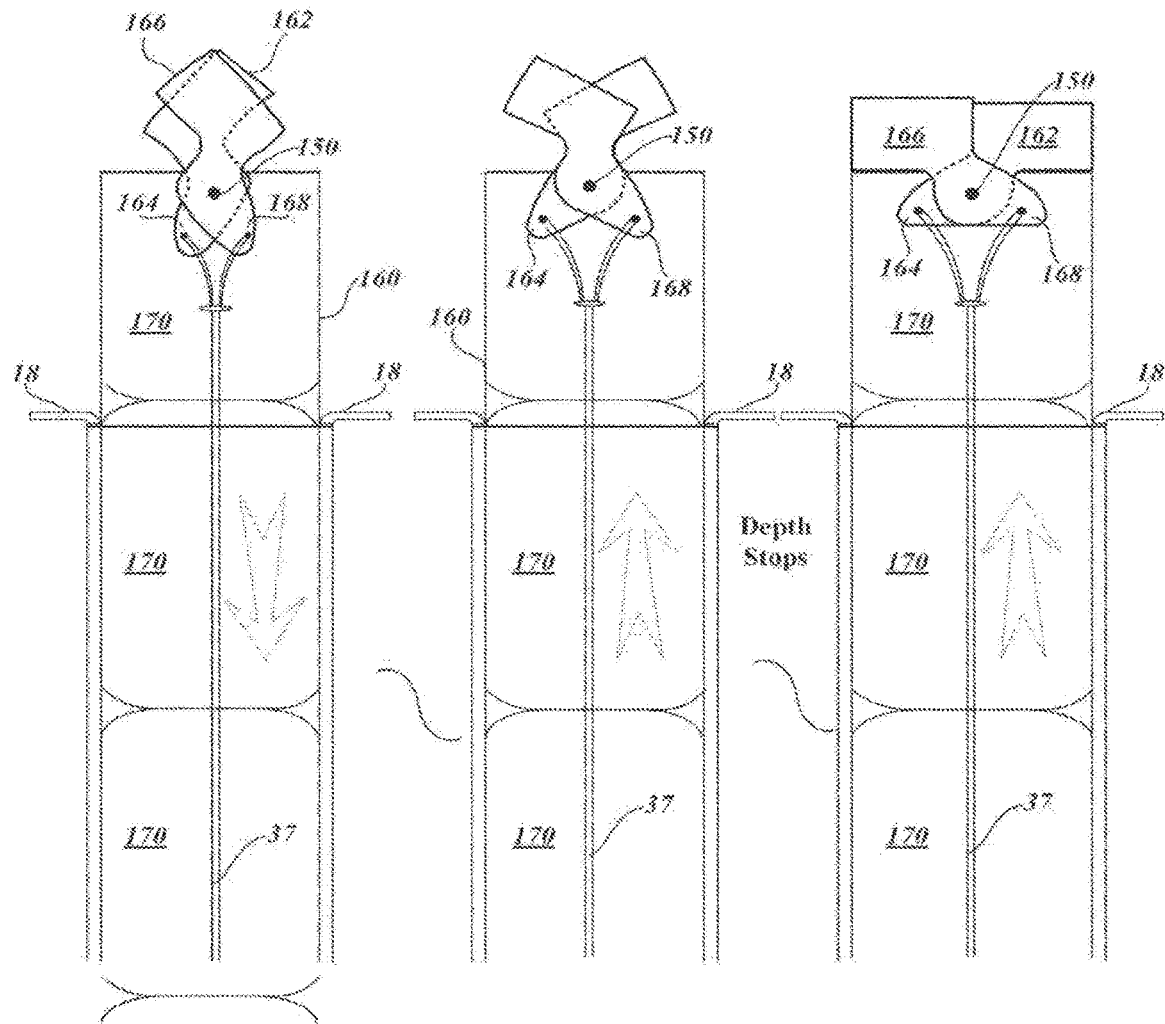
*Fig. 21E*  *Fig. 21F*  *Fig. 21G*

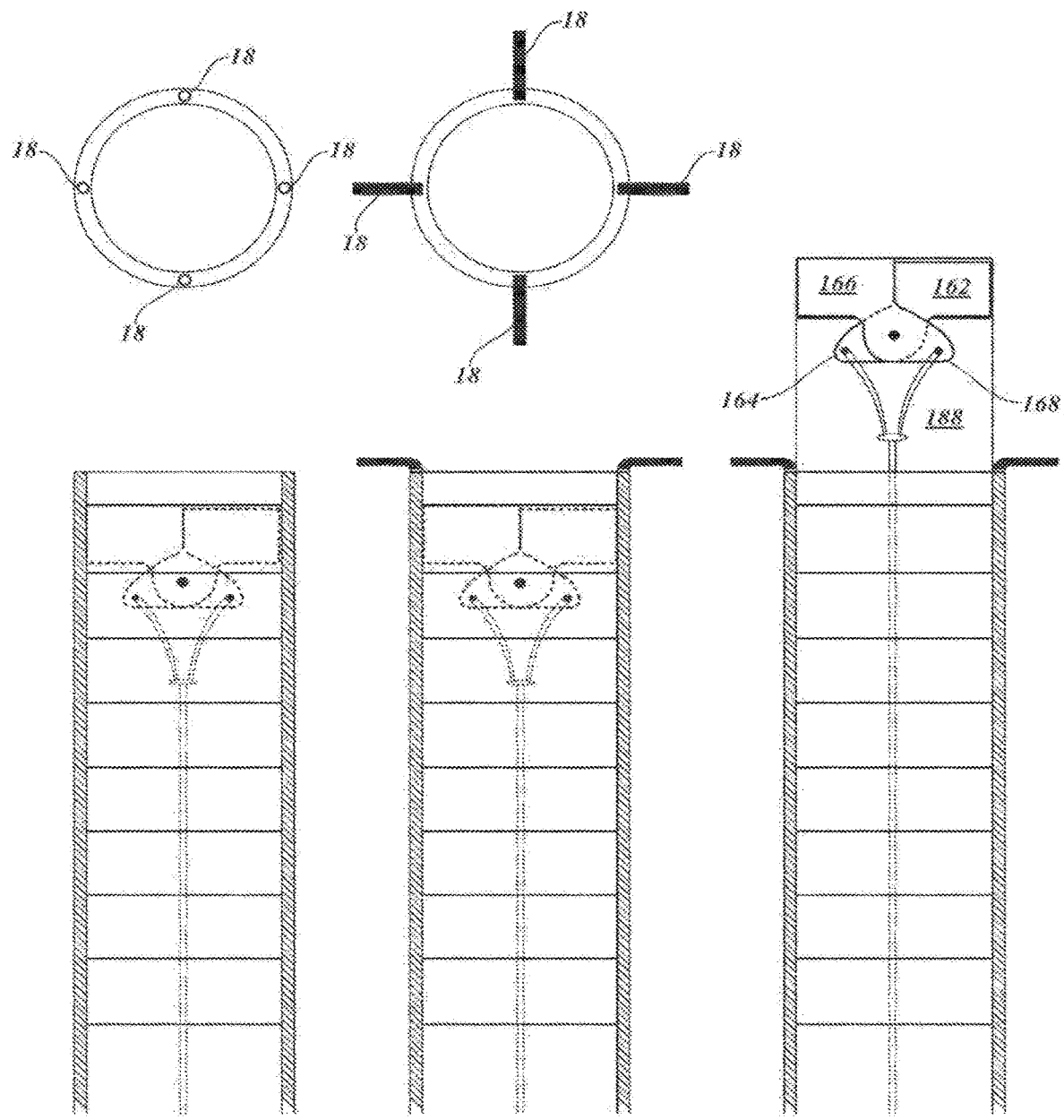
*Fig. 25A*  *Fig. 25B*  *Fig. 25C*

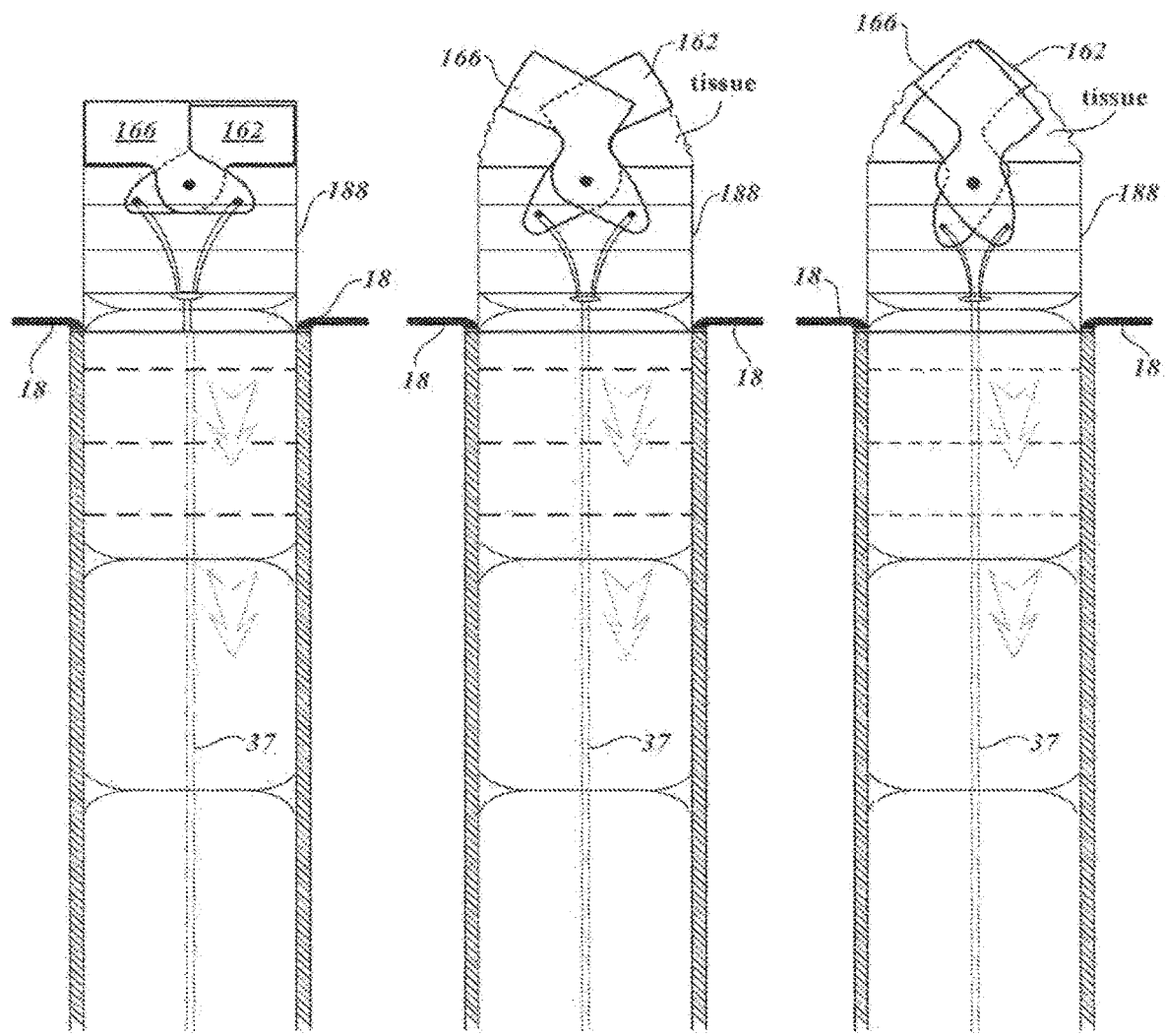
*Fig. 25D*   *Fig. 25E*   *Fig. 25F*

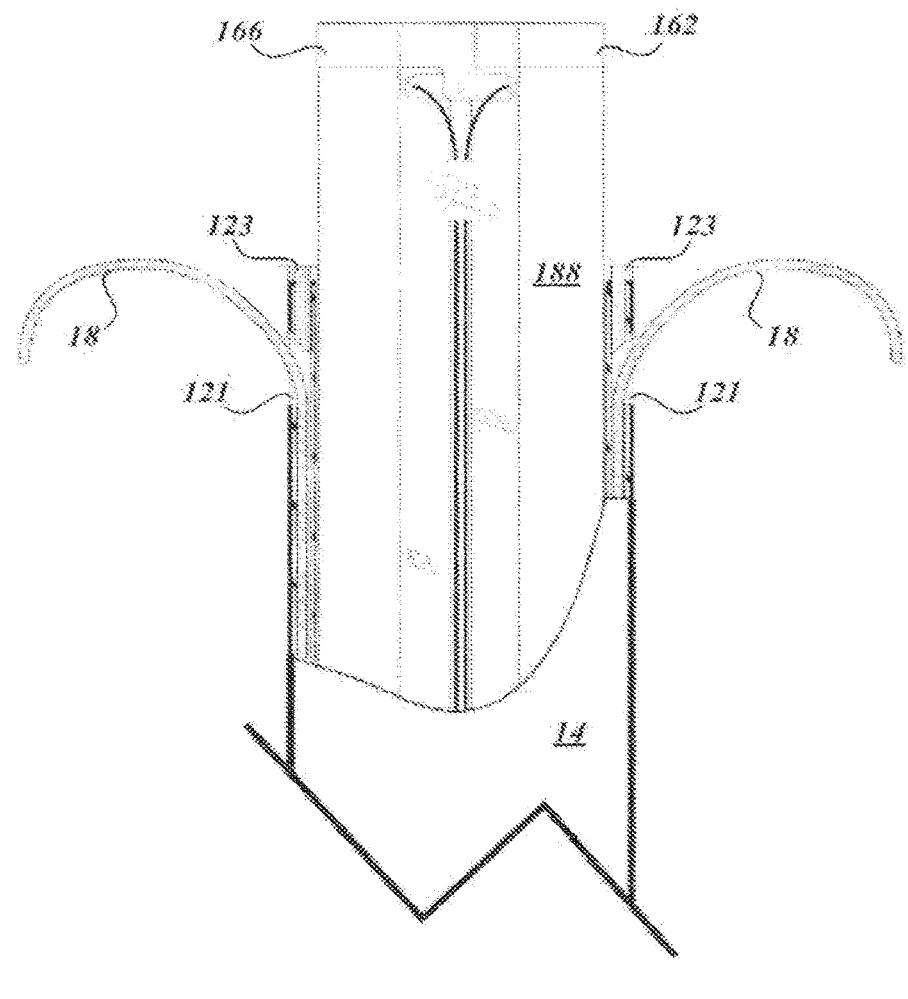
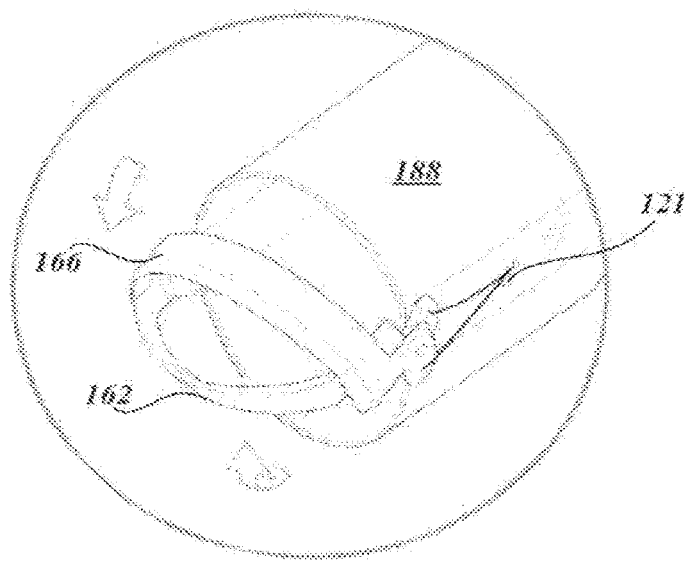
Fig. 33

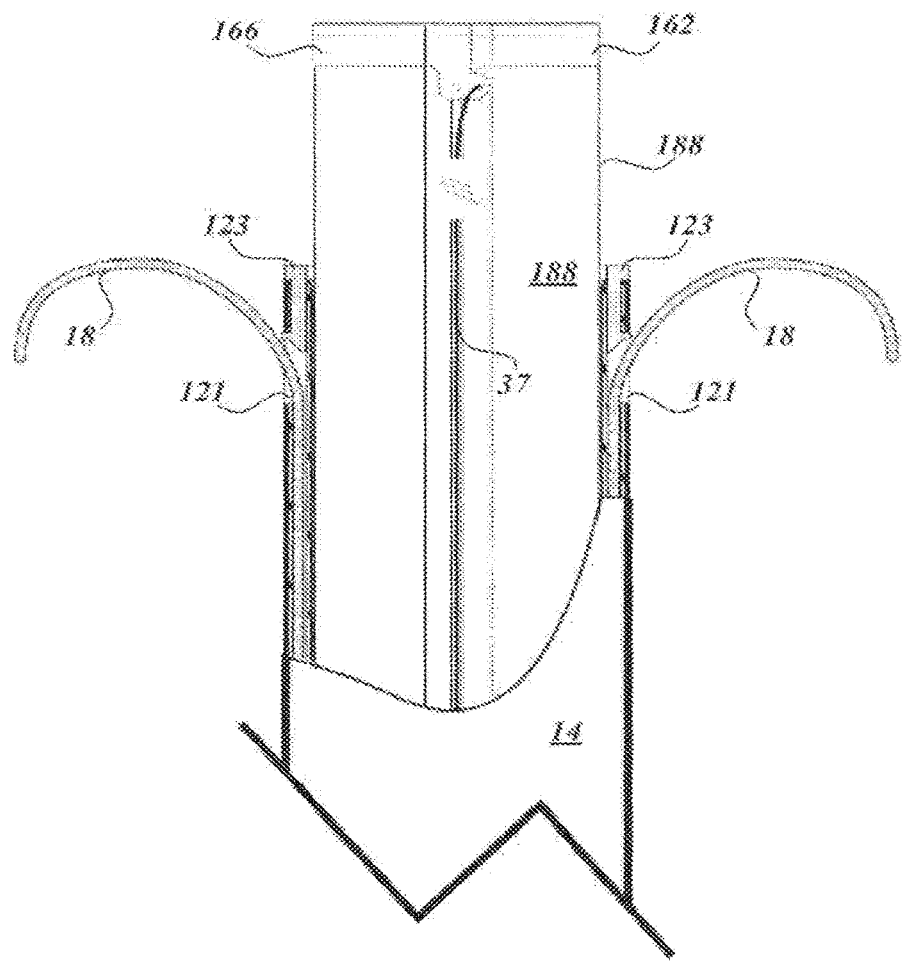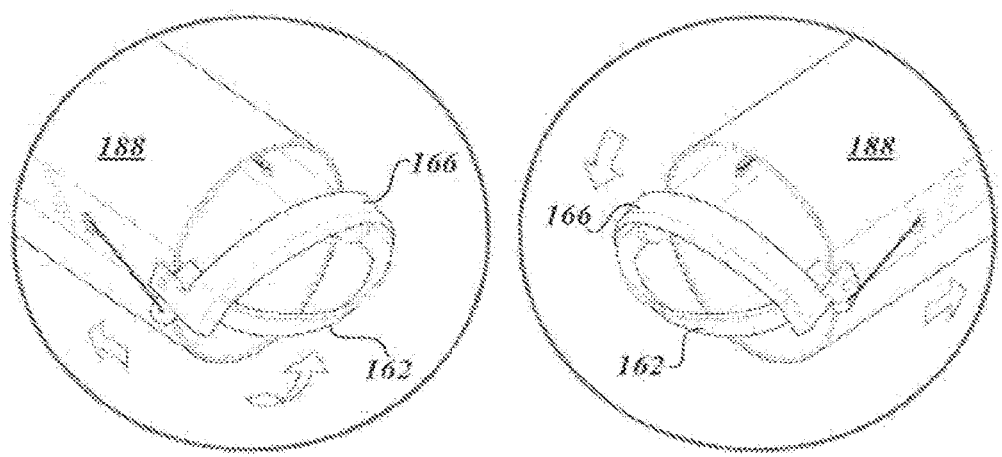
Fig. 34

DUAL MOVABLE BLADE BIOPSY TOOL WITH STYLET

CROSS REFERENCE TO RELATED PATENT APPLICATIONS

This patent application is a divisional application of U.S. patent application Ser. No. 15/727,362, filed on Oct. 6, 2017, now U.S. Pat. No. 11,076,841, which is a divisional application of U.S. patent application Ser. No. 12/954,584, filed on Nov. 24, 2010, which claims the benefit of priority to U.S. Provisional Patent Application Ser. No. 61/264,628 filed Nov. 25, 2009, which are hereby incorporated by reference in their entirety.

FIELD OF THE INVENTION

An embodiment of the invention relates generally to biopsy devices used in endoscopic and other tissue sampling procedures.

BACKGROUND

The traditional biopsy forceps used today typically gather just one biopsy specimen at a time. The forceps must be removed from the scope each time to retrieve the single specimen. This is a tedious and time consuming process for standard tissue sampling and even more so for surveillance biopsies where in excess of 50 specimens maybe taken. A large variety of endoscopic biopsy forceps are commercially available today with the majority of the market converting to disposable forceps over the last 15 years. The current design has not fundamentally changed since its inception over 30 years ago. Whether disposable or reusable the forceps operate and function in a similar manner. The variety of biopsies forceps differ in size of the biopsy cup, the shape of the cup (oval vs. alligator), fenestrated or non-fenestrated (cup with small opening) and presence or absence of a needle. To operate the traditional double cupped biopsy forceps the cups are closed and advanced through the endoscope's instrument channel. Under direct endoscopic visualization, the forceps are opened and further advanced into a selection of mucosa area for sampling. Pressing the open forceps onto the mucosa to obtain a specific depth. The forceps are then closed to pinch and bite off or tear away forcibly (avulsed) a mucosal sample. The sample held in the jaw of the forceps is then retrieved by removing the biopsy forceps from the endoscope. With the aid of an assistant the specimen sample is removed from the jaws and placed into a vial. The process is then repeated for the subsequent samples. The traditional biopsy forceps design creates some of the complications experienced today but is accepted as the standard as there is no better alternative available.

Further detail of the traditional biopsy forceps function and its shortcomings is as follows: After insertion and the jaws open (spanning tip to tip 7-12 mm), the physician will push the open jaws against the mucosal wall with enough pressure he feels is necessary to achieve the desired depth of sample (with varying degrees of consistency and success). The jaws are then closed to bite and secure that sample and the forceps are tugged or pulled away to tear away forcibly (avulsed) a mucosal tissue sample. However, when this is accomplished much of the specimen is crushed along the outer edges. The quality of a specimen sample is judged by the following parameters: weight (mg), size ($mm^3$), depth, crush artifact, sheering effect (artificial distortion of the epithelium) and adequacy of the specimens for histological information. They can be categorized as inadequate, suboptimal, and adequate. As much as 50% of the specimens are suboptimal or inadequate showing crush artifact or they are superficial so that histopathological assessment is unattainable. As long as more than 50% of the tissue area is not crushed it should allow adequate (not optimal) assessment of the histopathological features of the specimen. If the depth of the tissue was less than the full mucosal thickness and/or the mucosal area was less than 5 $mm^2$ then histopathological assessment is compromised.

The traditional biopsy forceps compel gastroenterologist to take bigger samples to compensate for its functional design limitations. This has lead to introduction of larger jawed jumbo forceps spanning tip to tip up to 12 mm. The jumbo forceps' bigger sample provides more for the pathologist to work with. The presumption is the larger samples will allow for proper histological diagnosis with at least a certain number of the tissue specimens. Unfortunately even with these larger cups a great percentage is not adequate due to shearing or crush artifact. These inadequate samples have held the key to a more accurate diagnosis but due to their condition were not salvageable.

As an attempt to streamline the biopsy procedure one manufacture claims to have a biopsy forceps device that can take up to two tissue specimens in a single pass. The forceps are sold at a premium price as the market recognizes the value getting multiple tissue samples in one pass, saving time. Research indicates this product has not been very successful. Its design actually limits the size of tissue sample and causes additional crushing which both reduce the quality for pathology. The conclusion is that physicians are not willing to give up quality of pathology to save time.

For decades little has changed with the collection of endoscopic biopsy tissue specimens. Once a tissue sample is taken the endoscopic biopsy forceps are withdrawn from the biopsy channel of the endoscope very carefully by the nurse or GI technician. Colon forceps are 230 cm in length and upper forceps are 160 cm in length. Both are only 2.3 mm in diameter so much care is taken not to fling patient fluids as they are removed from the endoscope. Once the forceps are out of the endoscope the GI assistant maintains control of the distal end and carefully opens the cups exposing the tissue specimen. At this point the forceps are either dipped into a specimen vial filled with fixative and shaken to dislodge the specimen from the cups of the forceps or the GI assistant uses a needle and carefully picks the tissue out of the open cups and places the tissue into the specimen vial. On occasion the GI assistant may orient the tissue specimen onto a piece of gauze in order to help facilitate the laboratory processing. This is a very tedious, time consuming process with plenty of opportunity to further damage the specimen. The forceps are then closed and passed down the biopsy channel to the site where another biopsy is taken and the process is repeated again and again until a sufficient number of samples are taken from this particular area in question.

BRIEF DESCRIPTION OF THE DRAWINGS

Preferred and alternative examples of the present invention are described in detail below with reference to the following drawings depicted in FIGS. 1-37;

FIGS. 12A-12D schematically depict the plunging deployment of the multiple core biopsy device specimen chamber 16 to the tissue depth defined by the depth stops 18 and subsequent cutting action of the single edge blade 20 within tissue 19;

FIGS. 19A-19D schematically depict alternative embodiments of depth stop wire configurations deployed from the sheath 14 housing the perpendicular single blade single axis specimen chamber 16;

FIGS. 21A-21G schematically depict structure and deployment operations of the perpendicular double cantilevered blade single axis specimen chamber 160;

FIGS. 25A-25F schematically depict structure and deployment operations of the perpendicular double cantilevered blade single axis specimen chamber 188 with four depth stops 18;

FIG. 33 presents an alternate cross-sectional and perspective views depicting specimen chamber 188 deployment and blade operation shown in FIGS. 25A-F above;

FIG. 34 presents additional cross-sectional and perspective views specimen chamber 188 deployment and blade operation depicted in FIGS. 25A-F above;

DETAILED DESCRIPTION

Figure 1:
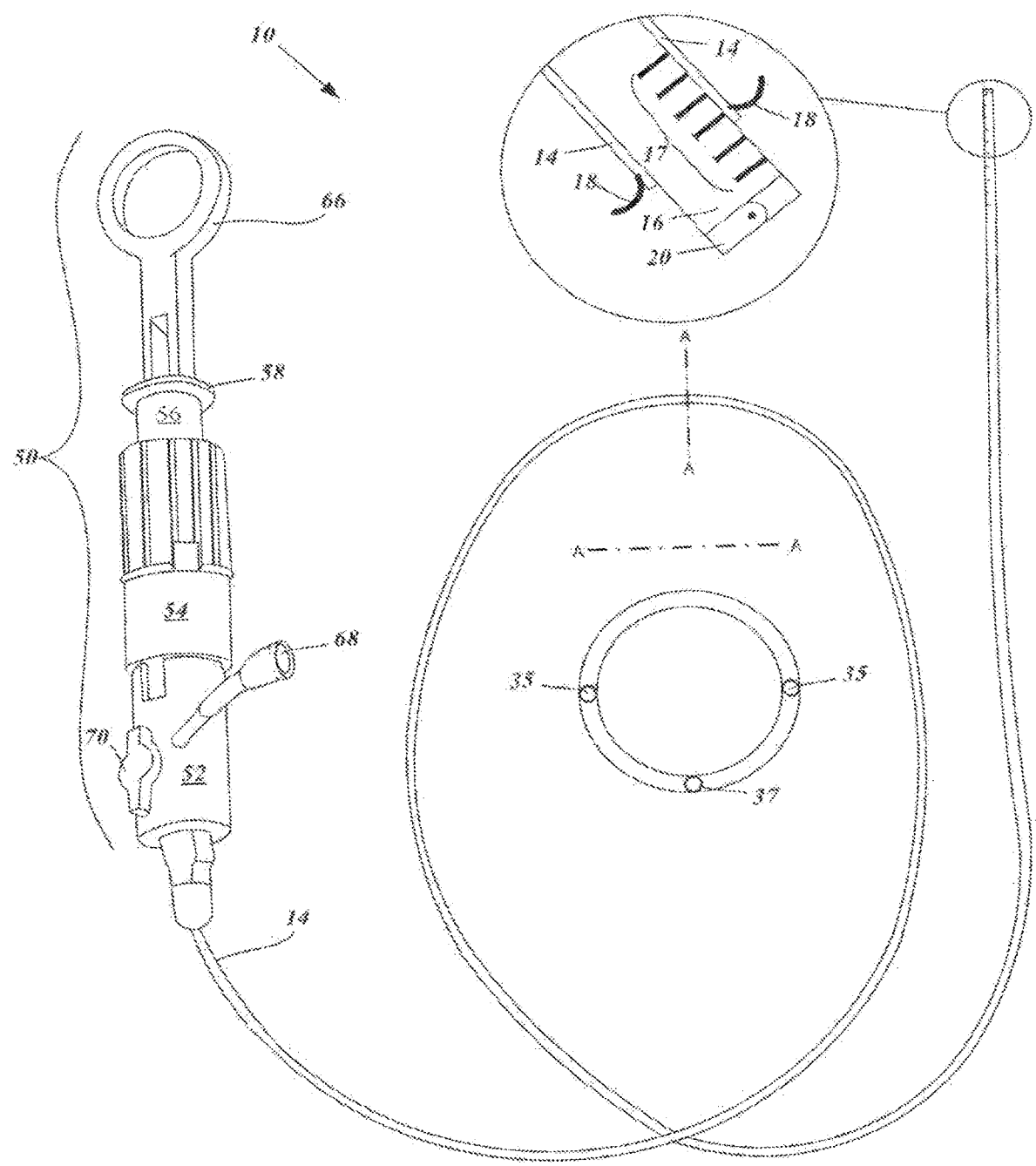
FIG. 1 schematically depicts a multiple core biopsy device 10 deployable from the biopsy channel of a flexible endoscope; having a single rotating blade affixed to the tissue contact end of a specimen chamber 16 to obtain hemispheric ally cut specimens using a multifunction biopsy device handle 50.

A Multiple Core Biopsy (MCB) device with a substantially cylindrically-shaped core and a sharp forward-facing cutting edge is configured to acquire multiple tissue biopsy samples during a single endoscopic procedure. The tissue biopsy sections are either temporarily stored within the specimen chamber, or aspirated through the device into a specimen management system maintaining sampling order and specimen orientation. If they are temporarily stored in the specimen chamber the specimens are removed by expelling into a specimen management system after the MCB is removed for the scope. Expulsion is achieved by a reverse fluid flush in communication with the specimen chamber with preservation of the specimen's order and orientation into a specimen management system. Once the samples are contained in the specimen management system it is removed and labeled for processing. With the specimen chamber cleared the MCB is ready for alternate site sampling. The MCB device specimen chamber may be configured to have a forward-facing cutting edge fitted with a single pivotable arced cutting blade rotating about an axis or, alternatively, two counter rotating and opposing arced cutting blades. The sharpness of the forward-facing cutting edge enables acquisition of high quality specimens, substantially free of crush defects.

Other embodiments include a stylet that aids the MCB device to penetrate targeted biopsy sites for single or multiple core specimens taken and retrieved in a similar manner.

Further disclosed are particular embodiments concerning a core biopsy device having a forward-facing cutting edge with either single or dual counter rotating blades is configured to acquire multiple biopsy specimens and temporarily store them within a specimen chamber located beneath the cutting edge. The core biopsy device is insertable and removable from a biopsy channel of an endoscope. The core biopsy device includes an endoscopically visible ruler with depth gauge increments. Other embodiments include deployable depth stops to restrain the plunging of the specimen chamber to not exceed a set distance. Multiple samples contained within the specimen chamber are removed via flushing from a syringe adapter when the device is removed from the endoscope. Alternatively the multiple specimens are removed under applied suction to an external specimen management chamber attached to the proximal end of the biopsy access port [without removing the MCB device from the scope]. Either way the order and orientation of the removed specimens are preserved.

Yet further described herein are substantially cylindrically-shaped multiple core biopsy device having a specimen chamber located within a flexible sheath traversing through the biopsy channel of an endoscope. The specimen chamber is equipped with forward-facing cutting edges and is operable by a multifunction handle manipulated by a user at the proximal end. The multiple core biopsy device includes a distally located specimen chamber with forward facing cutting edges intended for placement in the lumen of an esophagus, internally within the stomach, or internally within the upper and lower gastrointestinal system of a patent. The cutting edges of the specimen chamber are so configured to acquire multiple tissue biopsy samples with preservation of tissue integrity, orientation, and sequence order acquired in a single-pass during an endoscopic procedure. The configuration of the cutting blade or blades avoids tissue crushing and provides for clearly delineated samples for temporary storage in a specimen chamber during the endoscopic procedure. In other embodiments the shapes of the multiple core biopsy device may have shapes other than circular. For example, the shapes may include oval, rectangular, square, or triangular configurations.

In alternate embodiments the multiple core biopsy device may be fitted with a specimen management system that utilizes a suction assisted collection chamber attached to the biopsy access port. Samples temporally stored in the distally located specimen chamber located internally in-situ within the patient may be removed from the specimen chamber by gentle suction and transferred to the external specimen management system with preservation of tissue sample orientation, and acquisition order. This patient specimen management system provides for continued sample collection to resume at different anatomical sites without removing the MCB device from the endoscope.

The multiple tissue biopsy sections are stored within the specimen chamber or specimen cavity, or alternatively, aspirated through the device and into a specimen management system chamber located at the proximal end of the biopsy device during endoscopic examination and sampling.

After biopsy sampling is finished for a specific area in question and the specimens are stored within the specimen chamber the biopsy device is removed from the scope and the specimens are removed by expelling into a specimen management system with a fluid flush using a syringe in fluid communication with the specimen chamber with preservation of the specimen's order and orientation.

The core biopsy device may be fitted with either the specimen chamber configured to have a forward-facing single pivotable arced cutting blade rotating about an axis or, alternatively, two counter rotating and opposing cutting blades. The multiple specimens obtained from either the single rotating blade or the two opposing blades are of high quality tissue biopsy sections that are substantially free of crush defects.

In general the specification describes below a core biopsy device having a forward-facing cutting edge with either single or dual counter rotating blades is configured to acquire multiple biopsy specimens and temporarily store them within a specimen chamber located beneath the cutting edge. The core biopsy device is insertable and removable from a biopsy channel of an endoscope. The core biopsy device includes an endoscopically visible ruler with depth gauge increments. Other embodiments include deployable depth stops. A user plunges the biopsy device to a selected tissue depth, by selecting variable ruler increments. Biopsied tissue is then excised in sizes defined by the travel path of the single blade or dual cutting blades and plunged distances, and contained within the specimen chamber. Multiple samples contained within a specimen chamber are removed via flushing from a syringe adapter when the device is removed from the patient. The order and orientation of the removed specimens are preserved.

The core biopsy device described herein is configured to acquire at least one tissue biopsy sample within a tubular-shaped cavity or specimen chamber. The core biopsy device is insertable and removable from a biopsy channel of an endoscope and includes a single rotating cutting blade or dual counter rotating cutting blades at the tissue contact end of a tube having a cavity. The core biopsy device includes an endoscopically visible ruler with depth gauge increments and include deployable depth stops. A user plunges the biopsy devices to a selected tissue depth. Biopsied tissue is then excised in sizes defined by the travel path of the single blade or dual cutting blades and plunged distances, and contained within a specimen chamber. Samples contained within a specimen chamber during a single endoscopic procedure are removable via flushing from a syringe adapter such that the biopsied tissue specimens are flushed from the forward facing cutting edges keeping the specimens in order and orientation.

Also described below includes a core biopsy device configured to acquire at least one tissue biopsy sample within a tubular cavity is described. The core biopsy device is insertable and removable from a biopsy channel of an endoscope and includes an outer protective sheath a single rotating cutting blade or dual counter rotating cutting blades at the tissue contact end of the inner core tube having a cavity. The core biopsy device includes an endoscopically visible ruler with depth gauge increments. Other embodiments include deployable depth stops. A user plunges the biopsy devices to a selected tissue depth. Biopsied tissue is then excised in sizes defined by the travel path of the single blade or dual cutting blades and plunged distances, and propelled into the tube cavity as a consequence of applied cutting, tissue plunging forces and potentially controlled aspiration. Biopsy procedures are repeated as desired and sequential and multiple tissue sections are propelled into the cavity to displace the previous biopsy section deeper into the tubular cavity. Other descriptions include a multiple core biopsy system utilizes a flushing syringe to expel and remove multiple biopsy sections in reverse order to their endoscopic sampling while at the same time maintaining order and orientation.

The multiple core biopsy device is insertable and removable through the biopsy channel of an endoscope. Particular embodiments of the core biopsy device include a single rotating cutting blade or dual counter rotating cutting blades at the tissue contact end of tubular chamber that houses the biopsy specimens during an endoscopic procedure. The core biopsy device includes an endoscopically visible ruler with depth gauge increments that is on the exterior side of the specimen chamber. Other embodiments include deployable tissue plunger stops. A user plunges the biopsy devices to a selected tissue depth. Biopsied tissue is then excised in sizes defined by the travel path of the single blade or dual cutting blades and plunged distances, and propelled into the tube cavity as a consequence of applied cutting and tissue plunging forces. Biopsy procedures are repeated as desired and sequential and multiple tissue sections are propelled into the cavity to displace the previous biopsy section deeper into the tubular cavity. Other descriptions include a multiple core biopsy system utilizes a flushing syringe to expel and remove multiple biopsy sections in reverse order to their endoscopic sampling while at the same time maintaining order and orientation. Another embodiment of the core biopsy device applies controlled suction to the proximal end of the device aspirating the individual tissue specimens into the Specimen Management System in order to their endoscopic sampling while at the same time maintaining order and orientation of subsequent samples.

Illustrated below are embodiments for a single cutting blade and multiple cutting blade biopsy devices and describe systems and methods of procuring multiple biopsy tissue samples from a single endoscopic examination substantially devoid of crush artifacts. In general a core biopsy device operable by a user is described. In one embodiment, the core biopsy device includes a flexible tube having a tissue contact end (distal), a manipulation end controllable by the user (proximal), and a cavity located between the tissue contact and manipulation ends. At the tissue contact end resides a rotatable cutting blade. Connected between the rotatable cutting blade and the manipulation end is a blade control member. Biopsy tissue is obtained during endoscopic procedures when the user plunges the tissue contact end to a set depth, manipulates the blade control member from the manipulation end to pivot the rotatable cutting blade to excise a tissue section defined by the travel path of the rotatable cutting blade, and insert the tissue section into the cavity as a consequence of the cutting and plunging forces applied to the excised tissue. Other embodiments allow for the rotatable cutting blade to comprise two counter-rotating sections. Multiple biopsy samples may be acquired by repeating the plunging and cutting action by either the single rotating cutting blade or dual counter-rotating cutting blades wherein a sequential excised tissue sections are propelled into the cavity, thereby displacing the earlier sampled tissue section further into the cavity. A series of sequential biopsies may be thus acquired with minimum crush effect during a single pass of the biopsy device.

In another embodiment, a multiple core biopsy (MCB) system is described. The multiple core biopsy system includes the biopsy device having a flushing port located near the manipulation end. The flushing port detachably receives a syringe having a flushing fluid. For sequential biopsies located in the cavity, either obtained by the single rotating cutting blade or the dual counter-rotating cutting blades biopsy devices, the multiple core biopsy device is removed from the endoscope, and receives a fluid flush delivered from the (proximal) manipulation end. The fluid flush thereby displaces the tissue section biopsies in reverse order to the order that they were sampled during the single pass of the biopsy device.

In yet other embodiments described include a biopsy device having a removable stylet, the biopsy device being operable by a person who is using an image-guided system. The biopsy device includes a rigid sheath equipped with the removable stylet, the rigid sheath having depth markings visible by the image-guided system and a terminus with a distal chamber configured with a forward facing cutting edge comprising a fixed blade and at least one movable blade. The biopsy device further includes a manipulation end controllable by the user to plunge the forward facing cutting edge at a sampling locus after removal of the stylet at a depth selected by the user based on the depth markings and to engage a cutting action by the at least one movable blade at the depth selected to acquire at least one specimen storable in the distal chamber. The biopsy device may acquire additional depths obtained at deeper depths at the sampling locus. The rigid sheathed biopsy device may also be transferred to a different sampling locus to acquire additional specimens procured at increasing depths at that different sampling locus.

Other embodiments of the multiple core sampling device provide for a flexible sheath having a distally located specimen chamber that is fitted with forward facing cutting surfaces, having a fixed and moveable portion that when the moveable portion is in the stowed position, is then configured for tissue plunging at controlled distances. To insure that unwanted tissue is not sampled while undergoing sheath insertion for placement at an anatomical region-of-interest for sought-after tissue sampling, the flexible sheath is also fitted with a stylet to prevent the unwanted entrance of tissues not desired for specimen sampling. Once the distal specimen chamber is positioned for multiple core biopsy sampling at the anatomical region-of-interest, the stylet is removed to allow specimen retrieval into the distal specimen chamber from multiple plunge-and-cut operations at pre-set or user-adjusted specimen chamber plunging depths. The cut operations occur after the plunging action to the pre-set or user-selected depths by the deployment of the moveable from its stowed position.

Particular embodiments of the biopsy devices, systems, and methods encompass obtaining mucosal biopsies of the esophagus, stomach, small intestine, and large intestine. Endoscopic guided biopsies are the primary diagnostic approach to most GI disorders. Biopsy specimens obtained at endoscopy help not only to differentiate benign from malignant diseases, but also to establish the precise nature of the abnormality, be it infectious, inflammatory, or neoplastic.

FIGS. 1-37 illustrate systems and devices for a MCB (multiple core biopsy) device that provides superior design and functionality to that of traditional biopsy forceps which rely on bigger specimens for quality samples. The MCB design provides for multiple specimens in a single pass, which speeds the procedure and reduces patient sedation time. Due to the cutting blade embodiment designs described, the MCB device virtually eliminates the crush factor inherent in the traditional biopsy forceps design. In all, a higher number of superior quality, consistent depth biopsy specimens are procured from the suspect area in the same time it takes to obtain a single traditional biopsy specimen. Generally an increased number of biopsy specimens correlates to a higher detection rate with improved outcomes.

The MCB device, which provides an advanced design and functionality, would soon expect to become the standard for taking diagnostic biopsies. This meshes well in a managed-care environment where everyone is being pressured to do more with less facilitating faster procedural turnaround time with improved outcomes.

Further clinical advantages of the MCB include that specimens may be taken and kept in order and orientated, and have consistent depth via depth stops, set core advancement and blade swing as discussed below that provides or precise variable depth sampling. The MCB includes an internal reservoir channel allows for easy retrieval and transferring of multiple specimens and a single or dual-motion cutting mechanism smoothly severs the specimen at the prescribed depth virtually eliminating any crush artifact so that specimens may be obtained with minimal mucosa surface area disruption providing less bleeding. The MCB designs, as discussed below, provide for rapid target specimen selection aids in speeding of obtaining biopsy specimens in a single MCB insertion. The MCB includes a forward facing cylindrical cutting edge having a single arced cutting blade or dual opposing cutting blades. Aspiration may be controlled by a MCB user during tissue biopsies either right after the specimen is excised or right prior to or as the physician or other user is thrusting the device into the mucosal wall for a subsequent sample. Removal of the specimens from the MCB is accomplished by either removing the MCB from the scope and flushing specimens retrograde out the distal end or by aspiration through the entire length of MCB device into a specimen management system outside the body while the MCB device remains in the scope and patient. The specimen retrieval methods maintain or preserve the orientation and order of the tissue specimens.

FIG. 1 schematically depicts a multiple core biopsy device 10 (MCB 10) deployable from the biopsy channel of a flexible endoscope. The MCB 10 includes a single rotating blade 20 affixed to the tissue contact end of a specimen chamber 16 to obtain hemispherically cut specimens using a multifunction biopsy device handle 50. The specimen chamber 16 is accessed from the multifunction biopsy device handle 50 of the MCB 10 via the biopsy access port 68 through the specimen channel which routes through to the distal tip. The specimen channel is a coaxial lumen that moves within the exterior cannula or sheath 14, that is flexible and engageable with the biopsy channel of an endoscope. The luer-lock allows a syringe (not shown) to be connected with biopsy access port 68 to flush multiple core specimens from the specimen chamber 16 after the cannula 14 is removed from the endoscope. Alternatively, the biopsy access port 68 may be connected to a proximal specimen management system described in FIGS. 3 and 4 below. The specimen chamber 16 includes multiple markings 17, each marking denoting a standard length. The size of the tissue cut is defined by the plunge distance and the hemispherical traveling distance defined by the single rotatable blade 20. Deployment of depth stops 18 limit the plunge depth of the forward facing cutting edge of the specimen chamber 16.

Figure 7:
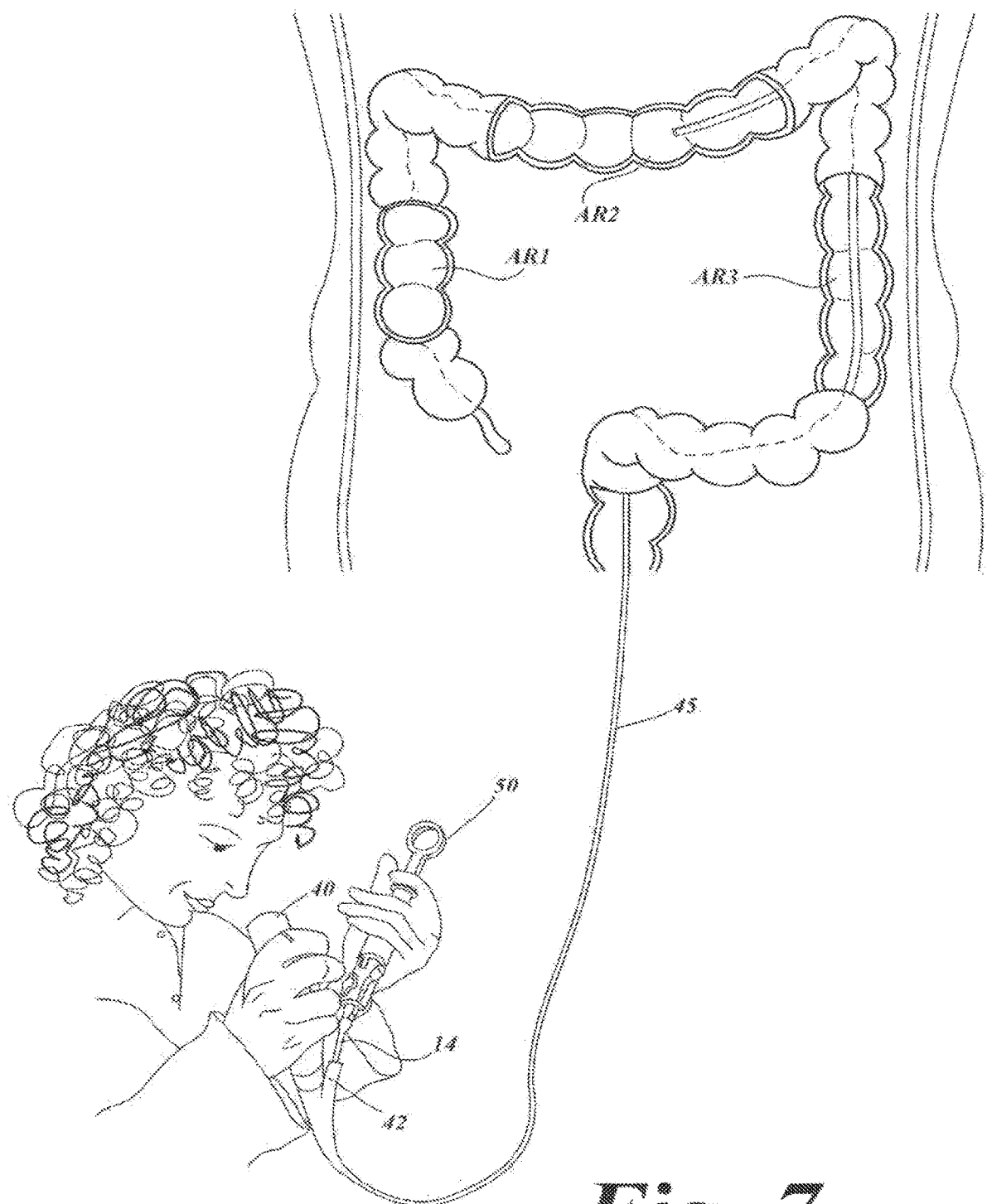
FIG. 7 schematically depicts the operation of the multiple core biopsy device 10 in a lower intestinal endoscopic procedure.
Figure 8:
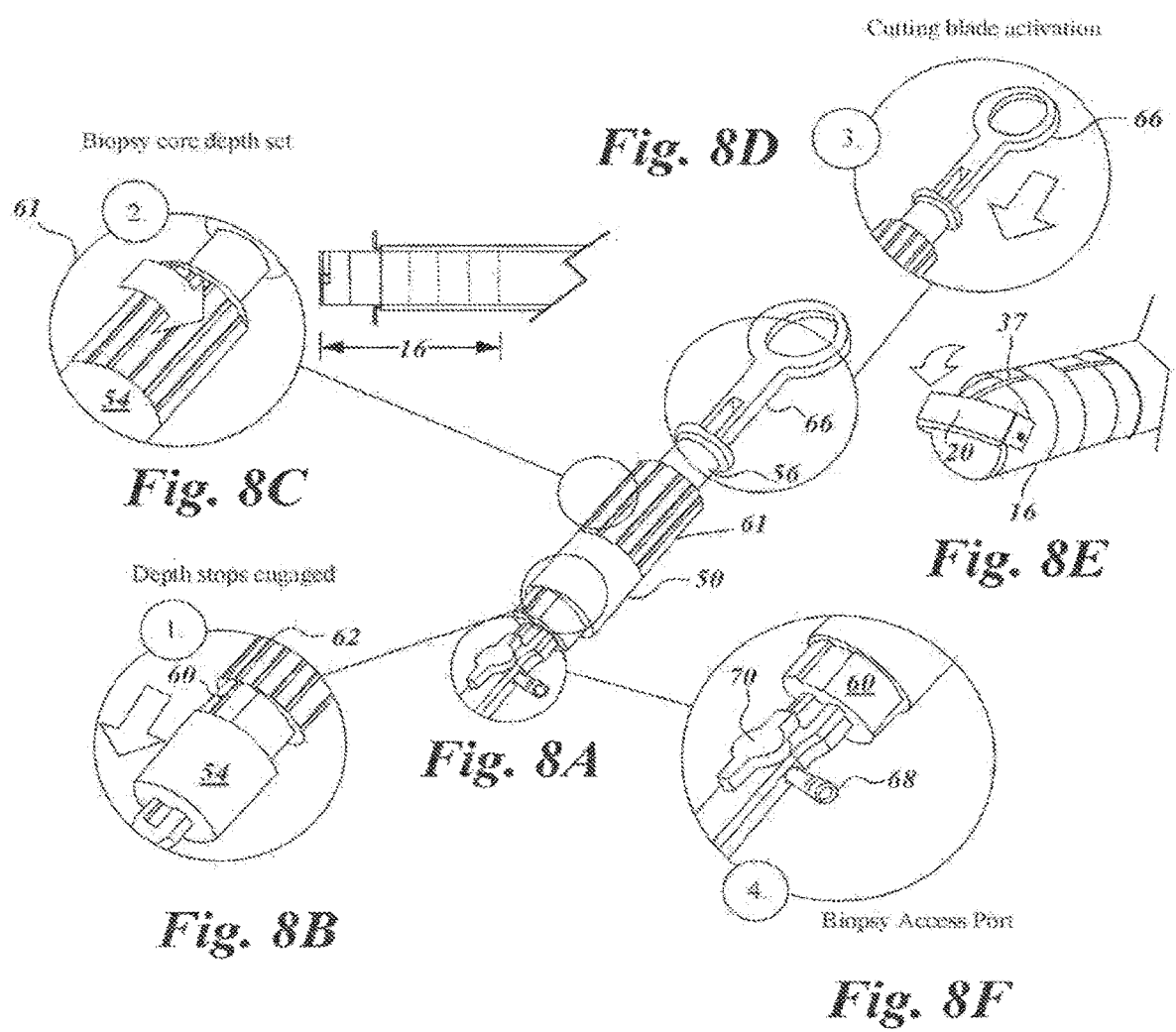
FIGS. 8A-8F depict movement operations of the multi-function biopsy device handle 50 to deploy advancement and cutting actions of the specimen chamber 16.

The cannula or sheath 14 is passed through the biopsy channel of a flexible endoscope as shown in FIG. 7 below. Operation of the multifunction handle 50 to engage the depth stops 18, advance the specimen chamber 16 and to activate cutting action by the blade 20 is described in FIGS. 8A-F below. Other specimen chambers, including chambers 116, 120, 124, 128, 132, 136, 140, 160, 188 and 190 shown and described in FIGS. 8A-25D discussed and shown below, may be similarly fitted to the biopsy device 10. Additional structural features of the specimen chamber 16 in relation to the sheath 14 is illustrated and described in FIG. 26 below.

Cross-section along line A-A shows depth stop control wires 35, and a blade control wire 37. The wires convey mechanical motion between the respective depth stops 18, and cutting blade 20 at the distal end, and with multifunction handle 50 controls 54 and 56 discussed in FIG. 2 below.

Figure 2:
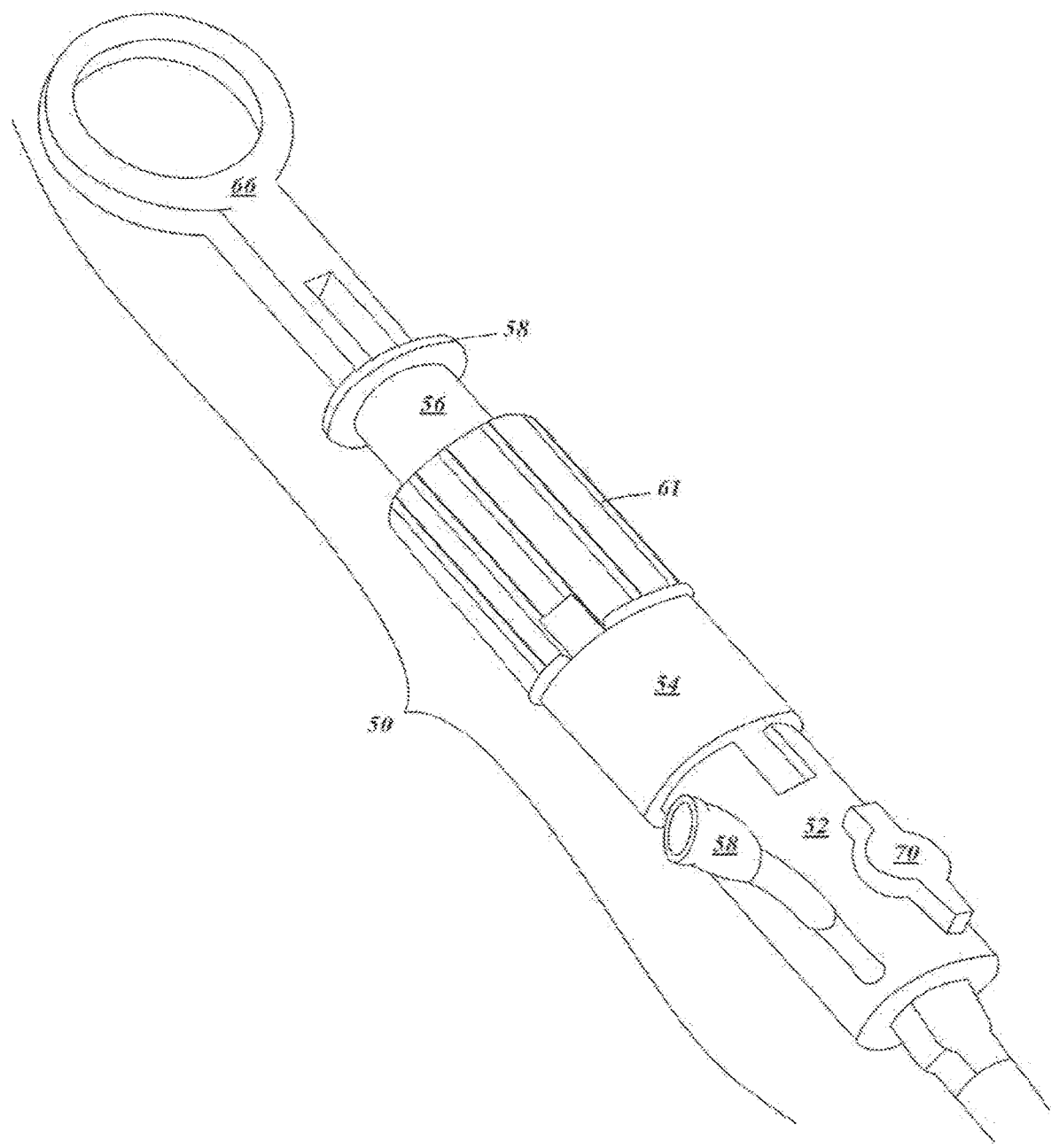
FIG. 2 schematically depicts a perspective view of the multi-function biopsy device handle 50.

FIG. 2 schematically depicts a perspective view of the multi-function biopsy device handle 50. The handle 50 includes a depth stop deployment control 54, a specimen chamber advancement control 61, and a blade activation control 66. The exemplary configuration shows that depth stop deployment control 54 having back-and-forth slidable motion along the long axis of the handle 50, the specimen chamber advancement control 61 having clockwise and counterclockwise rotary motion perpendicular to the long axis, and the blade activation control 66 having back-and-forth slidable motion along the long axis. Other motion configurations of the controls 54, 61, and 66 are possible. The back-and-forth and rotation/counter rotation motions provide the push and pull motions conveyed to stow or deploy the specimen chamber 16, the depth stops 18, and the rotary cutting action of the blade 20. The blade activation control 66 includes a motion limiter 58 that limits rotary cutting action to not exceed beyond that rotary motion needed to convey a complete cut of the blade 20 and a thumbhole 66 to ergonomically and conveniently be manipulated by the user or handle 50 operator.

Figure 3:
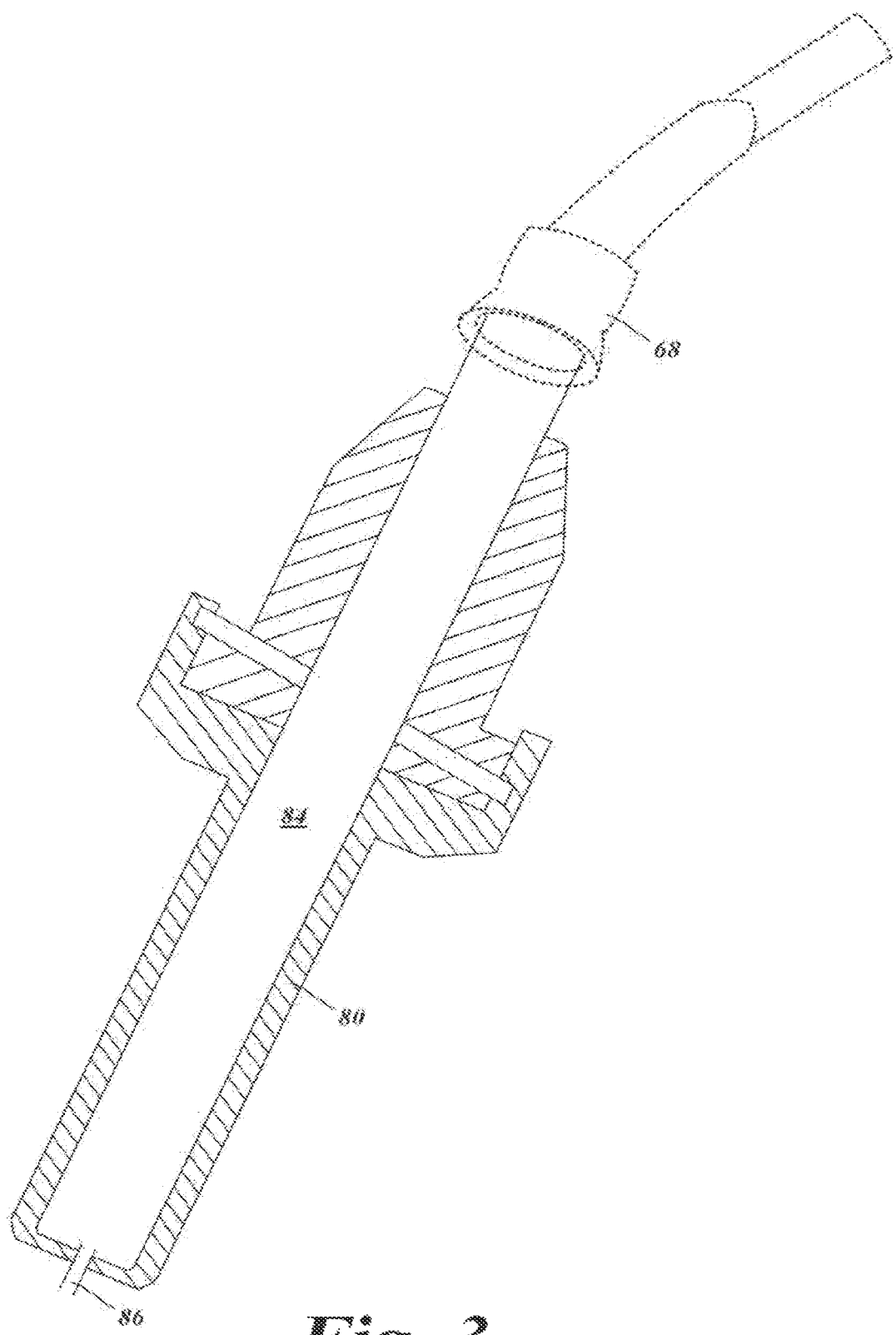
FIG. 3 schematically depicts a cross-sectional view of a proximal specimen chamber 80 connectable with the multi-function handle 50.

FIG. 3 schematically depicts a cross-sectional view of a proximal specimen management system 80 connectable with the multi-function biopsy device handle 50 via biopsy access port 68. Internal specimen management chamber 84 is connectable with the biopsy access port 68 and upon receiving suction conveyed via suction channel 86, single or multiple samples temporarily housed in the distally located specimen chamber 16 located internal within the patient are transferred to the specimen management chamber 84. Transferred single or multiply acquired specimens are structurally preserved and in the order and orientation of the specimens taken.

Figure 4:
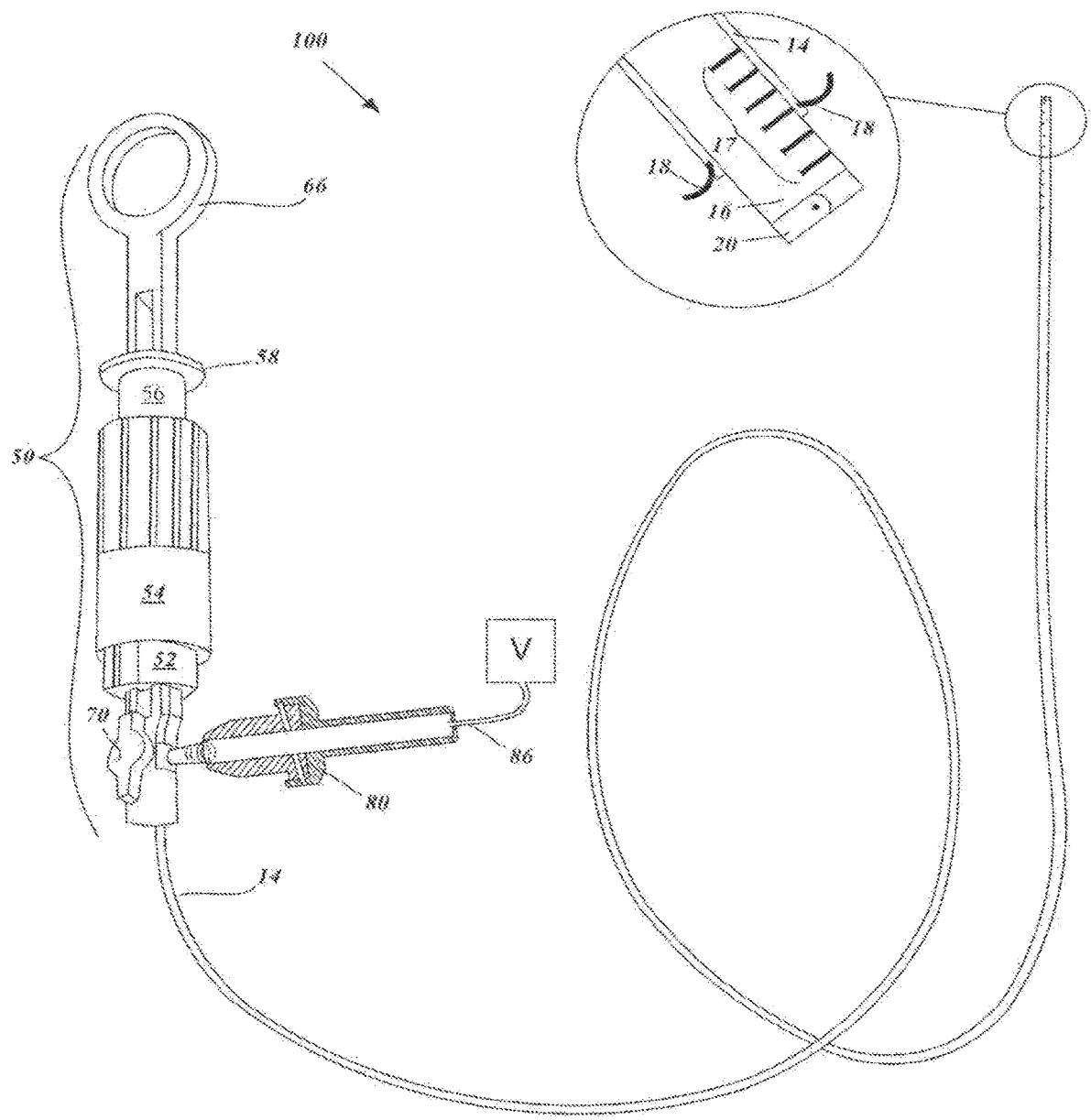
FIG. 4 schematically depicts a multiple core biopsy device system 100 deployable via the channel of a flexible endoscope.

FIG. 4 schematically depicts a multiplecore biopsy system 100 (MCBS 100) deployable via the biopsy channel of a flexible endoscope shown in FIGS. 7 and 10 below. A suction source V is connectable with the suction channel 86. Upon application of a suction, either as applied by a syringe (not shown), suction pump (not shown) or house suction source (not shown), any specimens temporarily housed within the specimen chamber 16 are transferred to the specimen management chamber 84 with maintenance of specimen integrity and sampling order and orientation. Other specimen chambers, including 116, 120, 124, 128, 132, 136, 140, 160, 188 and 190 (not shown) described in FIGS. 8A-25D discussed and shown below, may be similarly configured with the MCBS 100.

Figure 5:
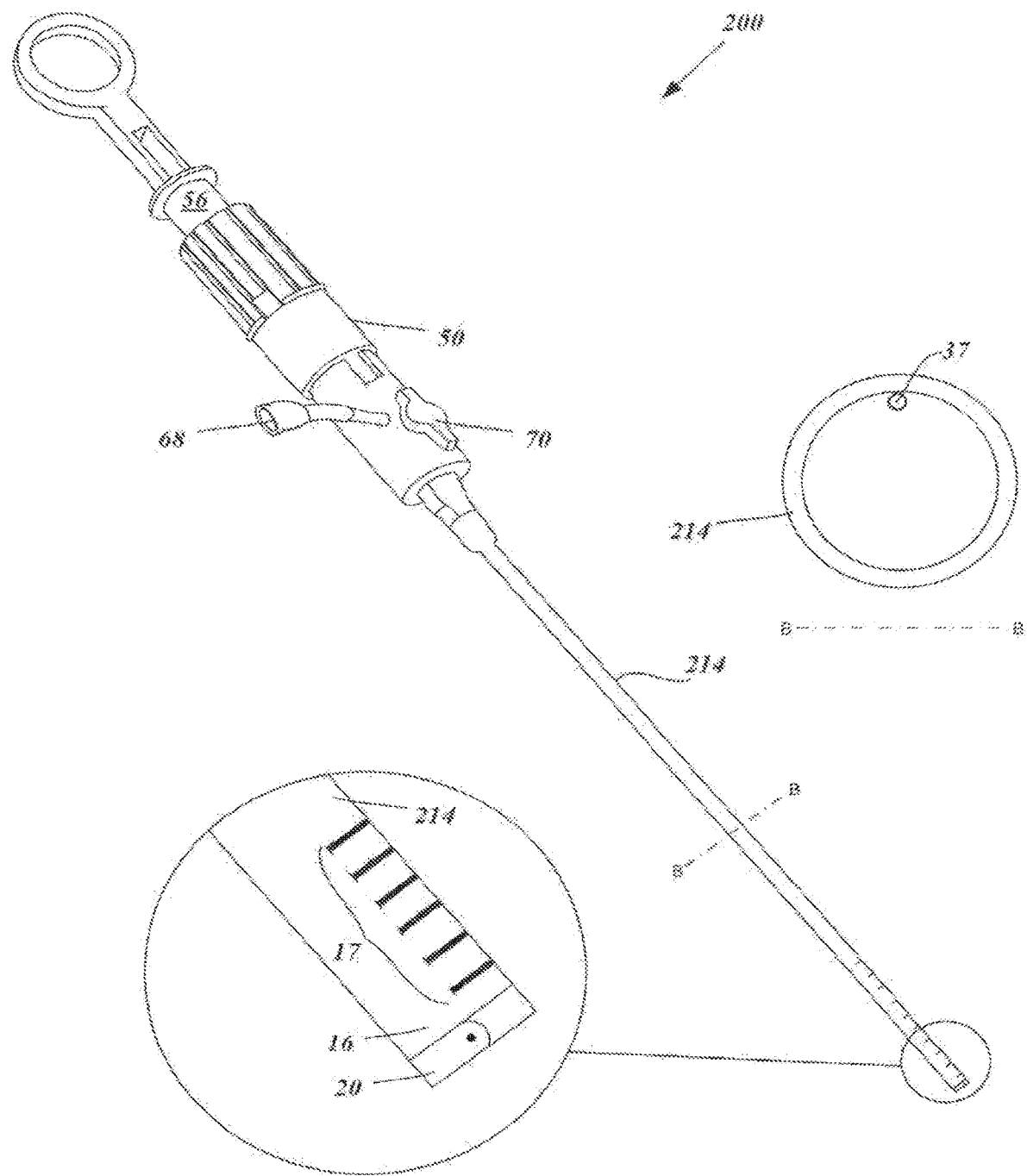
FIG. 5 schematically depicts a percutaneious multiple core biopsy device 200.

FIG. 5 schematically depicts a percutaneous multiple core biopsy (PMCB) device 200. Used in conjunction with image-guided systems (not shown) such as ultrasound or X-ray visualization technologies, the PMCB 200 includes the proximally located multifunctional handle 50 connected with a semi-rigid to rigid shaft 214 to which may be fitted at its distal end the specimen chambers 16. Other specimen chambers, including 116, 120, 124, 128, 132, 136, 140, 160, 188 and 190 (not shown) described in FIGS. 8A-25D discussed and shown below, may be similarly fitted to the PMCB device 200. Multiple specimen cores may be consecutively obtained within the same puncture locus of a targeted organ, say a lung, kidney or liver, to obtain structurally preserved, devoid of crush artifacts, and maintenance of specimen integrity and sampling order and orientation to allow meaningful histological examination. Incremental markings 17, having a known distance between each marking 17 of 1 or 2 mm, may be made with radio-opaque markings to be visible in X-ray guidance systems or other contrast agent media to make visible in ultrasound guidance systems.

Cross-section along line B-B shows the blade wire 37 which conveys mechanical motion between the blade 20 of specimen chamber 16 at the distal end and with multifunction handle 50 blade control 56 discussed in FIG. 2 above. The handle 50 operator plunges the PMCB device 200 using the markings distance 17. The operator engages blade control 56 to acquire a blade 20 cut histological quality specimen and plunges deeper within the same organ puncture locus to acquire additional specimens similarly cut by the blade 20 via blade control 56.

Figure 6:
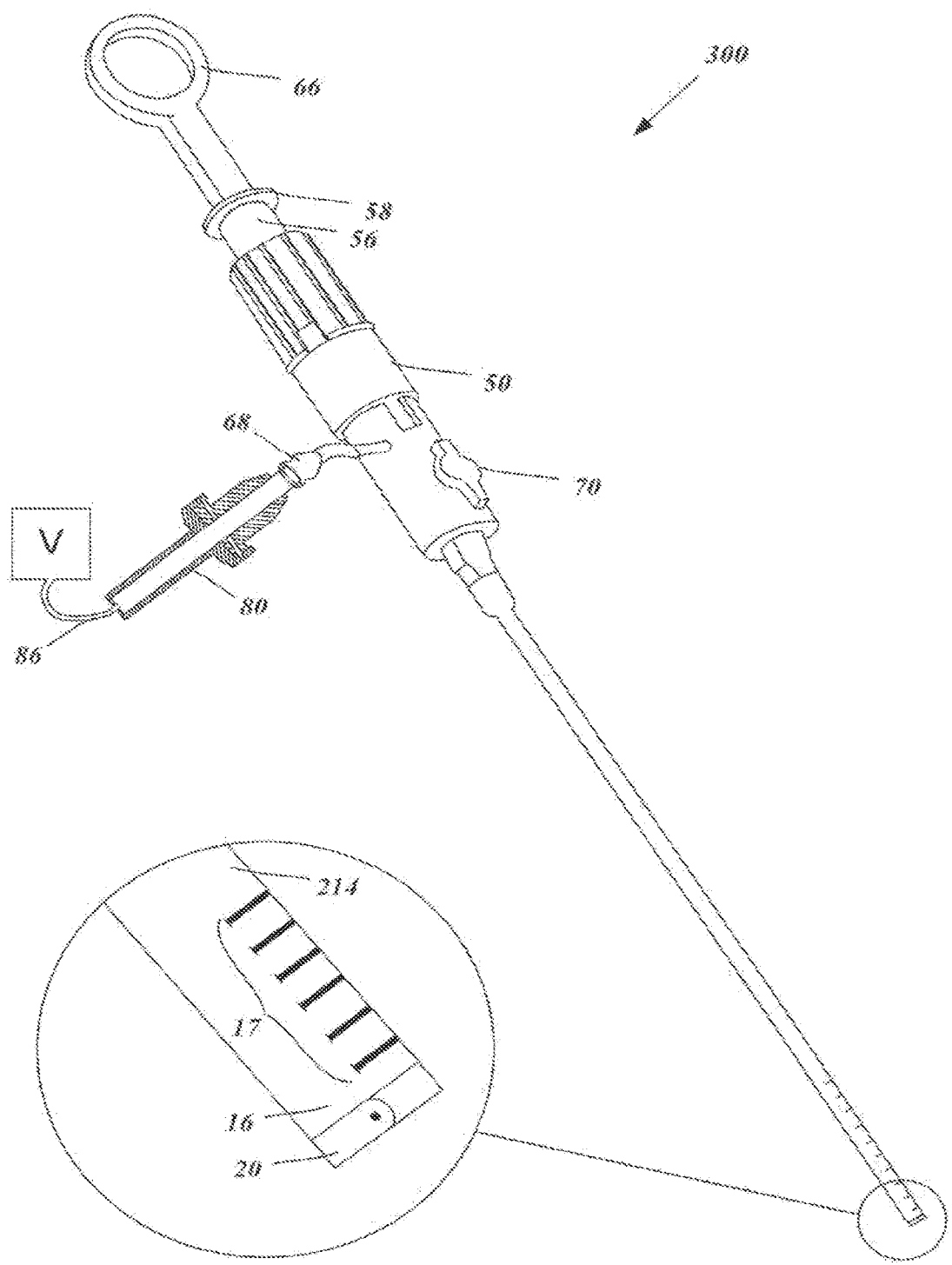
FIG. 6 schematically depicts a percutaneious multiple core biopsy system 300.

FIG. 6 schematically depicts a percutaneous multi-core biopsy system 300. Connectable with the proximal specimen chamber 80 that is attachable to a suction source V, multiple samples obtained at a particular organ puncture location may be transferred under suction to the proximal specimen management chamber 80 once removed the PMCB device is removed from the organ or patient. Under image guidance systems (not shown) or direct vision, the specimen chambers 16, or alternatively, specimen chambers 116, 120, 124, 128, 132, 136, 140, 160, 188 and 190 described in FIGS. 8A-25D below may proceed to another organ puncture locus to obtain a different set of multiple specimens for temporary storage within specimen chambers 16-190. Once removed from the patient, a gentle source of suction V, say via a syringe, pump, or room provided suction may be applied to transfer the different set of multiple specimens from distally specimen chambers 16-190 to proximally located specimen management chamber 80.

FIG. 7 schematically depicts the operation of the multiple core biopsy device 10 in a large intestinal endoscopic procedure conducted by an operator. Endoscope 40 receives the sheath 14 of MCB 10 or MCBS 100 through endoscope 40 biopsy port 42 and is passed through the biopsy channel located within endoscope 40 insertion tube 45. By way of example, insertion tube 45 is routed through the large gastrointestinal track's ascending, transverse, and descending branches. Respective cutaways show a first anatomical region AR1, a second anatomical region AR2, and a third anatomical region AR3. The specimen chamber 16 is deployed from the endoscope's 40 biopsy channel to obtain consecutive tissue core specimens within anatomical regions 1, 2, or 3. As depicted the MCB device 10 or the MCBS 100 may be used for ocular-based endoscopes as shown, or alternatively, for video-based endoscopes (not shown) in which images of the MCB device 10 operation is presented on nearby monitors (not shown) viewable by the MCB device 10 or MCBS 100 user.

FIGS. 8A-8F depict movement operations of the multifunction biopsy device handle 50 to deploy depth stops, advance the specimen chamber core 16, and activate the cutting blade 20. The general method of using the MCB 10 or MCBS 100 begins with the specimen chamber 16 is retracted within the sheath 14 and blade 20 in a stowed or un-deployed state to allow the MCB/S 10/100 to be safely passed through the biopsy channel of the endoscope depicted in FIG. 7. Once it exits the distal end of the endoscope in direct visualization of the physician the depth stops 18 are deployed (Step 1). As shown in FIGS. 8A/8B, the depth stop deployment control 54 is slid in the direction of the motion arrow along channel 60. After deployment of the depth stops 18 performed in Step 1, the core biopsy specimen chamber or shaft 16 can be advanced to the set depth, and so emerges beyond the terminus of the sheath 14 (Step 2) to be equivalent to the plunging depth defined by the consistent depth via depth stops 18, set core advancement and blade swing. As shown in FIG. 8C, rotation of the specimen chamber control 61 will advance the specimen chamber 16 to a set depth. Once the specimen chamber is advanced, a biopsy location is chosen for receiving the plunging or thrusting action of the specimen chamber 16 into the mucosal wall to the set depths in which the depth stops 18 prevent the specimen chamber 16 from further penetration than desired. Once the specimen chamber 16 is plunged to the set depth the blade control member 66 is advanced (Step 3) and the tissue specimen excised by cutting action of the blade 20. The thumbhole 66 provides an ergonomic structure to exert pushing or pulling actions of the blade control. The MCB 10 or MCBS 100 is retracted from the mucosal wall, and the blade control 66 is engaged to stow the blade 20 back into its un-deployed state and another biopsy site is selected and Step 3 is repeated until the desired numbers of biopsies are retrieved. Previously collected specimens already occupying the lumen space of the specimen chamber 16 are further displaced more internally therein, as shown in FIGS. 25D-F below. At this point the specimen chamber shaft control 61 is turned to retract the specimen chamber 16 into sheath 14. The depth stop control 54 is then pulled back to retract the depth stops 18 within the sheath 14. If specimens temporarily housed within the lumen space of the specimen chamber 16 are not suction transferred to the proximal specimen management chamber 80 shown in FIG. 4, the sheath 14 is removed from the biopsy channel of the endoscope to allow removal via retrograde flushing of the specimens contained within the lumen of the specimen chamber 16 with preservation of sample integrity and sampling order and orientation.

Figure 9:
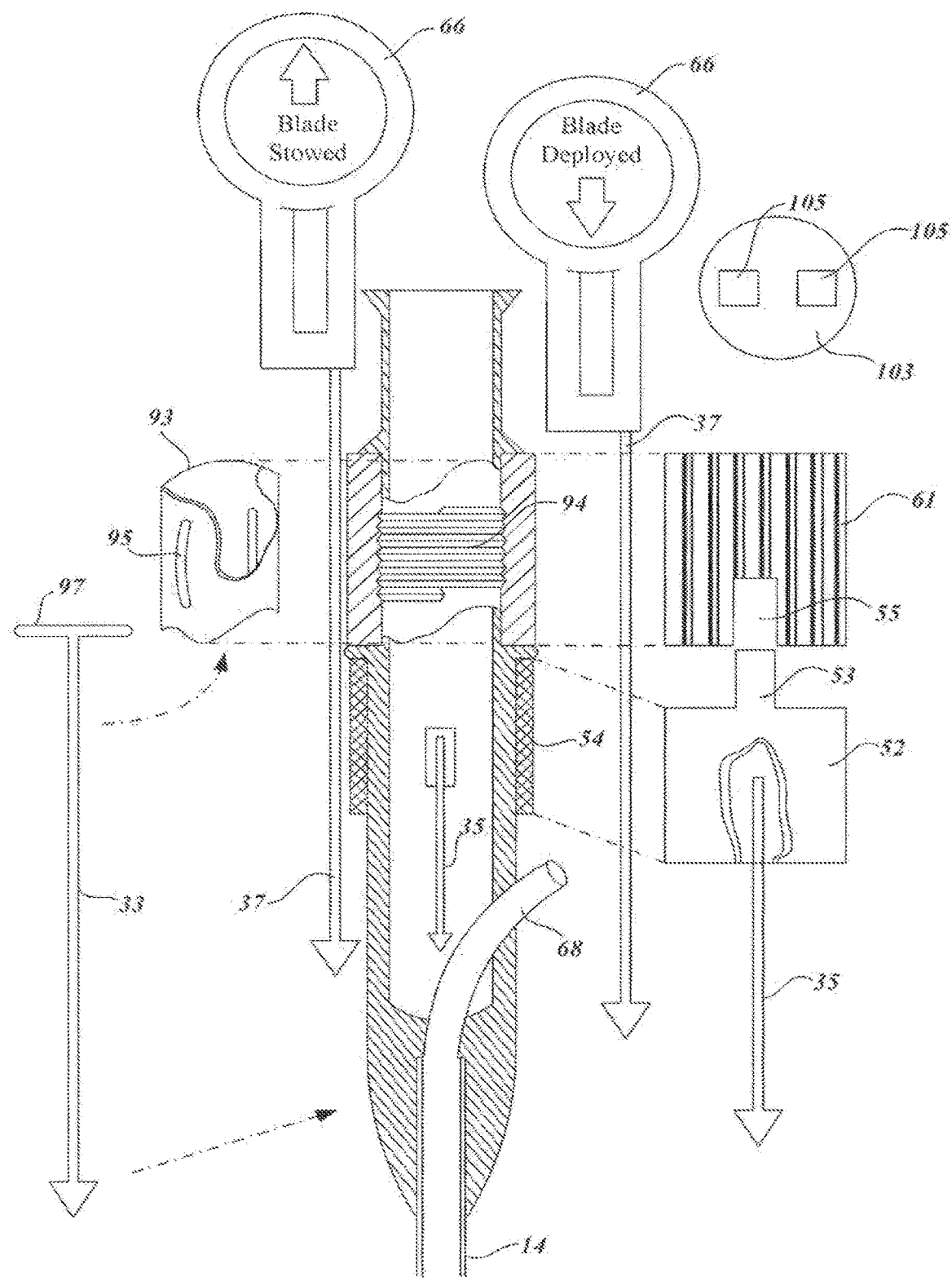
FIG. 9 depicts side top, and perspective views of the components of the multifunction biopsy device handle to effect the movement actions to deploy and/or implement cutting actions of the specimen chamber 16.

FIG. 9 depicts side top, and perspective views of the components of the multifunction biopsy device handle to effect the movement actions to deploy and/or implement cutting actions of the specimen chamber 16. Depth stop deployment is conveyed by the depth stop slider control 54 that is mechanically connectable with the depth stop wire 35. Deployment of the depth stops 18 is initiated by downward direction of the slider control 54 until locked into place, and retraction or stowage of the depth stops 18 is initiated by movement reversal, that is, upward movement conveyed by the slider control 54 to the depth stop wire 35. The slider control 54 has a projection 53 engagement with slot 55 of specimen chamber control 61. The depth stops 18 are deployed first. The removal of the projection 53 from the slot 55 allows rotary operation of the specimen chamber control 61 to permit deployment of the specimen chamber 16 beyond the distal terminal end of the sheath 14.

The rotary motion of the specimen chamber control 61 is conveyed by helical turns 94 that engages motion converter 93. Specimen chamber wire 33 is attached to crossbar 97 that engages motion converter's 93 curved slot 95 to produce a linearly directed, back-and-forth or push-pull motion along the long axis of handle 50 to and through the specimen chamber wire 33 which advances and retracts the specimen channel which includes the specimen chamber.

The back-and-forth or push-pull motion by the thumbhole 66 is conveyed by slotted shaft 56 that is mechanically coupled with the blade wire 37. Cutting action by the blade 20 is conveyed by a downwardly directed pushing force applied to the thumbhole 66 by a handle 50 user or operator. Similarly, retraction of the blade 20 to its stowed position is initiated by an upwardly directed pulling force conveyed by the thumbhole 66. Conversely, the handle 50 can be configured such that an upward pulling motion engages cutting action and a downward pushing motion engages blade stowage.

After specimens are collected within the specimen chamber 16, the blade 20 is returned to its stowed state by motion of thumbhole slider 66. Thereafter, the specimen chamber control 61 is rotated to retract the specimen chamber 16-190 to place the slot 55 to be engageable with the projection 53. Upward movement of the depth stop slider control 54 retracts depth stops 18 within the sheath 14 upon slidable engagement of the projection 53 with slot 55.

Figure 10:
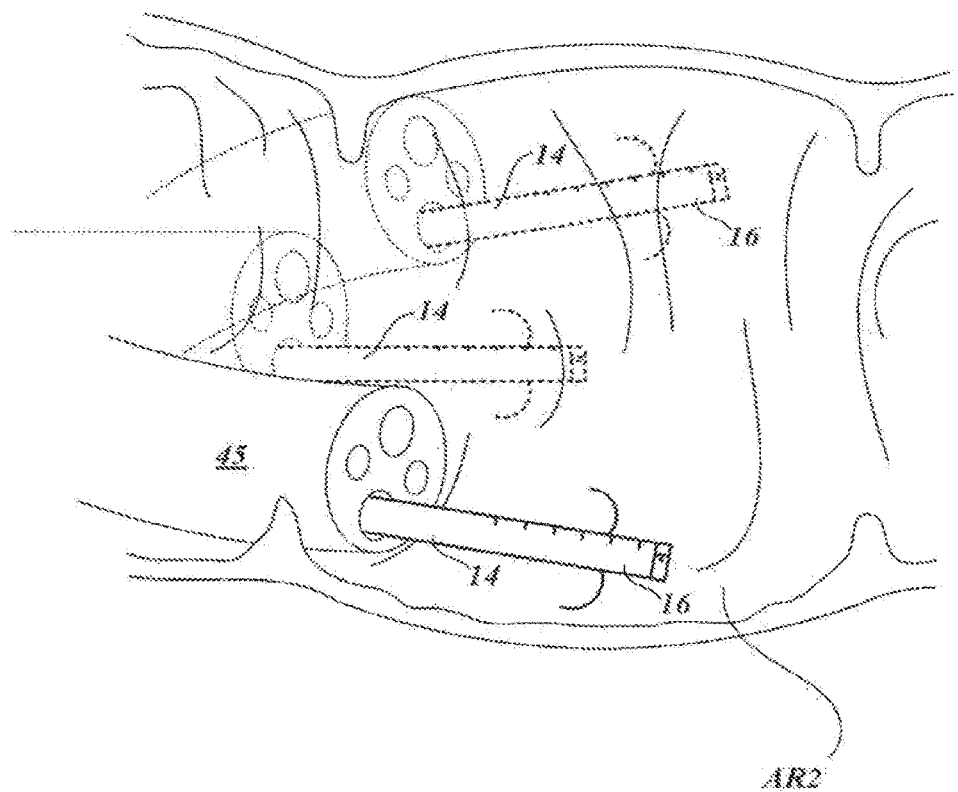
FIG. 10 schematically depicts the deployment of the multiple core biopsy device 10 from the biopsy channel of a flexible endoscope to obtain multiple tissue core specimens within anatomical region 2 depicted in FIG. 7.

FIG. 10 schematically depicts tissue specimen sampling deployments of the multiple core biopsy device 10 from the biopsy channel of a flexible endoscope to obtain multiple tissue core specimens within anatomical region 2 depicted in FIG. 7. Here three separate deployments of the specimen chamber 16 with the depth stops 18 set, one deployment depicted with solid lines and two deployments depicted in dashed lines. Operation of the blade 20 after the specimen chamber 16 has been plunged into the tissue to obtain histological grade core specimens depicted in FIGS. 12A-D below.

Figure 11A:
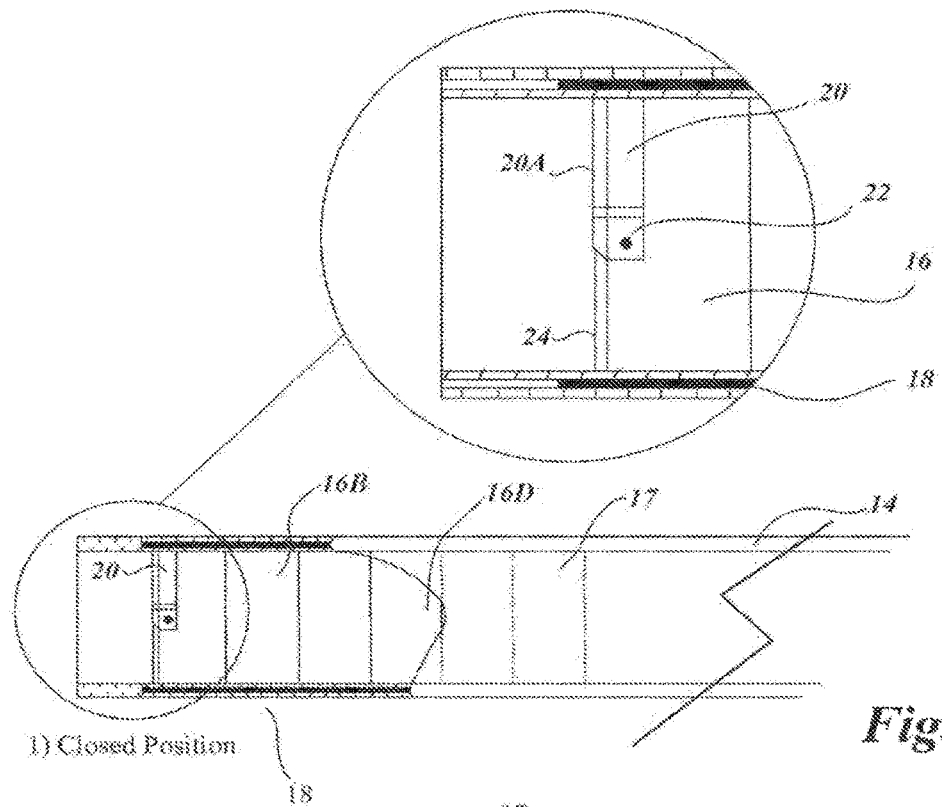
FIGS. 11A-11C depict deployment of the multiple core biopsy device 10 specimen chamber 16 and depth stops 18 from sheath 14.
Figure 11B:
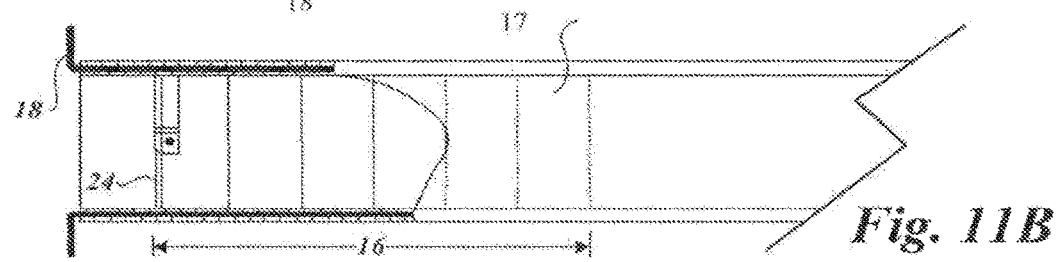
Figure 11C:
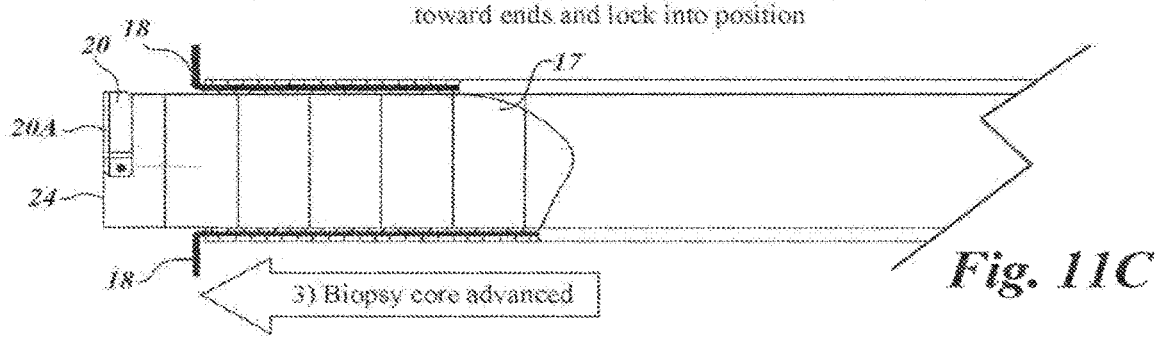

FIGS. 11A-11C depicts deployment of the multi-core biopsy device 10 specimen chamber 16 and depth stops 18 from sheath 14. Prior to plunging the forward facing cutting surfaces of the specimen chamber's 16 movable blade 20 and/or stationary regions, the specimen chamber is advanced from its sheath 14 and locked into place via specimen chamber control 61 of multifunction handle 50. In FIG. 11A the depth stops 18 are fully retracted or in a stowed position. In FIG. 11B, the depth stops 18 emerge from the sheath 14 while the specimen chamber 16 remains retracted within the sheath 14. In FIG. 11C, the specimen chamber 16 is advanced externally from the lumen of the sheath 14 via the handle's 50 specimen chamber control 61. The specimen chamber 16 is set for plunging into the mucosal wall depicted in FIG. 12A-D below within a particular anatomical region, say AR1, 2, or 3 depicted in FIGS. 7 and 10 above.

FIGS. 12A-12D schematically depict the plunging deployment of the multiple core biopsy device specimen chamber 16 to the tissue depth defined by the depth stops 18 and subsequent cutting action of the single edge blade 20 within tissue 19. These cross-sectional depictions of FIG. 12A show the operation of specimen chamber 16 during multiple core biopsy sampling as would be undertaken within anatomical region 2 of FIG. 10 above. In general the multifunction handle 50 of the MCB 10 or MCBS 100 has the deployable depth stops 18 set by operator manipulation of the handle's 50 depth stop control 54 shown in FIG. 2.

In FIG. 12B the specimen chamber or biopsy core 16 is advanced by manipulation of the handle's 50 specimen chamber control 61 and subsequently pressed, thrusted, or plunged into the tissue. Cutting commences after plunging by manipulation of the handle's 50 blade activation control 56.

In FIG. 12C cutting action is completed by continued manipulation of the handle's 50 blade activation control 56. A newly cut specimen is thereby acquired.

Thereafter, in FIG. 12D, the newly cut specimen is delivered and pushed into temporary storage within the lumen of the specimen chamber or biopsy core 16 by re-plunging the advanced specimen chamber or biopsy core 16 into the tissue, thereby displacing or pushing the previous newly acquired cut further internally within the lumen space of the specimen chamber 16.

Figure 13A:
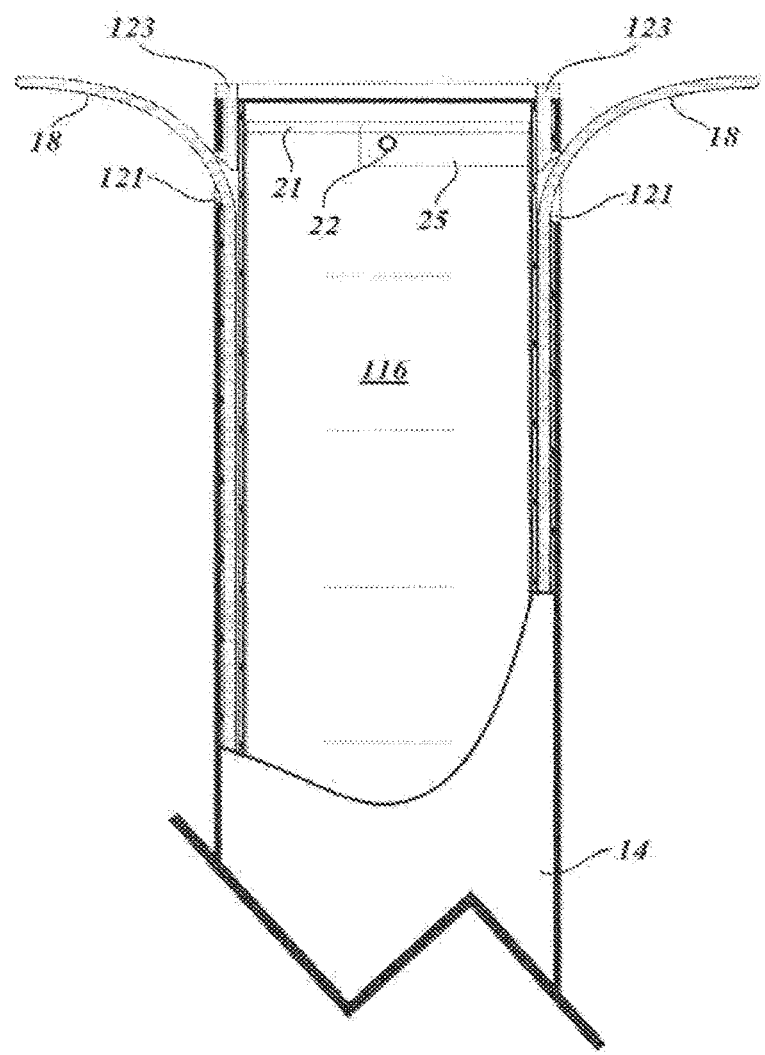
FIGS. 13A-13C schematically depict structure and deployment operations of the perpendicular single blade single axis specimen chamber 116.
Figure 13B:
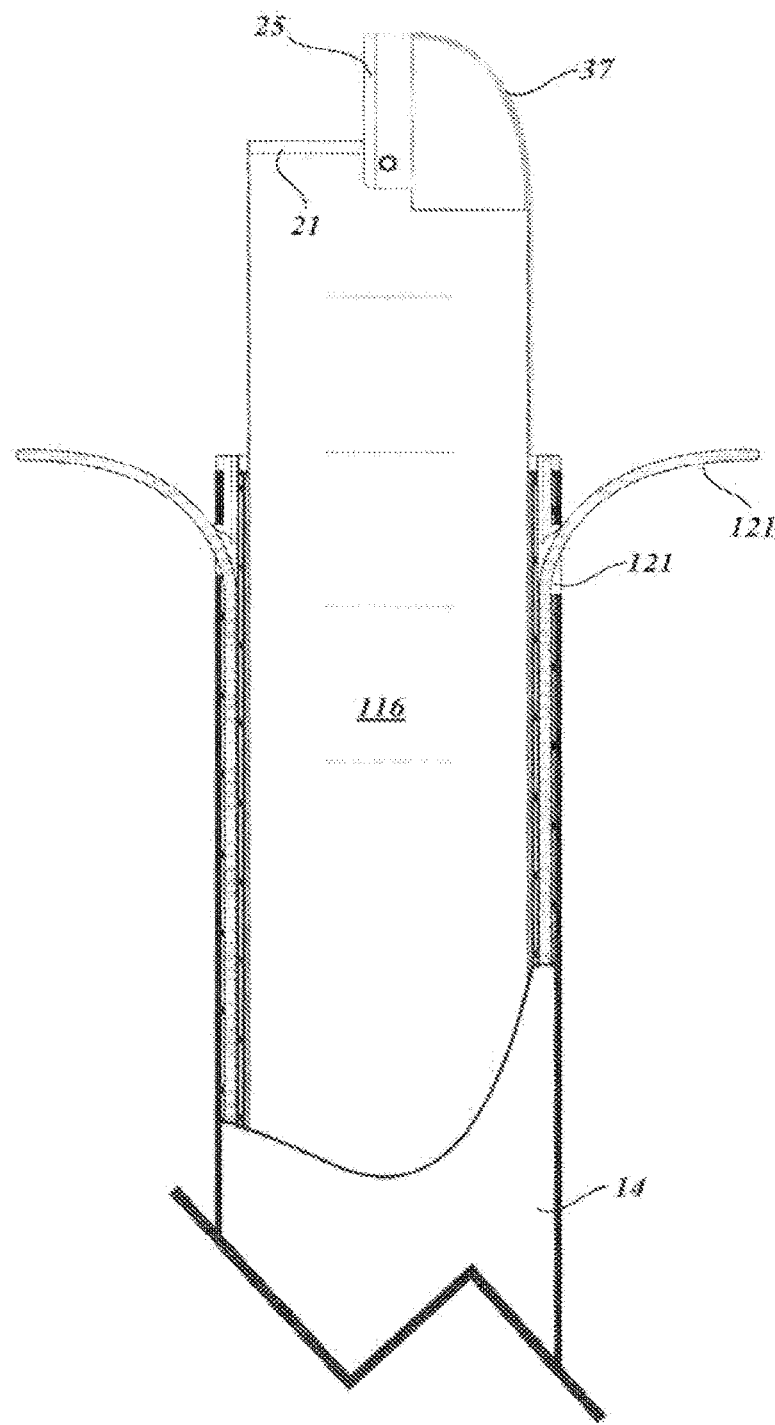
Figure 13C:
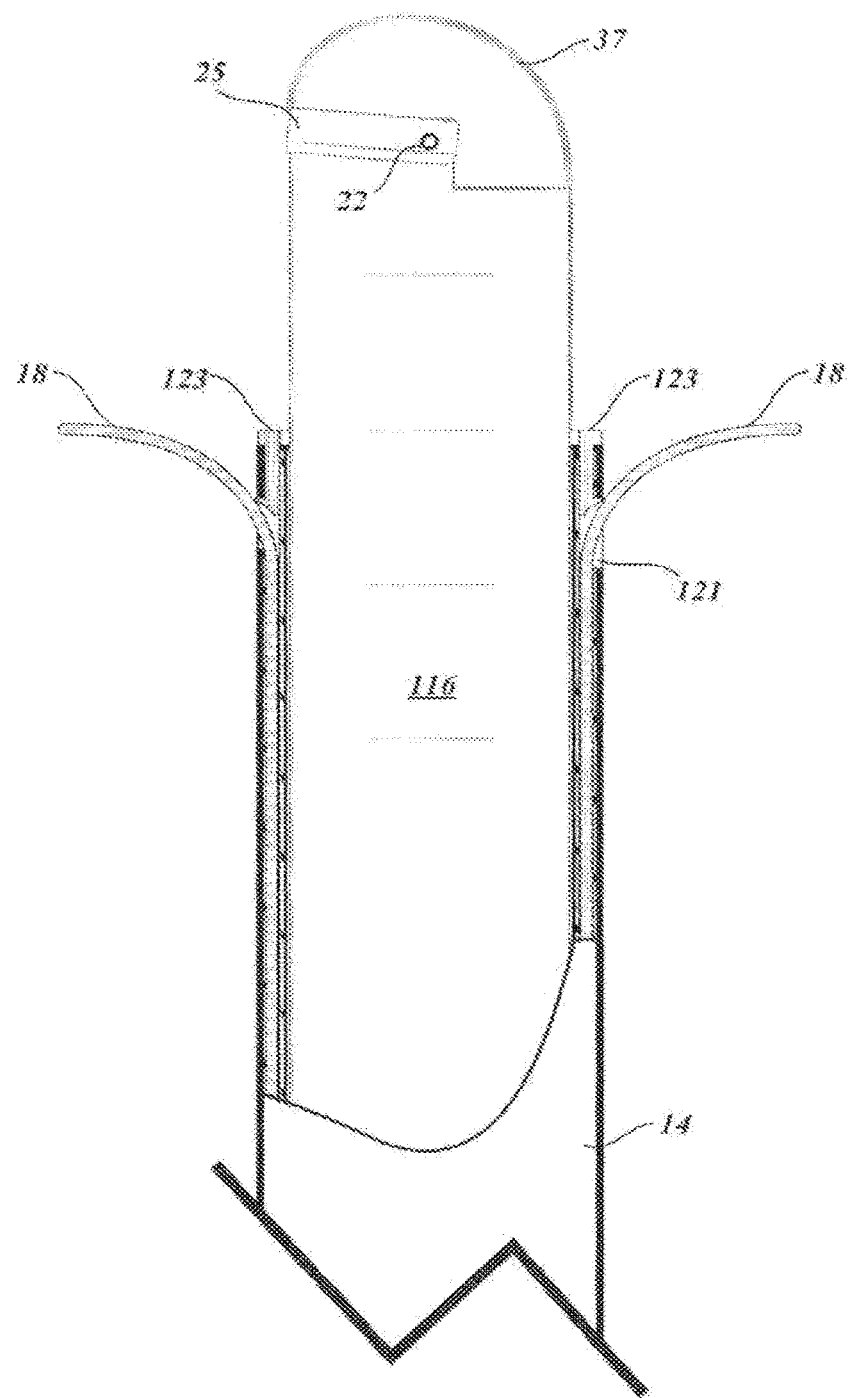

FIGS. 13A-13C schematically depict structure and deployment operations of the perpendicular single blade single axis specimen chamber 116. Presented in FIG. 13A are two cutting edges, the edge of the moveable blade 20 and the edge of the fixed portion of the facing edge of the specimen chamber 116. In the stowed position, both the cutting edge of the blade 20 and the cutting edge of the fixed portion is perpendicular to the long axis of the specimen chamber 116. The blade is rotatable about single axis pivot 22. Depth stops 18 are deployed through sheath apertures 121 via deflector posts 123.

In FIG. 13B, the specimen chamber is shown deployed. The arc of the blade 20 is deployed midway via blade control wire 37 and is at maximum height by almost the length of the blade 20. In FIG. 13C, the specimen chamber is shown deployed and the cutting action complete with the blade 20 pushed to maximum movement via blade control wire 37 and resting on the fixed portion end 21 in FIG. 13B.

Figure 14A:
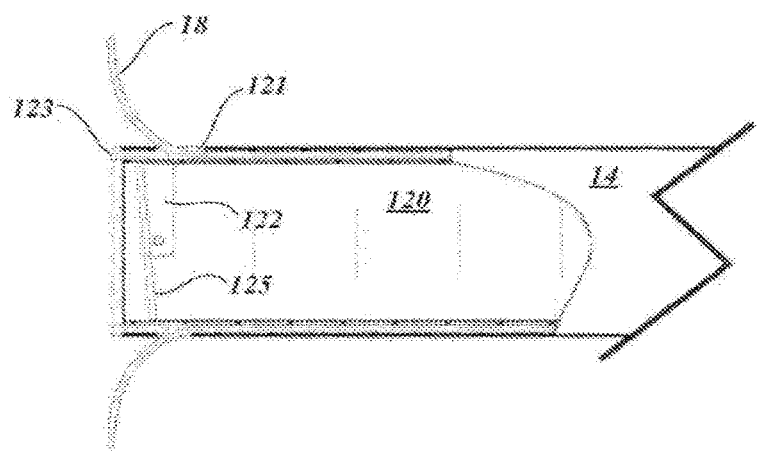
FIGS. 14A-14C schematically depict structure and deployment operations of the angled single blade single axis specimen chamber 120.
Figure 14B:
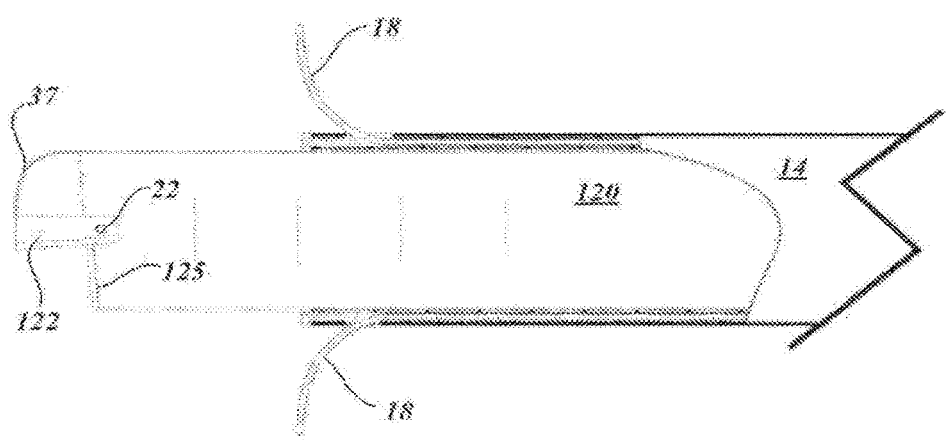
Figure 14C:
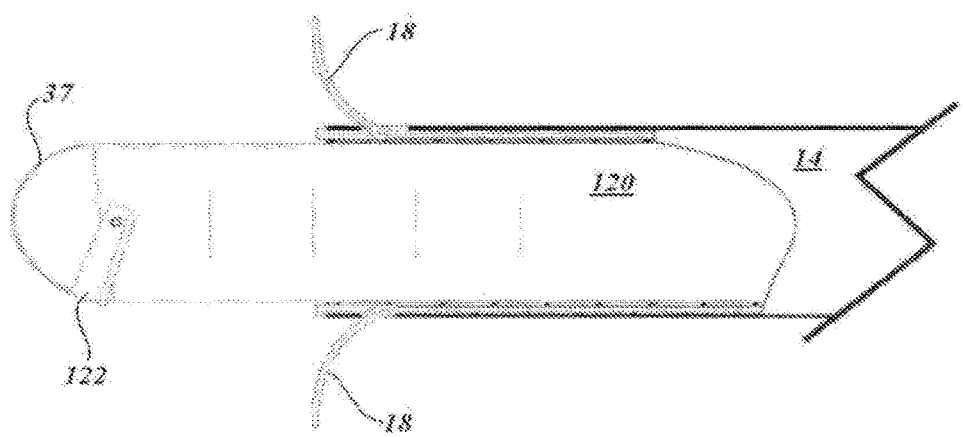

FIGS. 14A-14C schematically depict structure and deployment operations of the angled single blade single axis specimen chamber 120. Presented in FIG. 14A are two cutting edges, the edge of the moveable blade 122 and the edge of the fixed portion 125 of the facing edge of the specimen chamber 120. In the stowed position, both the cutting edge of the blade 122 and the cutting edge of the fixed portion 125 is angled or beveled relative to the long axis of the specimen chamber 120. The blade 122 is rotatable about single axis pivot 22. Depth stops 18 are similarly deployed through sheath apertures 121 via deflector posts 123.

In FIG. 14B, the specimen chamber 120 is shown deployed from the terminus of the sheath 14. The arc of the blade 122 is deployed midway via blade control wire 37 and is at maximum height by almost the length of the blade 122. In FIG. 14C, the specimen chamber 120 is shown deployed and the cutting action completed with the blade 122 pushed to maximum movement via blade control wire 37 and resting on the fixed portion end 125.

Figure 15A:
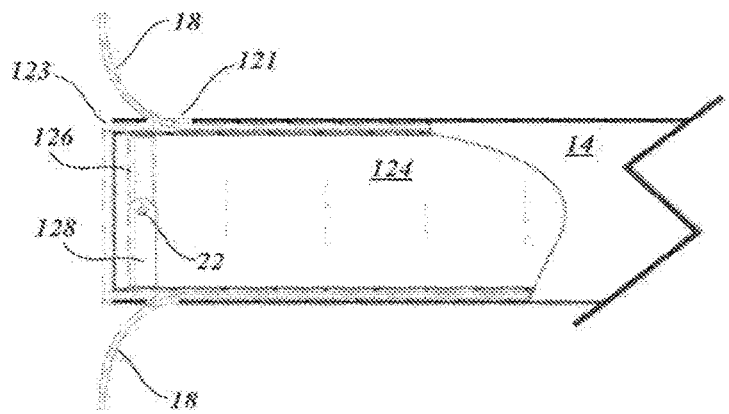
FIGS. 15A-15C schematically depict structure and deployment operations of the perpendicular double blade single axis specimen chamber 124.
Figure 15B:
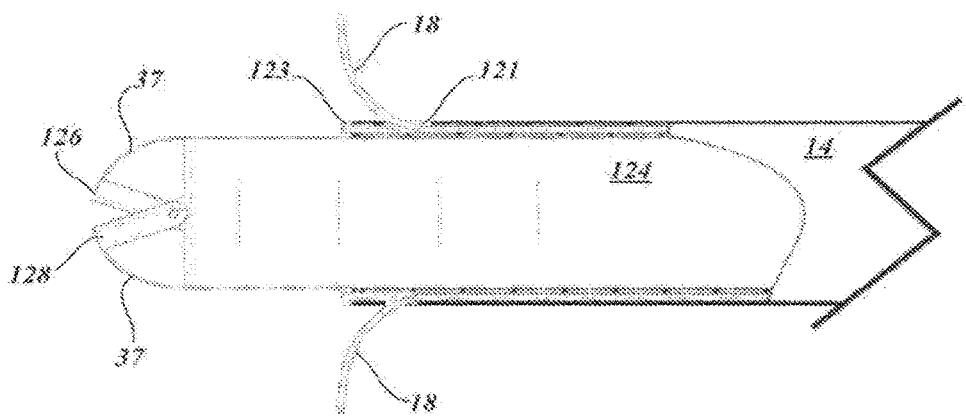
Figure 15C:
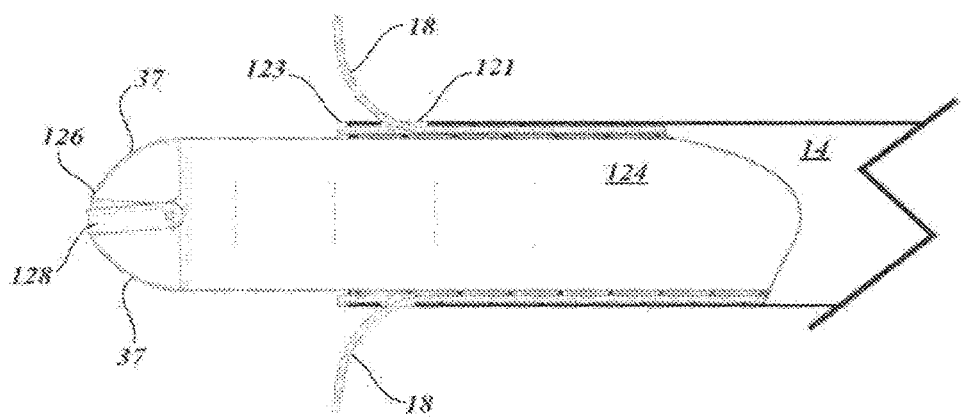

FIGS. 15A-15C schematically depict structure and deployment operations of the perpendicular double blade single axis specimen chamber 124. Presented in FIG. 14A are two rotatable cutting edges pivotable about single axis 22, a smaller cutting blade 126 and a larger cutting blade 128. The edge of the moveable blades 126 and 128 are the forward facing cutting surfaces of the specimen chamber 124. In the stowed position, both rotatable cutting edges of the knives 126 and 128 are perpendicular relative to the long axis of the specimen chamber 124. The knives 126 and 128 are rotatable about single axis pivot 22. Depth stops 18 are similarly deployed through sheath apertures 121 via deflector posts 123.

In FIG. 15B, the specimen chamber 124 is shown deployed from the terminus of the sheath 14. The arcs of the larger blade 128 and smaller blade 126 are approaching midway deployment via blade control wire 37.

In FIG. 15C, the specimen chamber 124 is shown deployed and the cutting action completed with the larger blade 128 overlapping the smaller blade 126.

Figure 16A:
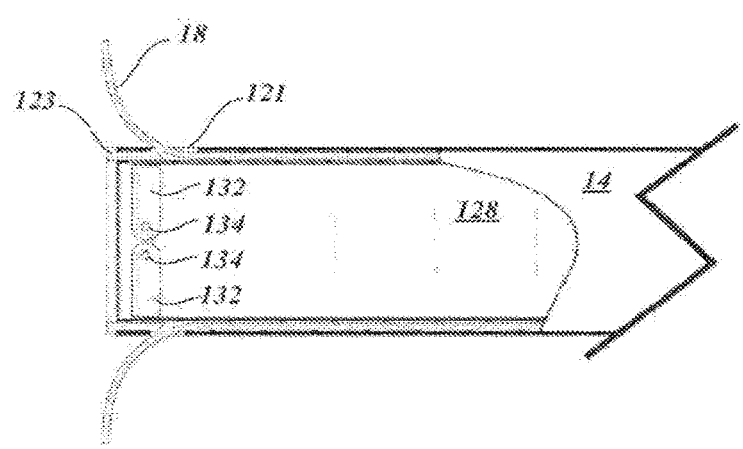
FIGS. 16A-16C schematically depict structure and deployment operations of the perpendicular double blade double axis specimen chamber 128.
Figure 16B:
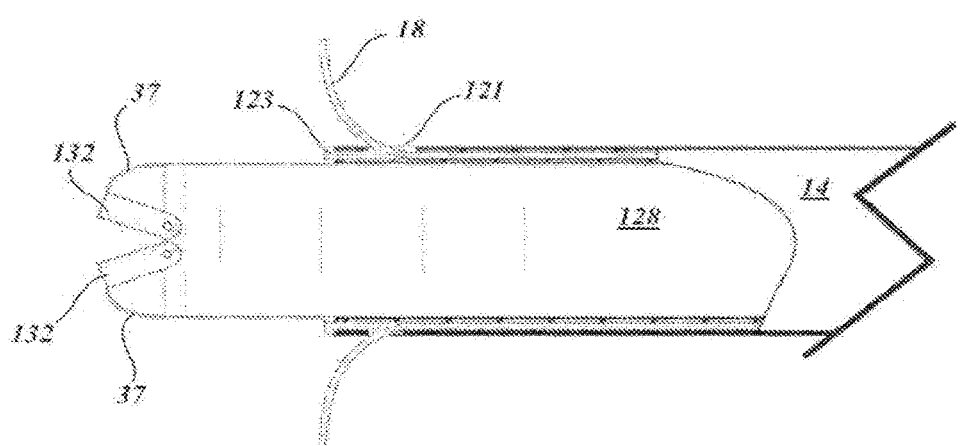
Figure 16C:
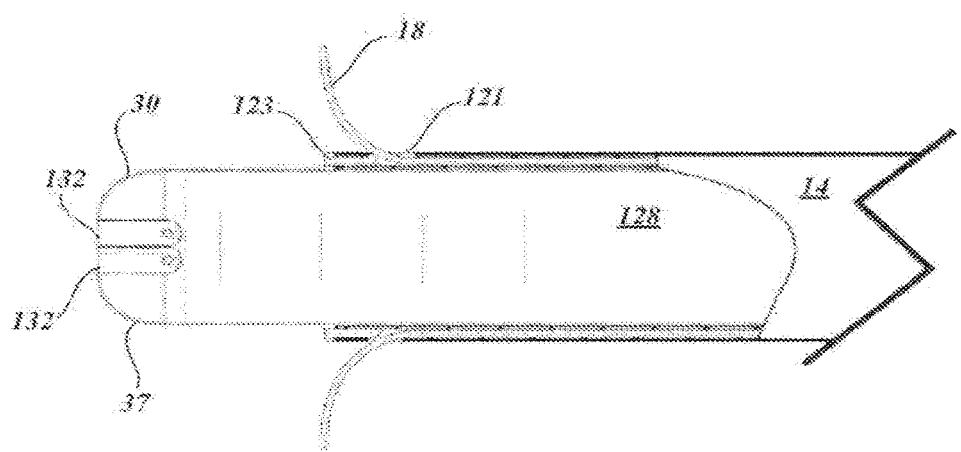

FIGS. 16A-16C schematically depict structure and deployment operations of the perpendicular double blade double axis specimen chamber 128. Presented in FIG. 16A are two rotatable cutting edges or blades 132 pivotable about their own axis 134. Each blade 132 counter-rotates relative to the other. The edge of the moveable blades 132 are the forward facing cutting surfaces of the specimen chamber 128. In the stowed position, both rotatable cutting edges 132 are perpendicular relative to the long axis of the specimen chamber 128. The blades 132 are rotatable about their own axis pivot 134. Depth stops 18 are similarly deployed through sheath apertures 121 via deflector posts 123.

In FIG. 16B, the specimen chamber 128 is shown deployed to the terminus of the sheath 14. The arcs of the blades 132 are approaching midway deployment via blade control wires 37.

In FIG. 16C, the specimen chamber 128 is shown deployed and the cutting action completed with the knives 132 abutting against each other to complete specimen severing.

Figure 17A:
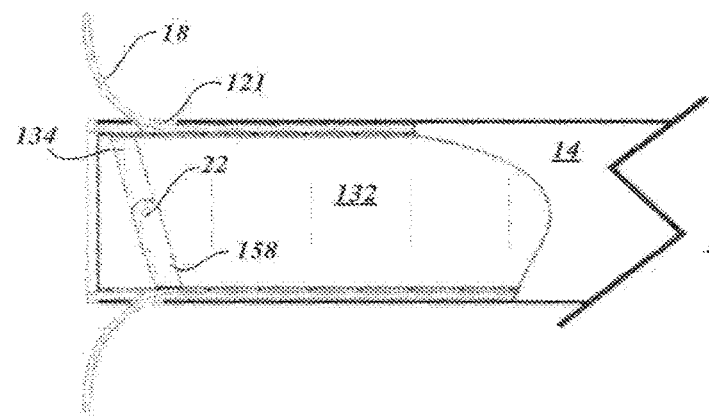
FIGS. 17A-17E schematically depict structure and deployment operations of the angled double blade single axis specimen chamber 132.

FIGS. 17A-17E schematically depict structure and deployment operations of the angled double blade single axis specimen chamber 132. Presented in FIG. 17A are two counter rotatable cutting edges or blades, a smaller blade 134 and a larger blade 138, each counter rotatable to the other via pivot or axis 22. The larger blade 138 counter-rotates relative to the smaller blade 134 until cutting action is completed when larger blade 138 overlaps smaller blade 134. The edge of the moveable blades 134 and 138 are the forward facing cutting surfaces of the specimen chamber 132. In the stowed position, both counter rotatable cutting edges 134 and 138 are angled or beveled relative to the long axis of the specimen chamber 132. The blades 134 and 138 are rotatable about the common pivot 22 they share. Depth stops 18 are similarly deployed through sheath apertures 121 via deflector posts 123.

Figure 17B:
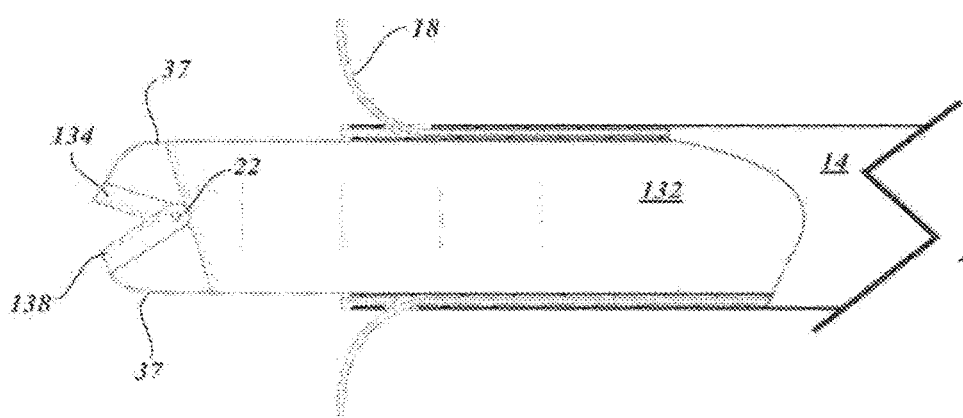
Figure 17C:
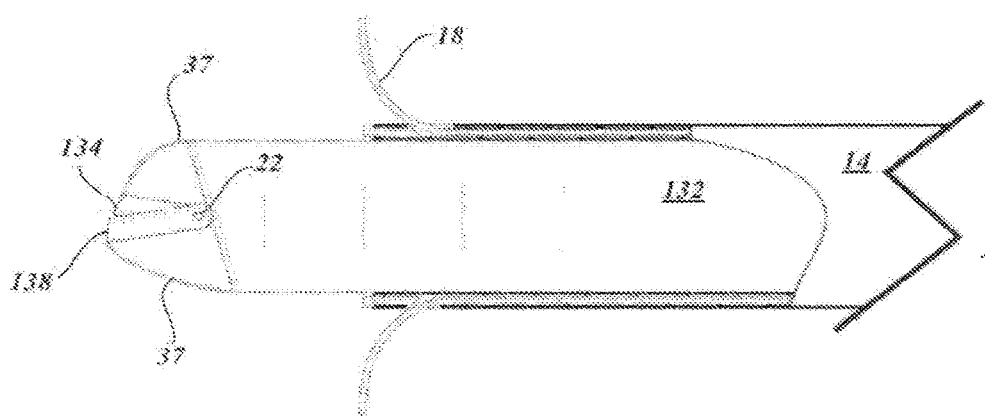
Figure 17D:
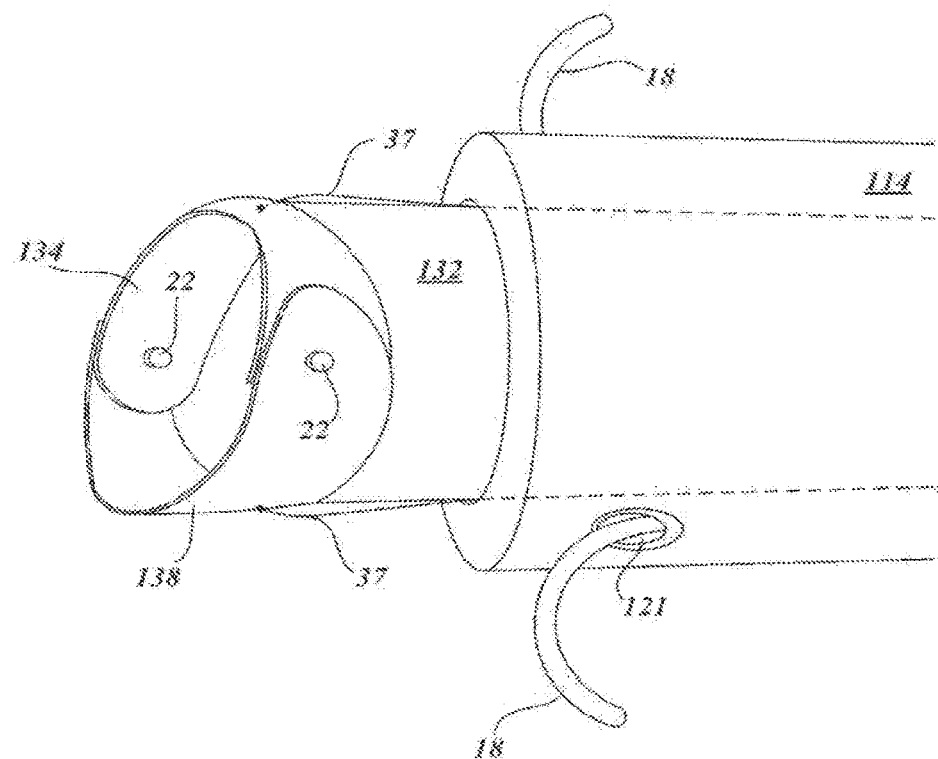
Figure 17E:
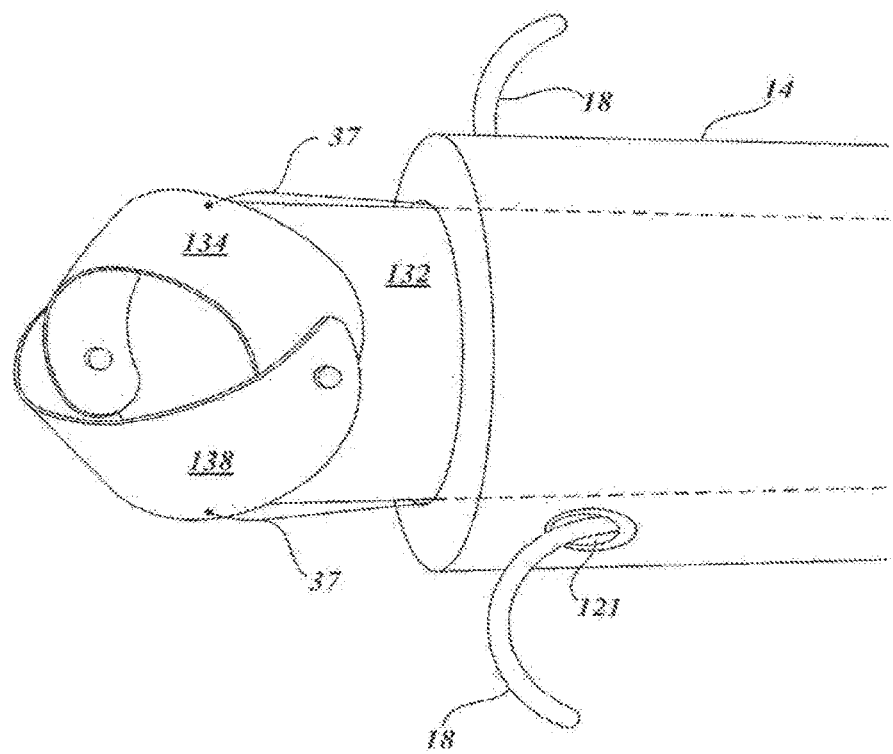

In FIGS. 17B and 17E, the specimen chamber 132 is shown deployed from the terminus of the sheath 14. The arcs of the blades 134 and 138 are approaching midway deployment via blade control wires 37.

In FIG. 17C, the specimen chamber 128 is shown deployed and the cutting action completed with the larger blade 138 overlapping the smaller blade 134 to complete specimen severing.

FIGS. 17E-17F depicts in perspective view the advancement of the specimen chamber 132 advanced from the terminus of the sheath 14. In FIG. 17D the blades 134 and 138 are stowed, have an angled configuration relative to the long axis of chamber 132, and ready for plunging into an anatomical region. In FIG. 17E the small and larger blades 134 and 138 are midway deployed during cutting action. More easily seen are the common pivots 22 to which small and large blades 134 and 138 rotate and the sheath apertures 121 from which the depth stops 18 emerge.

Figure 18A:
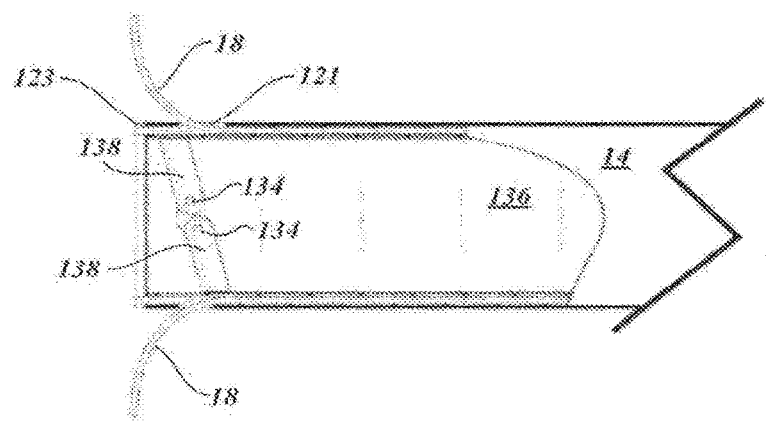
FIGS. 18A-18C schematically depict structure and deployment operations of the angled double blade double axis specimen chamber 136.
Figure 18B:
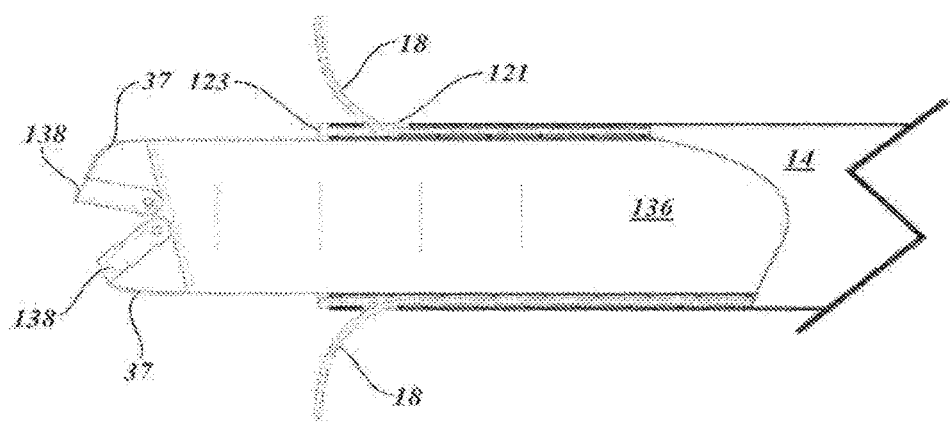
Figure 18C:
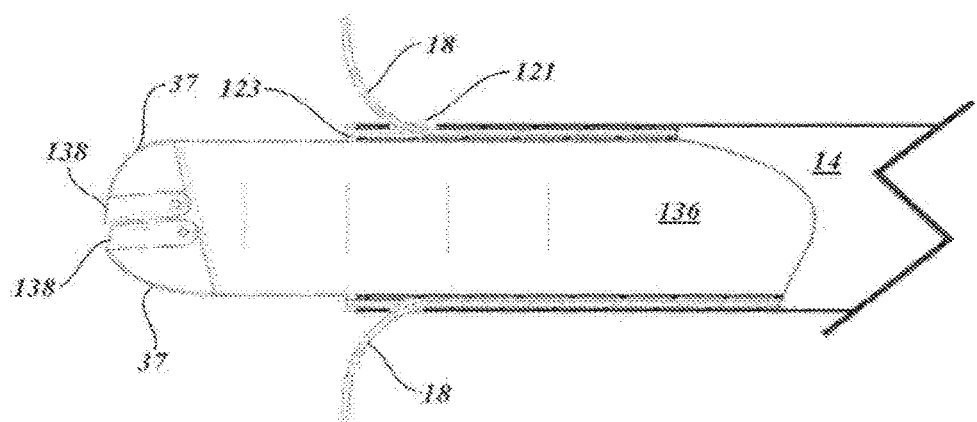

FIGS. 18A-18C schematically depicts structure and deployment operations of the angled double blade double axis specimen chamber 136. Presented in FIG. 18A are two counter rotatable cutting edges or blades 138 of substantially equal length in a stowed state that provide the forward facing cutting edges in an angled or beveled configuration relative to the long axis of the specimen chamber 136. Depth stops 18 are similarly deployed through sheath apertures 121 via deflector posts 123.

In FIG. 18B, the specimen chamber 136 is shown deployed from the terminus of the sheath 14. The blades 138 are rotatable about their own axis pivot 134. The arcs of the blades 138 are approaching midway deployment via blade control wires 37. One blade 138, being higher than the other blade 138, provides the larger cutting arc in FIG. 18C, the specimen chamber 136 is shown deployed and the cutting action completed with the higher positioned blade 138 abutting against the lower positioned blade 138 to complete specimen severing.

FIGS. 19A-19D schematically depict in perspective and top views alternative embodiments of depth stops 18 configurations deployed from the sheath 14 housing the perpendicular single blade 20 single axis specimen chamber 16. Perspective views show a partially deployed blade 20 and that specimen chamber 16 is shown advanced beyond the terminal end of the sheath 14. Top views do not illustrate partially deployed blade 20 but do illustrate positioning of deployed depth stops 181118 in relation to sheath 14 and specimen chamber 16. The alternate configurations provide for more contact points to secure levels of footing to deploy plunging operations of the advanced specimen chamber 16.

FIG. 19A illustrates two deployed depth stops 18, one clearly seen to emerge from sheath aperture 121. The depth stops 18 are diagonally positioned relative to each other, that is, about 120 degrees apart from the center of the chamber lumen 125 and provide for a two-legged stand from which to engage plunging of the deployed specimen chamber 16.

FIG. 19B illustrates three deployed depth stops 18, two clearly seen to emerge from sheath apertures 121. The depth stops 18 are about 120 degrees apart from each other relative to the center of the chamber lumen 125 and provide a tripod-like stability from which to engage plunging of the deployed specimen chamber 16.

FIG. 19C illustrates four deployed depth stops 18, two clearly seen to emerge from sheath apertures 121. The depth stops 18 are about 90 degrees apart from each other relative to the center of the chamber lumen 125 and provide for a four-legged stand from which to engage plunging of the deployed specimen chamber 16.

FIG. 19D illustrates two deployed depth stop loops 118, the loops deployed from the sheath apertures 121. The stop loops 118 are deployed across from each other and provide for additional stability from which to engage plunging of the deployed specimen chamber 16.

Figure 20A:
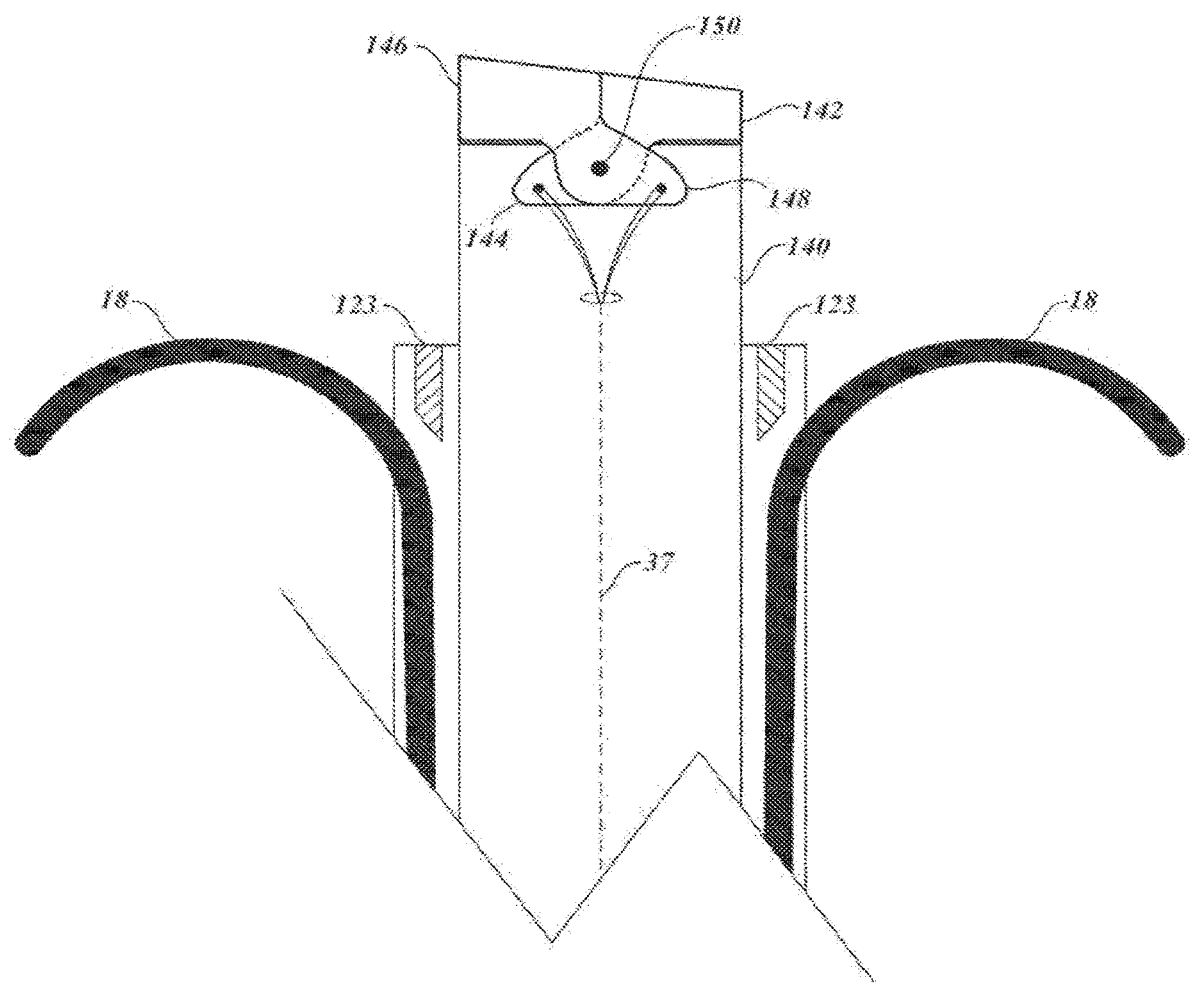
FIGS. 20A-20B schematically depict structure and deployment operations of the angled double cantilevered blade single axis specimen chamber 140.
Figure 20B:
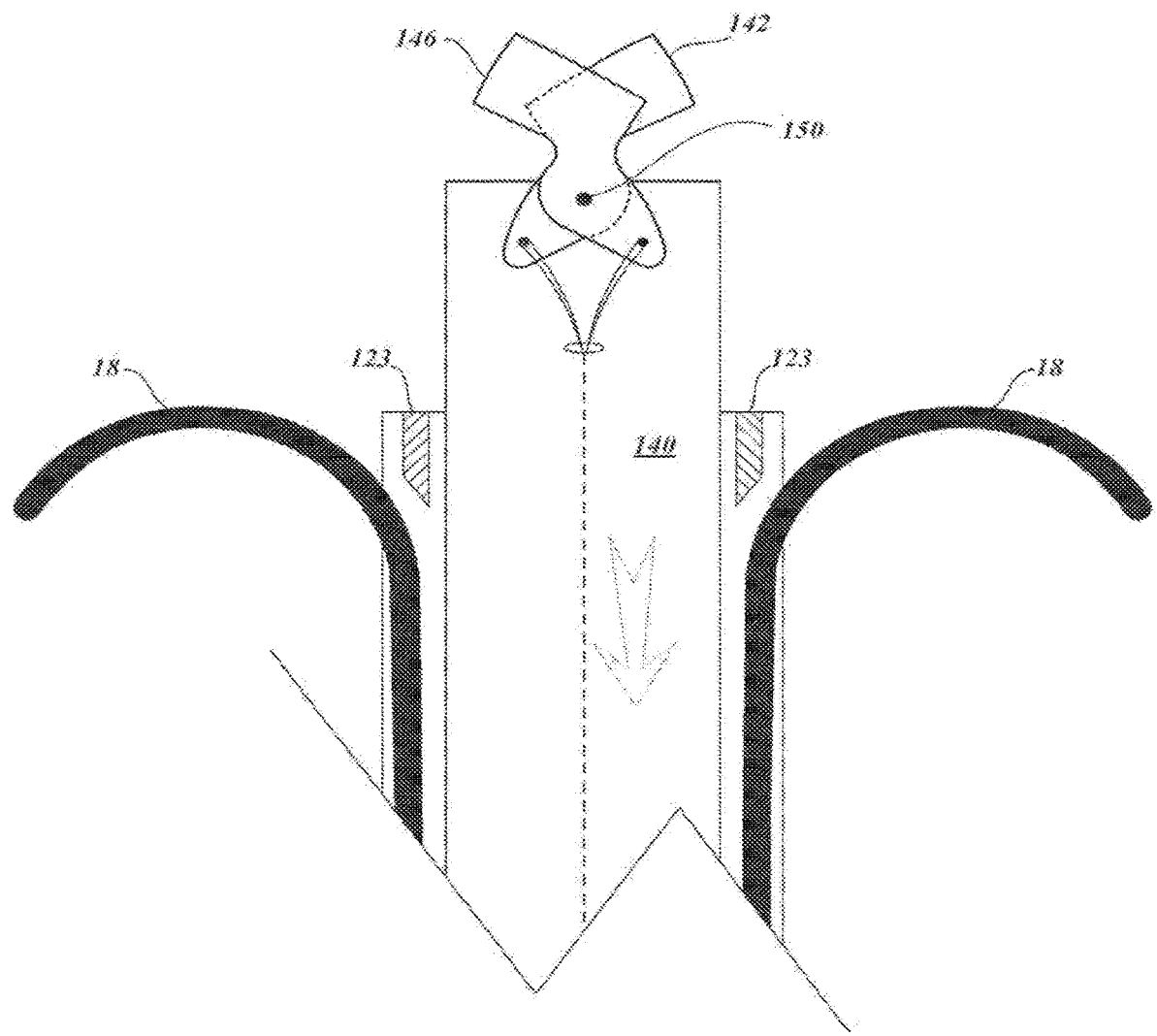

FIGS. 20A-20B schematically depicts structure and deployment operations of the angled double cantilevered blade single axis specimen chamber 140.

FIG. 20A presents the cantilevered specimen chamber 140 configured with two cutting blades in an angled configuration, a small cutting blade 142 with a lever projection 144, and a larger cutting blade 146 with a lever projection 148. Each blade 142/146 rotates about pivot axis 150 shared between them. Blade control wires 37 connects to lever projections 144 and 148. Depth stops 18 are shown deployed.

FIG. 20B presents deployment of small blade 142 and large blade 146 of the cantilevered specimen chamber 140. A downward pulling action conveyed by the blade control wires 37 initiated by the downward action applied by the operator to thumbhole 66 of multifunction handle 50 shown in FIG. 2 engages rotation of small blade 142 and large blade 146, each counter-rotating relative to the other to commence cutting action. The blades 1421146 are returned to the stowed position by a pulling action applied to the thumbhole 66 by the user operating the handle 50.

FIGS. 21A-21G schematically depicts structure and deployment operations of the perpendicular double cantilevered blade single axis specimen chamber 160.

Figure 21A:
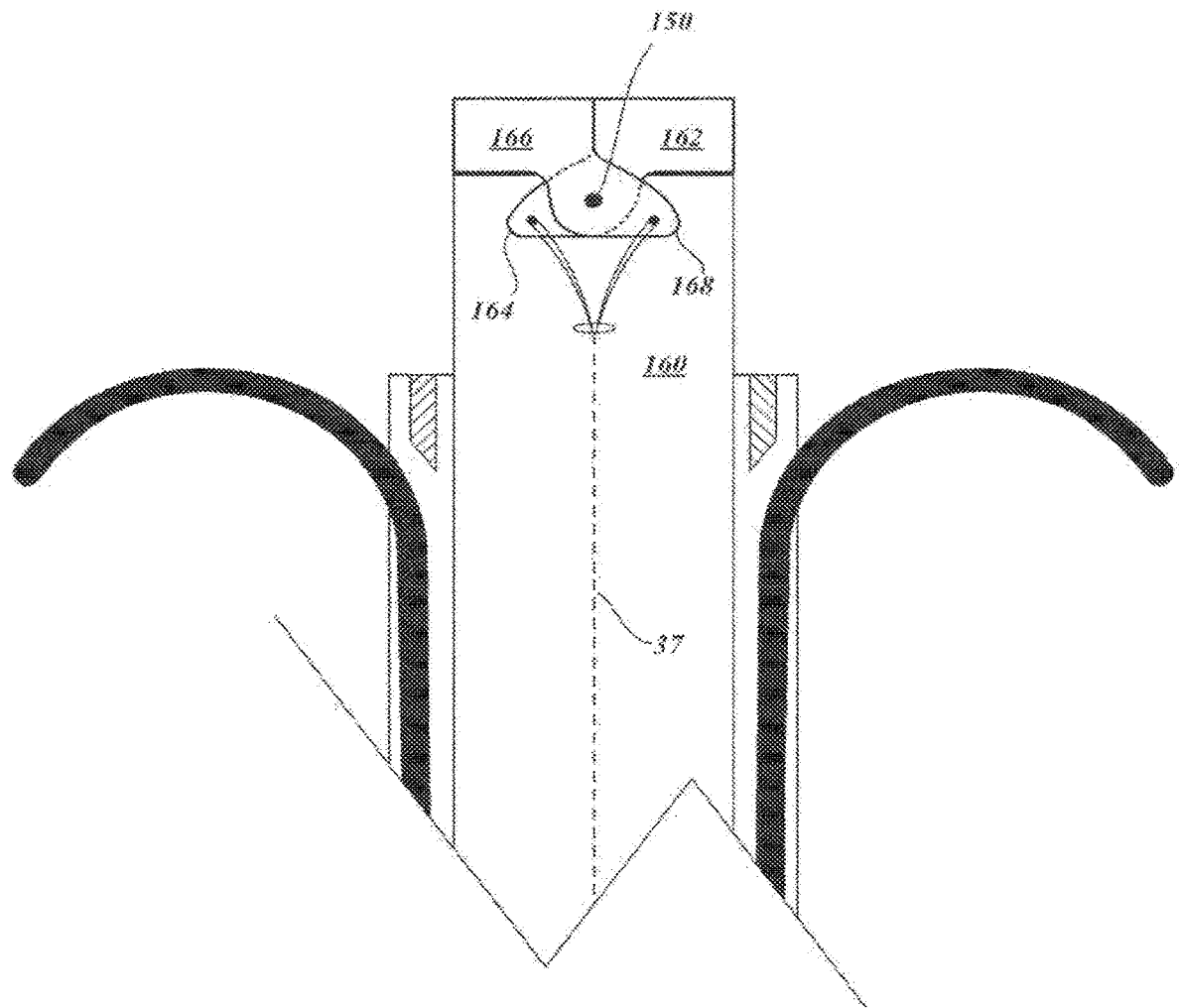

FIG. 21A presents the cantilevered specimen chamber 160 configured with two cutting blades in a perpendicular configuration, a small cutting blade 162 with a lever projection 164, and a larger cutting blade 166 with a lever projection 168. Each blade 1621166 rotates about pivot axis 150 shared between them. Blade control wires 37 connects to lever projections 164 and 168. Depth stops 18 are shown deployed.

FIGS. 21B-D schematically depicts perspective views of cutting action, retraction, and stowage of the blades 162/ 166. Presented in FIG. 21B, a downward applied pulling action applied by the operator to thumbhole 66 of multifunction handle 50 shown in FIG. 2 engages rotation of the blades 162/166 to their completed, cutting state, with the smaller blade 162 enveloped within the larger blade 166. When a pulling force is applied to the thumbhole 66 of handle 50 as shown in FIGS. 21E and D, the blade control wires move upward to retract the blades 162/166 to the stowed state.

FIGS. 21E-G schematically depicts side views of specimen sample procurement from completion of cutting action, retraction, and stowage of the blades 162/166. Depth stops 18 are deployed. Specimens of histological quality 170 are housed within the lumen of specimen chamber 160. Presented in FIG. 21E a downward applied pulling action applied by the operator to thumbhole 66 of multifunction handle 50 shown in FIG. 2 engages rotation of the blades 1621166 to their completed, cutting state to severe a histological grade specimen devoid of crush artifacts. As shown in FIGS. 21F and G, when a pushing force is applied to the thumbhole 66 of handle 50 the blade control wires 37 move upward to retract the blades 1621166 to the stowed state.

Figure 22:
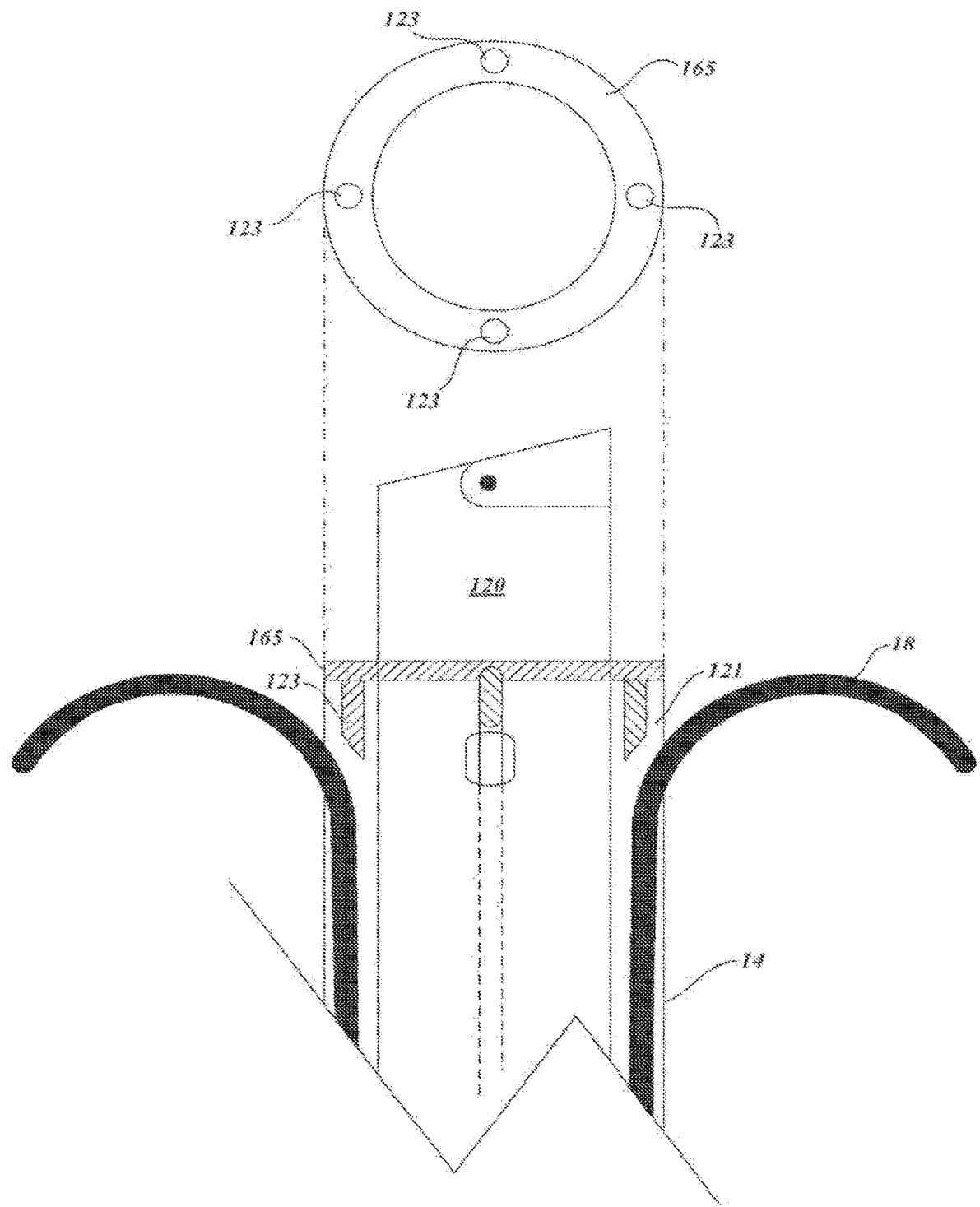
FIG. 22 schematically depicts structure and deployment operations of the angled single blade single axis specimen chamber 120 with wire deflection cap 165.

FIG. 22 schematically depict structure and deployment operations of the angled single blade single axis specimen chamber 120 with depth stop deflection cap 165. Depth stop deflection cap 165 may be inserted into the sheath 14 such that deflectors 123 are aligned with sheath apertures 121.

Figure 23A:
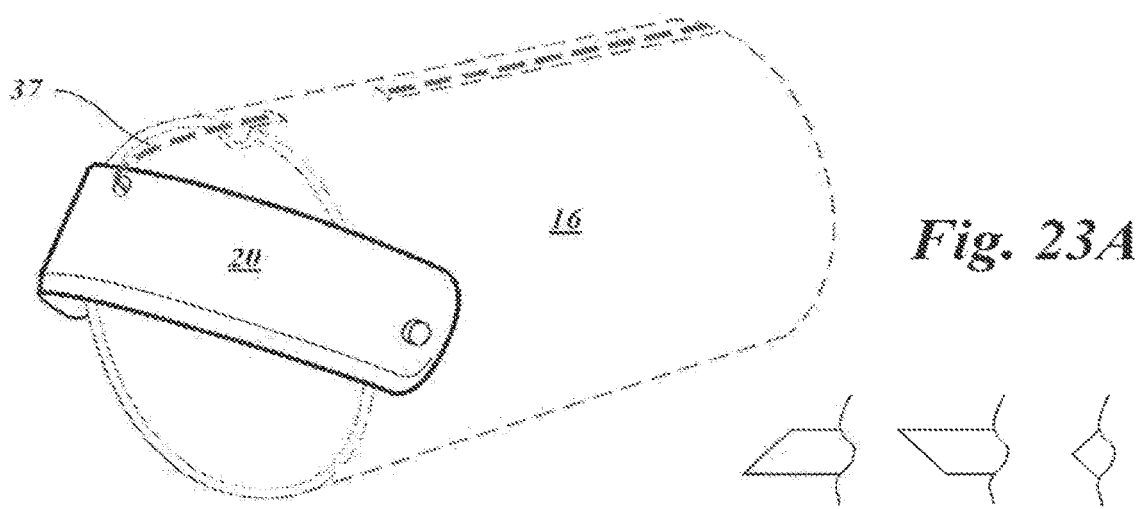
FIGS. 23A-23C schematically depicts alternate configurations of blade cutting surfaces.
Figure 23B:
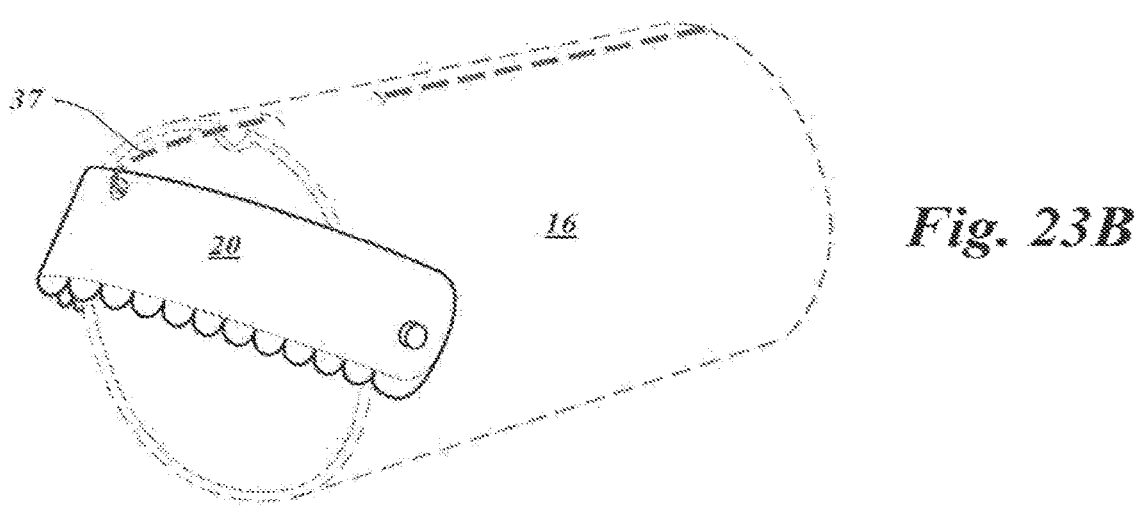
Figure 23C:
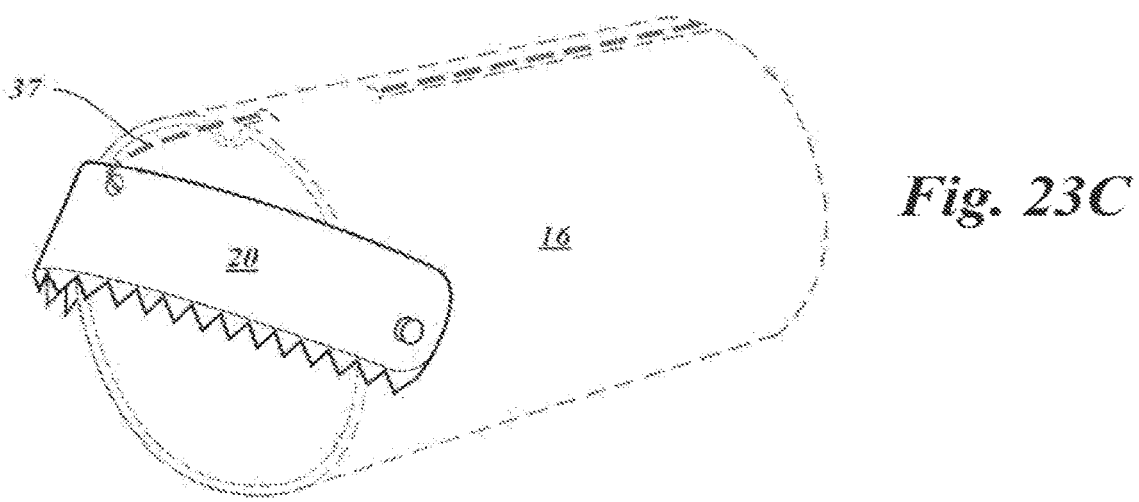

FIGS. 23A-23C schematically depicts alternate configurations of blade cutting surfaces. FIG. 23A shows a single edge razor configuration facing internally (per left inset) and curved with the semi-circular blade 20 pivoting about the forward face of specimen chamber 16. In other embodiments, as shown in the middle inset of FIG. 23A, the single edge razor may face outward, that is the razor sharp edge may be occupy the largest external arc of the blade 20, external such that the razor's edge is at the maximum arc. Or, alternatively, the razor may be double edge shown in the right inset where the razor's edge occupies the middle of the blade 20. FIG. 23B illustrates a serrated configuration, and FIG. 23C a toothed configuration. The serrated and tooth configurations may also have an internal razor's edge, internal razor's edge, or double edged where the razor's edge is in the middle of the blade.

Figure 24A:
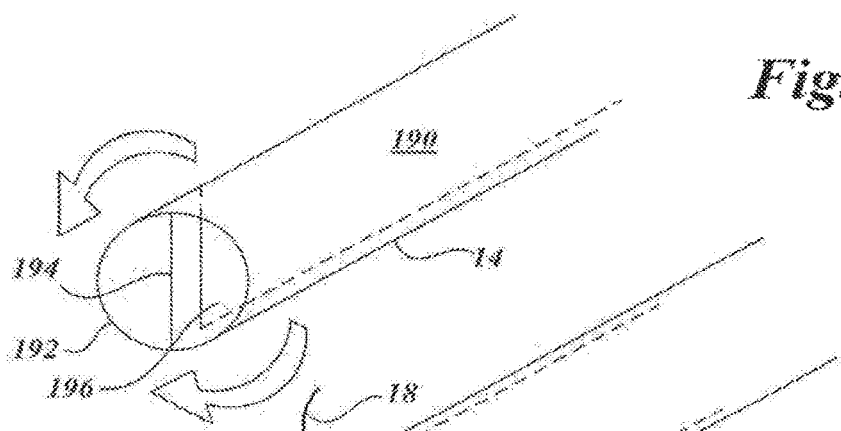
FIGS. 24A-24E schematically depicts structure and deployment operations of a rotary cutting specimen chamber 190.
Figure 24B:
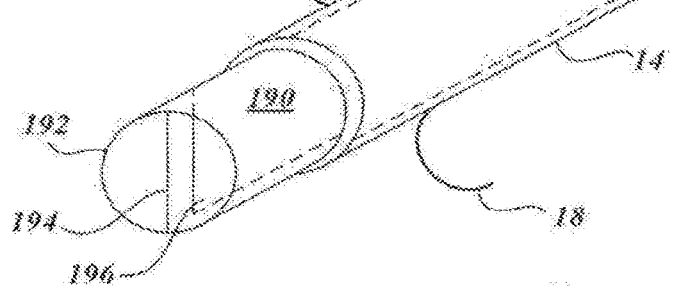

FIGS. 24A-24E schematically depicts structure and deployment operations of a rotary cutting specimen chamber 190. In FIG. 24A the specimen chamber 190 is plunged into the target tissue to effect cutting via cutting edge or cutting circumference 192. Specimen chamber 190 is then rotated and counter rotated to effect cutting with cutting wire 194 spanning across the middle of the forward presenting lumen face of specimen chamber 190. In FIG. 24B, upon plunging into tissue limited by the depth set by depth stops 18, the cutting wire bisects the tissue specimen equally into two halves. Each half of the tissue specimen is kept separated by tissue divider 196.

Figure 24C:
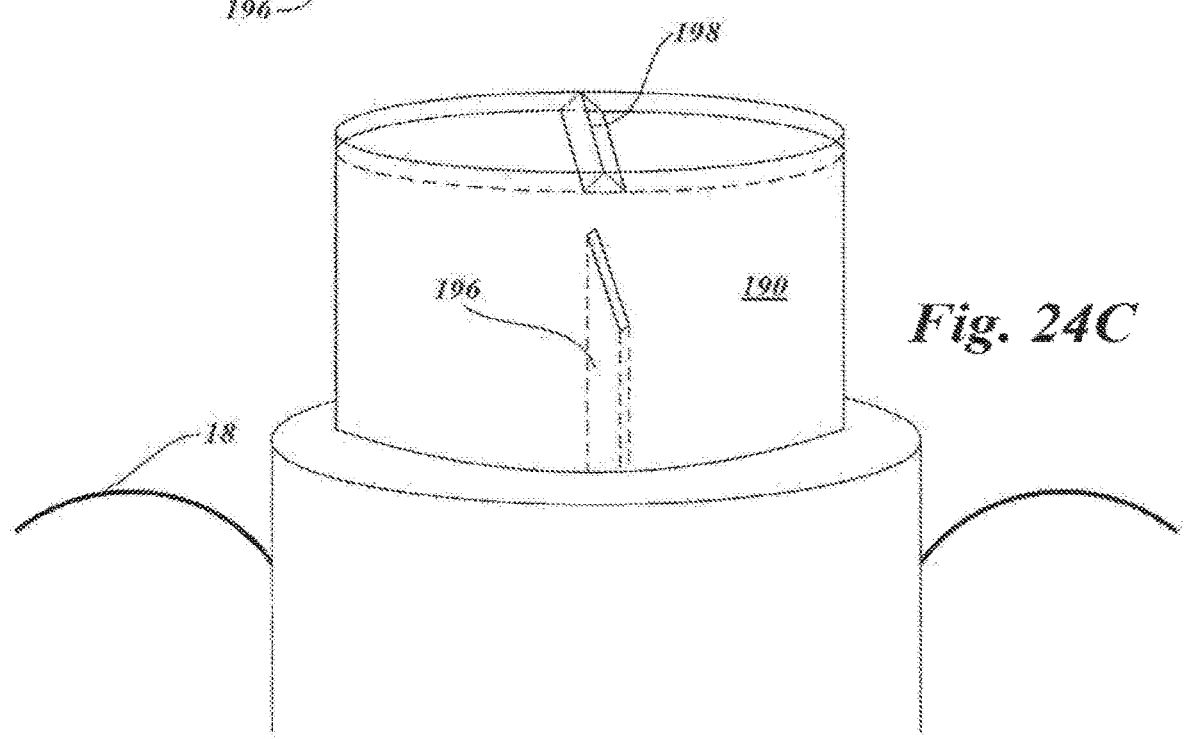

FIG. 24C depicts a perspective view of the specimen chamber 190 with deployment of depth stops 18 from the sheath 14. In an alternate embodiment, the cutting wire 194 may be replaced with a cutting wedge 198. The specimen divider 196 similarly preserves the specimen halves, their tissue integrity, sampling order and orientation.

Figure 24D:
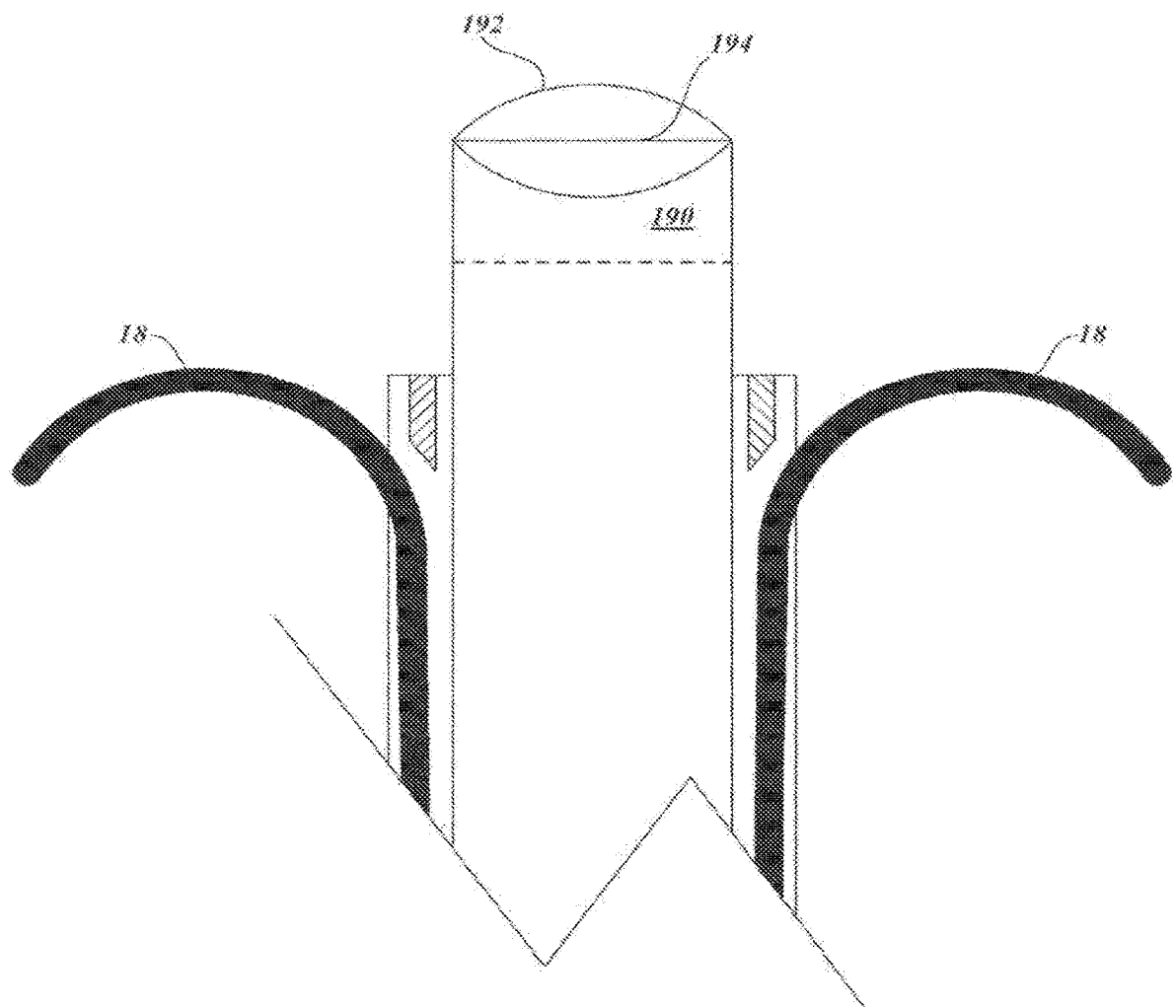
Figure 24E:
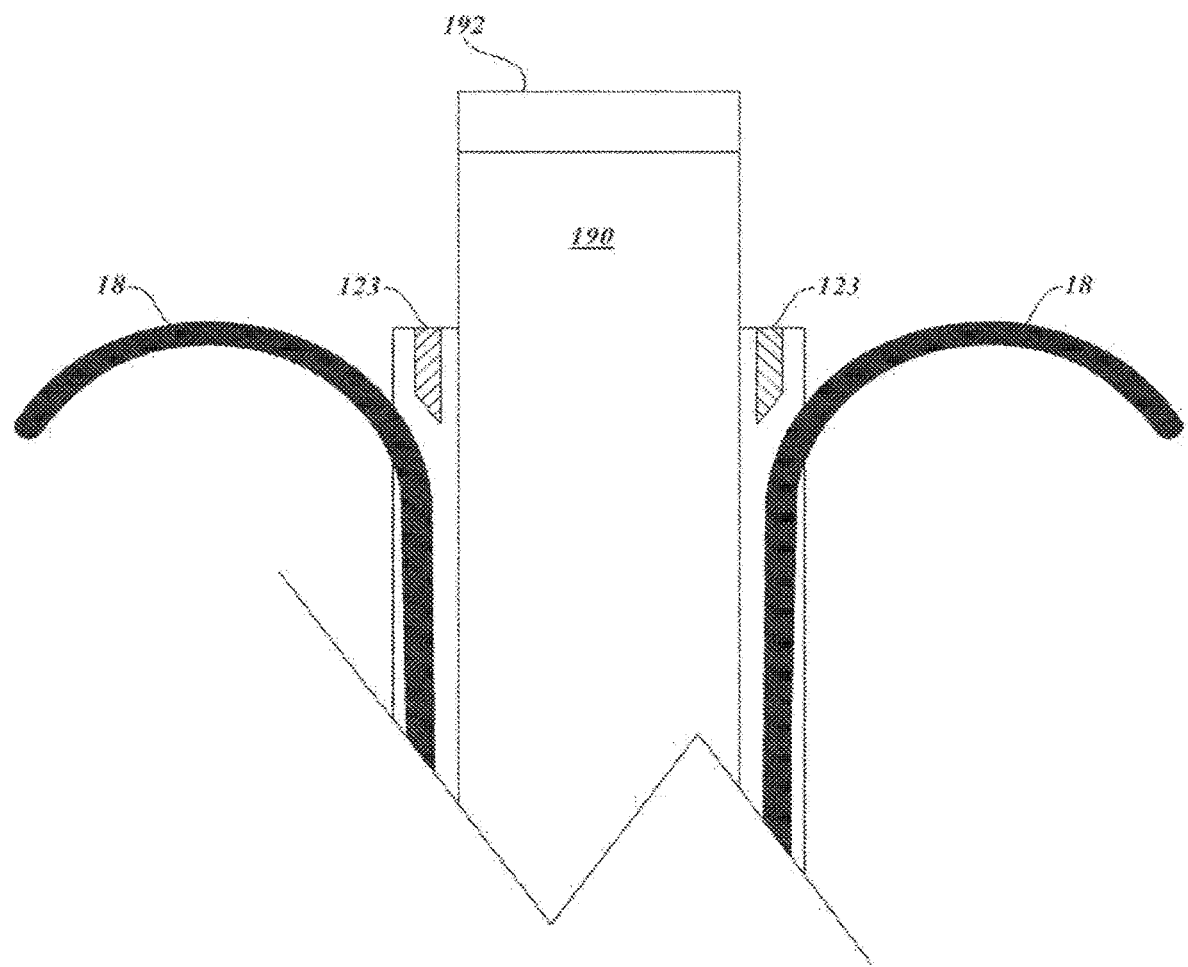

FIGS. 24D-E illustrate perspective and side views of the specimen chamber 190 with deployed depth stops 18.

FIGS. 25A-25F schematically depicts structure and deployment operations of the perpendicular double cantilevered blade single axis specimen chamber 188 in the sequential or consecutive acquisition of histological grade tissue specimens temporarily housed within the specimen chamber 188.

Presented in FIGS. 25A and 25B is the deployment of four depth stops 18. Top views show the depth stops retracted within sheath 14 in FIG. 25A and then deployed in FIG. 25B.

In FIG. 25C the specimen chamber 188 is deployed beyond the terminus of sheath 14, readied for plunging into tissue to procure a specimen.

FIG. 25D previously acquired specimens are pushed or displaced downward (wide, white motion arrows) upon thrusting or plunging action of the specimen chamber 188 into a tissue sampling site chosen by the operator indicated in FIGS. 7 and 10.

FIG. 25E illustrates commencement of cutting action by blades 162/166 when a downward motion to blade control wire 37 is effected by a pulling action applied by the operator to thumbhole 66 of multifunction handle 50 shown in FIG. 2 engages the mutual counter rotation of blades 162/166 via cable's 37 connection with lever projections 164/168 to a midpoint in blades 162/166 cutting action.

FIG. 25F illustrates completion of cutting action by blades 1621166 when the downward motion to blade control wire 37 is effected by completion of pushing force applied by the operator to thumbhole 66 of multifunction handle 50 shown in FIG. 2. The just cut specimen then may be displaced into the lumen of the specimen chamber 188 by retraction of the blades 1621166 to their stored state via a pulling force applied to the thumbhole 66 of multifunction handle 50 and then re-plunging the chamber 188 at another sample site depicted in FIG. 25D.

Figure 26:
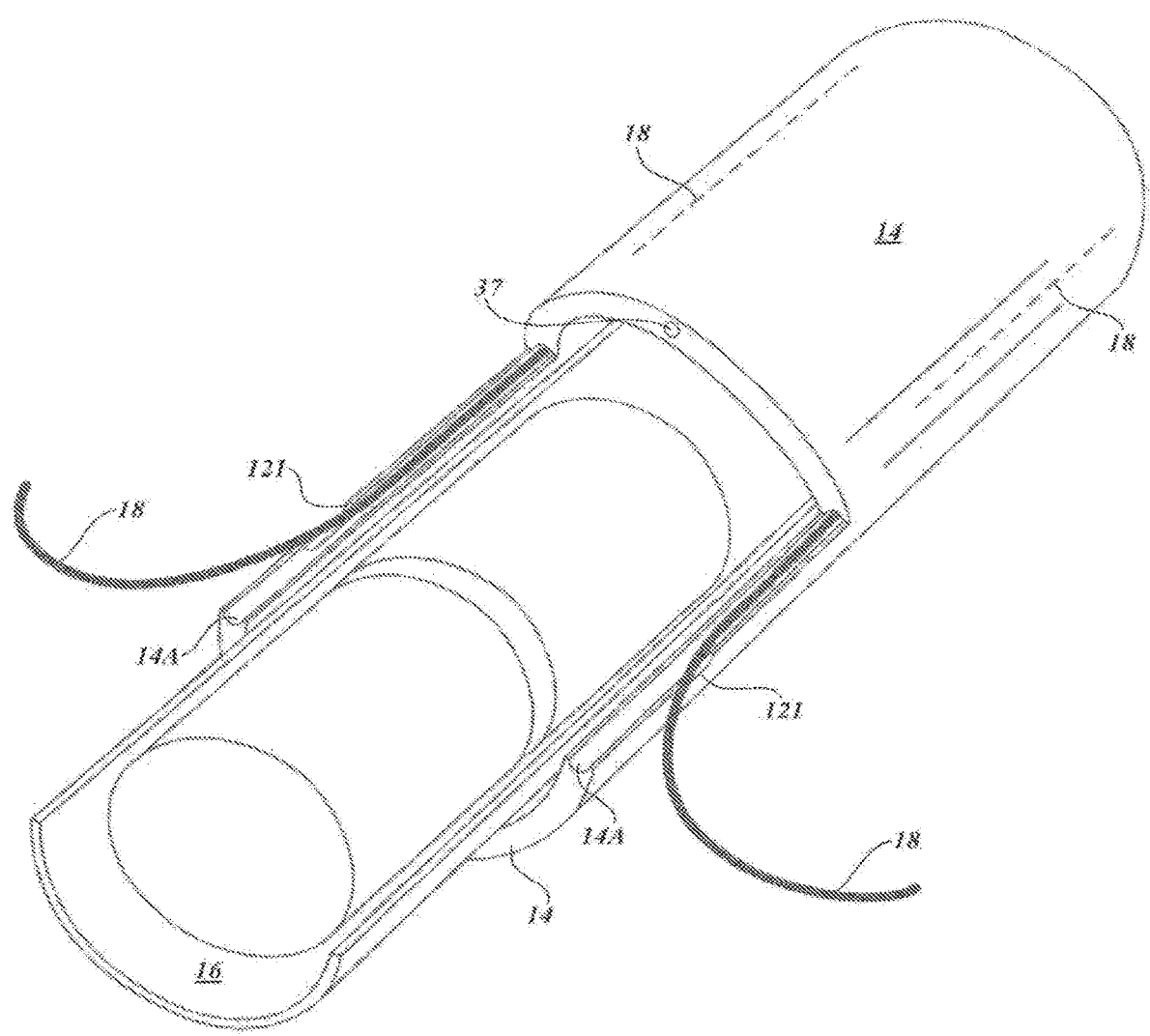
FIG. 26 presents a perspective view of the specimen chamber 16 in relation to the sheath 14.

FIG. 26 presents a perspective view of the specimen chamber 16 in relation to the sheath 14.

Figure 27:
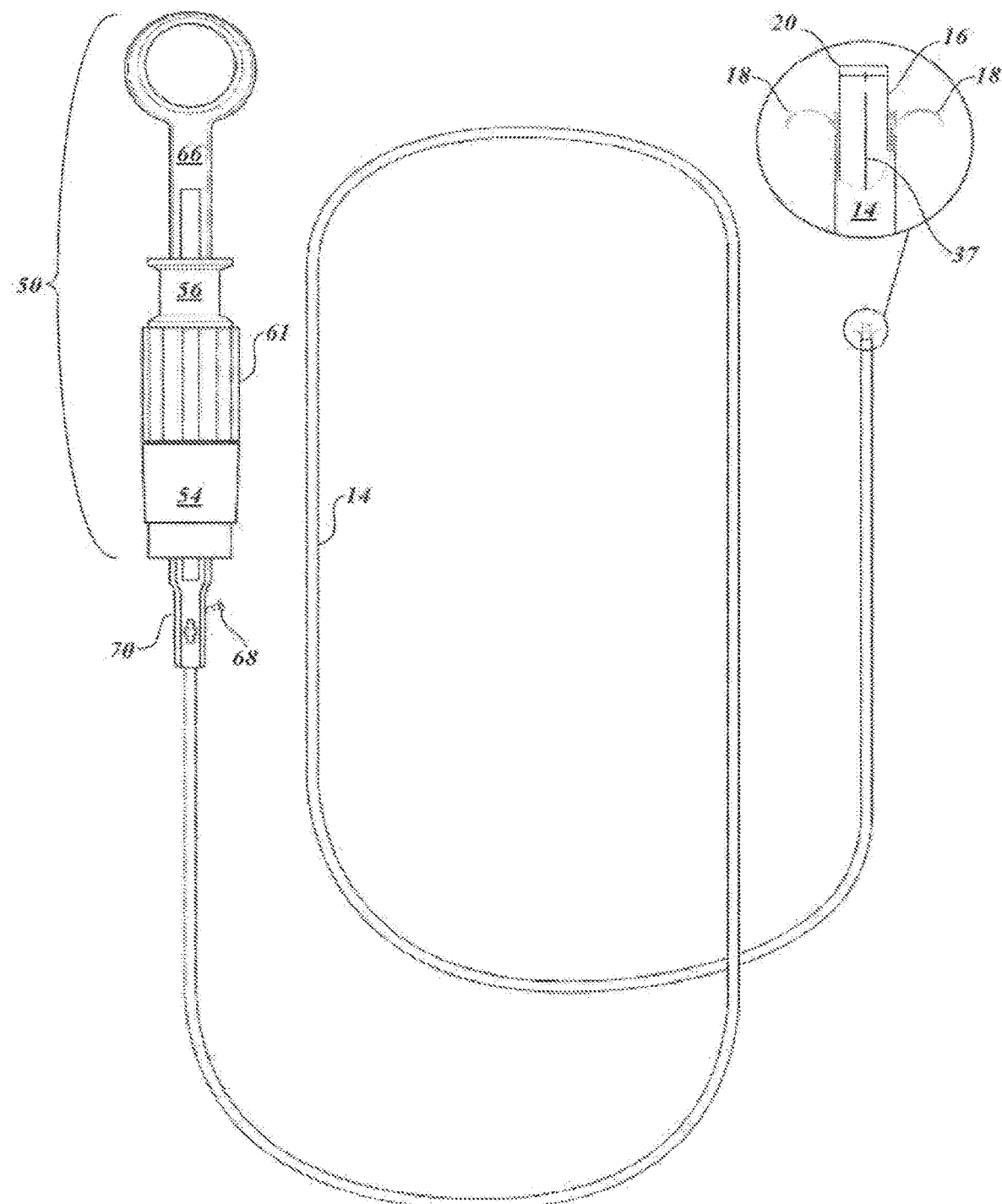
FIG. 27 presents an alternate embodiment depiction of the MCB device 10 depicted in FIG. 1.

FIG. 27 presents an alternate embodiment depiction of the MCB 10 depicted in FIG. 1.

Figure 28:
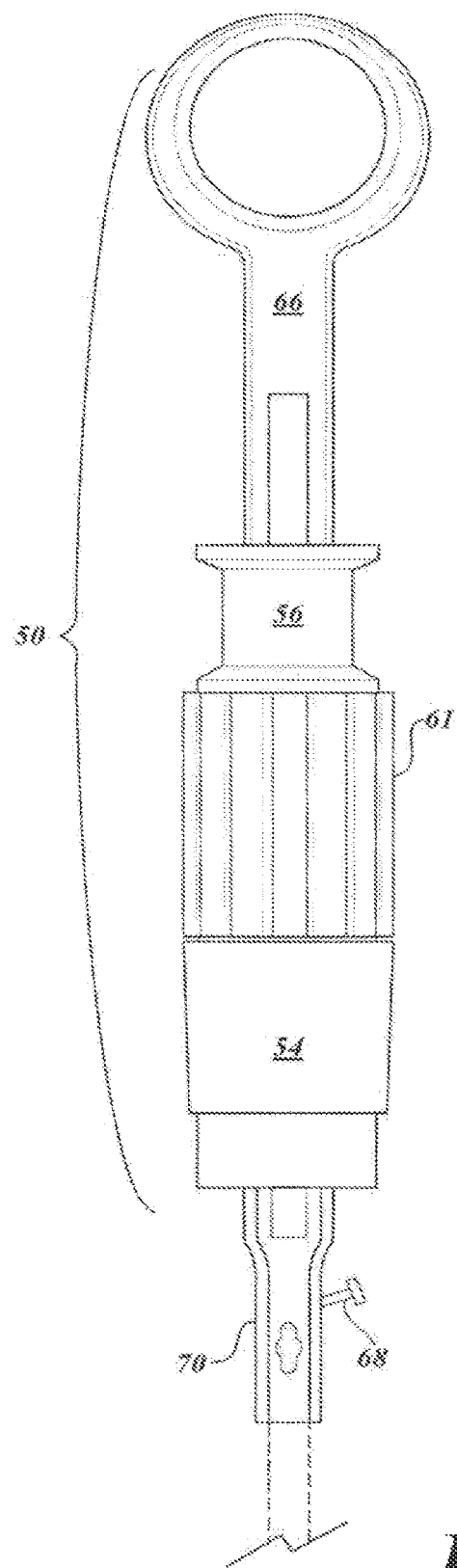
FIG. 28 presents a side view depiction of an alternate embodiment to the multifunction biopsy device handle 50 depicted in FIG. 2.

FIG. 28 presents a side view depiction of an alternate embodiment to the multifunction handle 50 depicted in FIG. 2.

Figure 29:
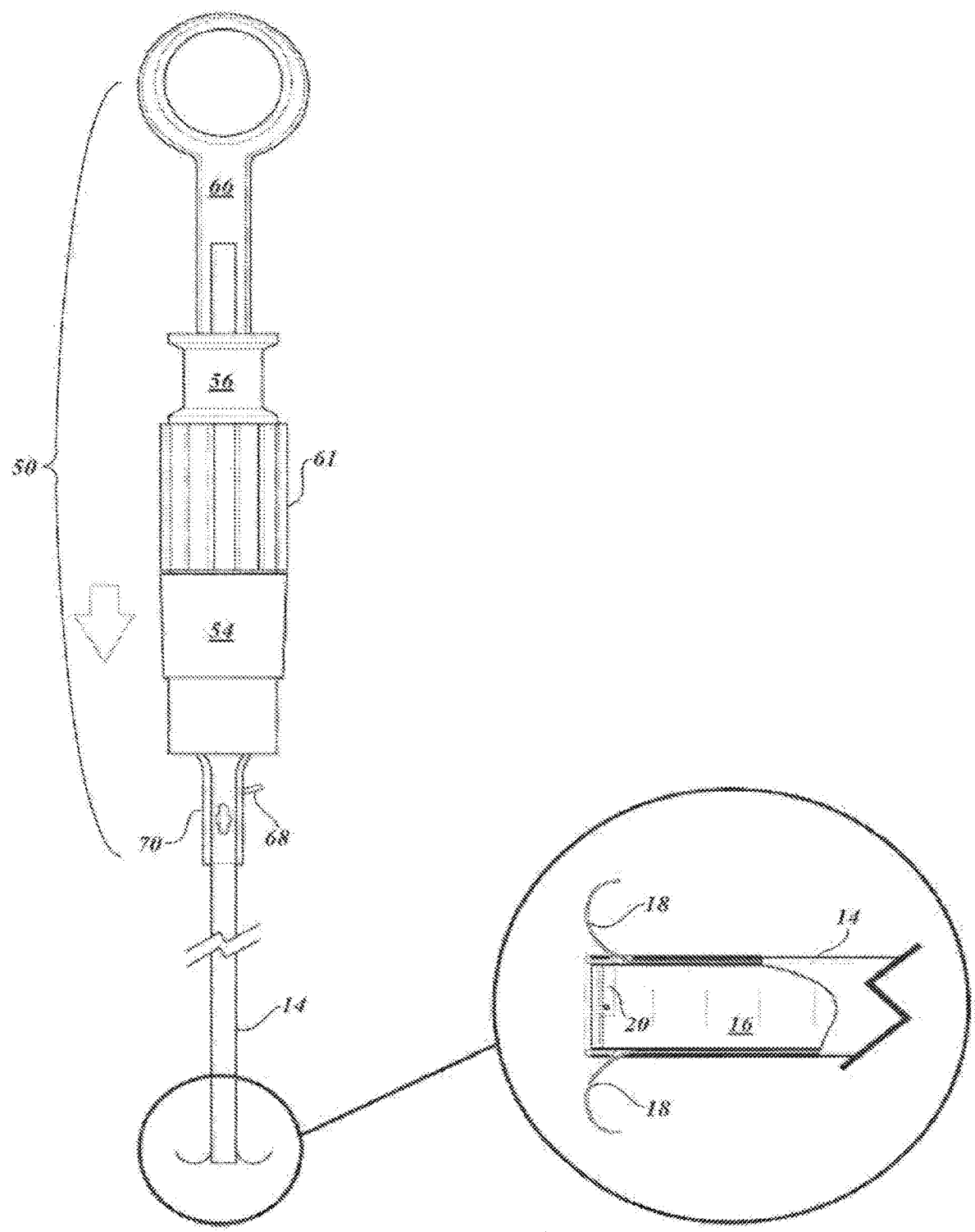
FIG. 29 presents another depiction of the depth stop 18 deployment from the MCB device 10 described in FIG. 11B.

FIG. 29 presents another depiction of the depth stop 18 deployment from the MCB 10 described in FIG. 12A.

Figure 30:
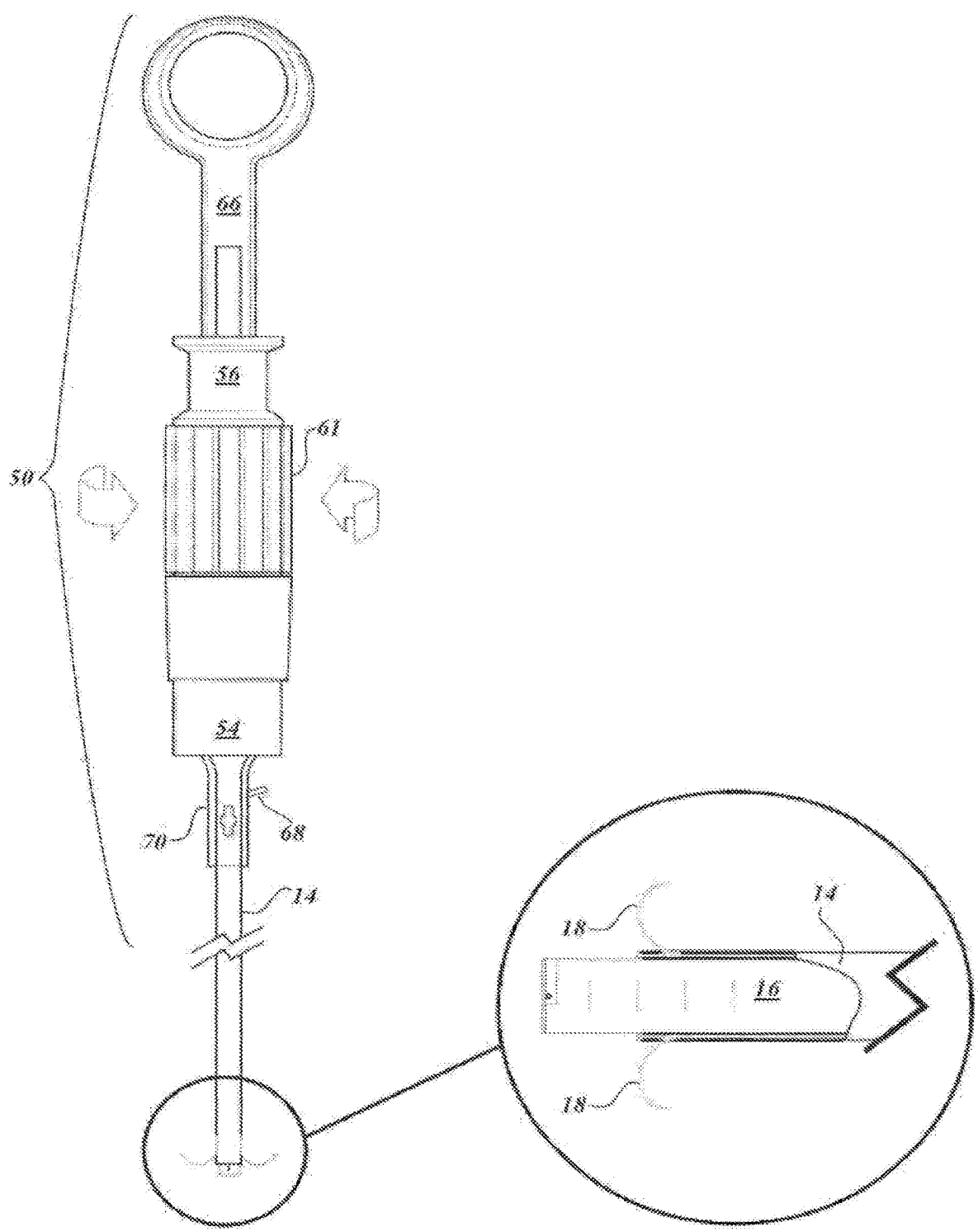
FIG. 30 presents another depiction of the setting of the specimen chamber's 16 plunging distance and advancement to that plunging distance from the MCB device 10 described in FIG. 12B.

FIG. 30 presents another depiction of the setting of the specimen chamber's 16 plunging distance and advancement to that plunging distance from the MCB 10 described in FIG. 12B.

Figure 31:
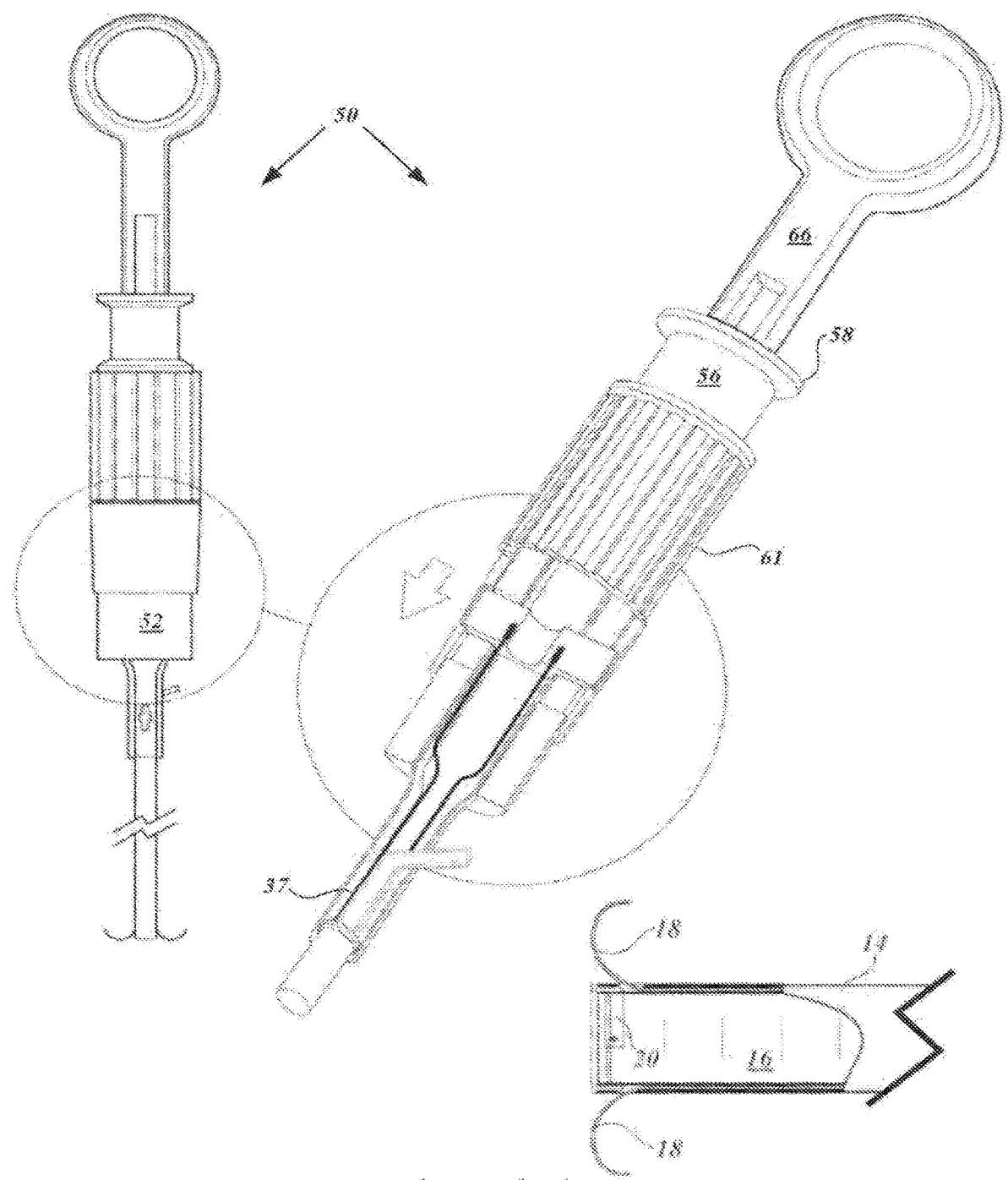
FIG. 31 presents another depiction of the deployment of the depth stops 18 from the MCB 10 described in FIG. 11B.

FIG. 31 presents another depiction of the initiation of cutting action by the blade 20 from specimen chamber 16 from the MCB 10 described in FIG. 12C.

Figure 32:
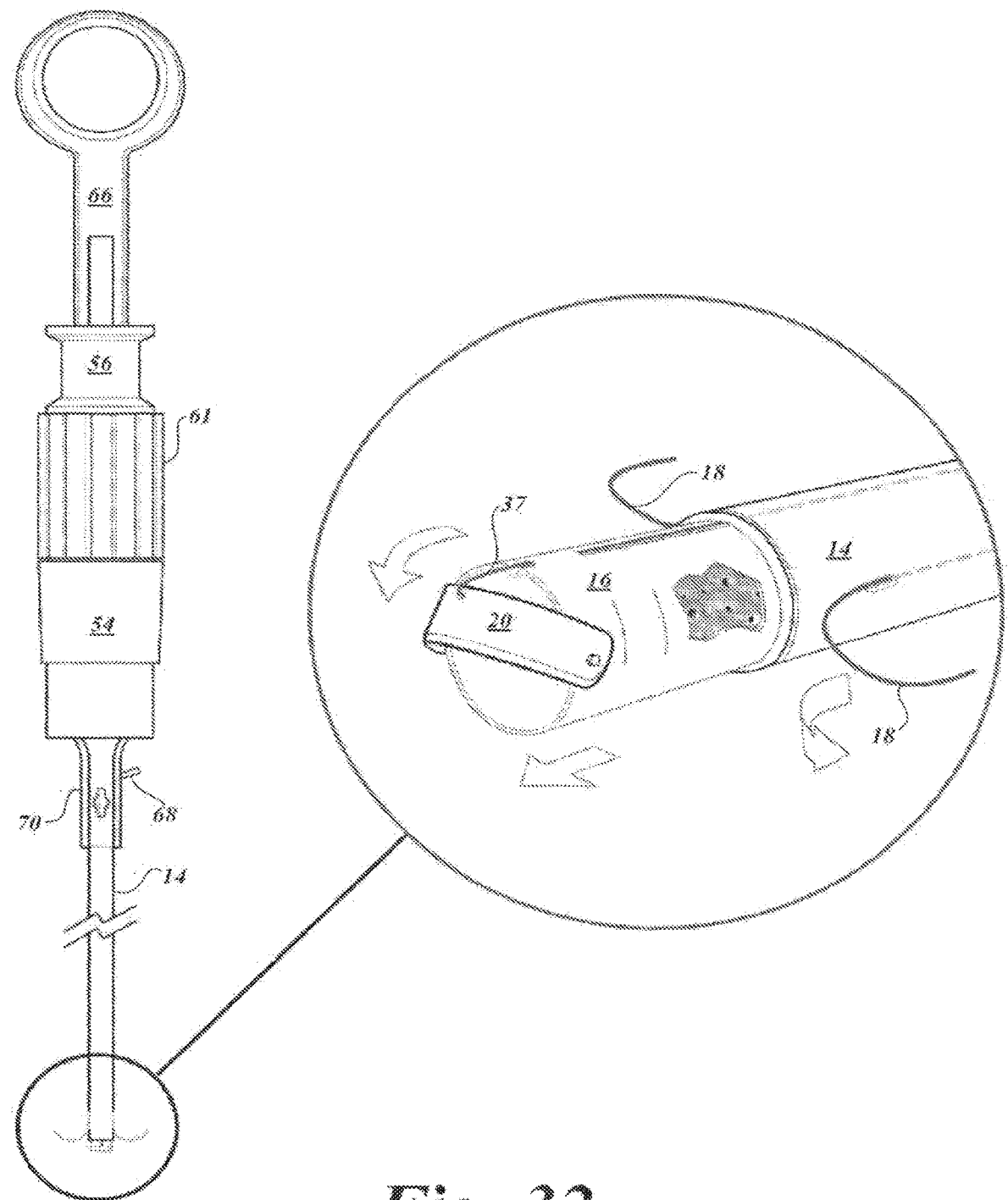
FIG. 32 presents another depiction of the cutting action by the blade 20 from specimen chamber 16 and storage of multiple tissue sections stored within the specimen chamber 16 from the MCB device 10 described in FIG. 12D.

FIG. 32 presents another depiction of the cutting action by the blade 20 from specimen chamber 16 and storage of multiple tissue sections stored within the specimen chamber 16 from the MCB 10 described in FIG. 12D.

FIG. 33 present alternate cross-sectional and perspective views depicting specimen chamber 188 deployment and blade operation shown in FIGS. 25A-F above.

FIG. 34 presents additional cross-sectional and perspective views specimen chamber 188 deployment and blade operation depicted in FIGS. 25A-F above.

Figure 35:
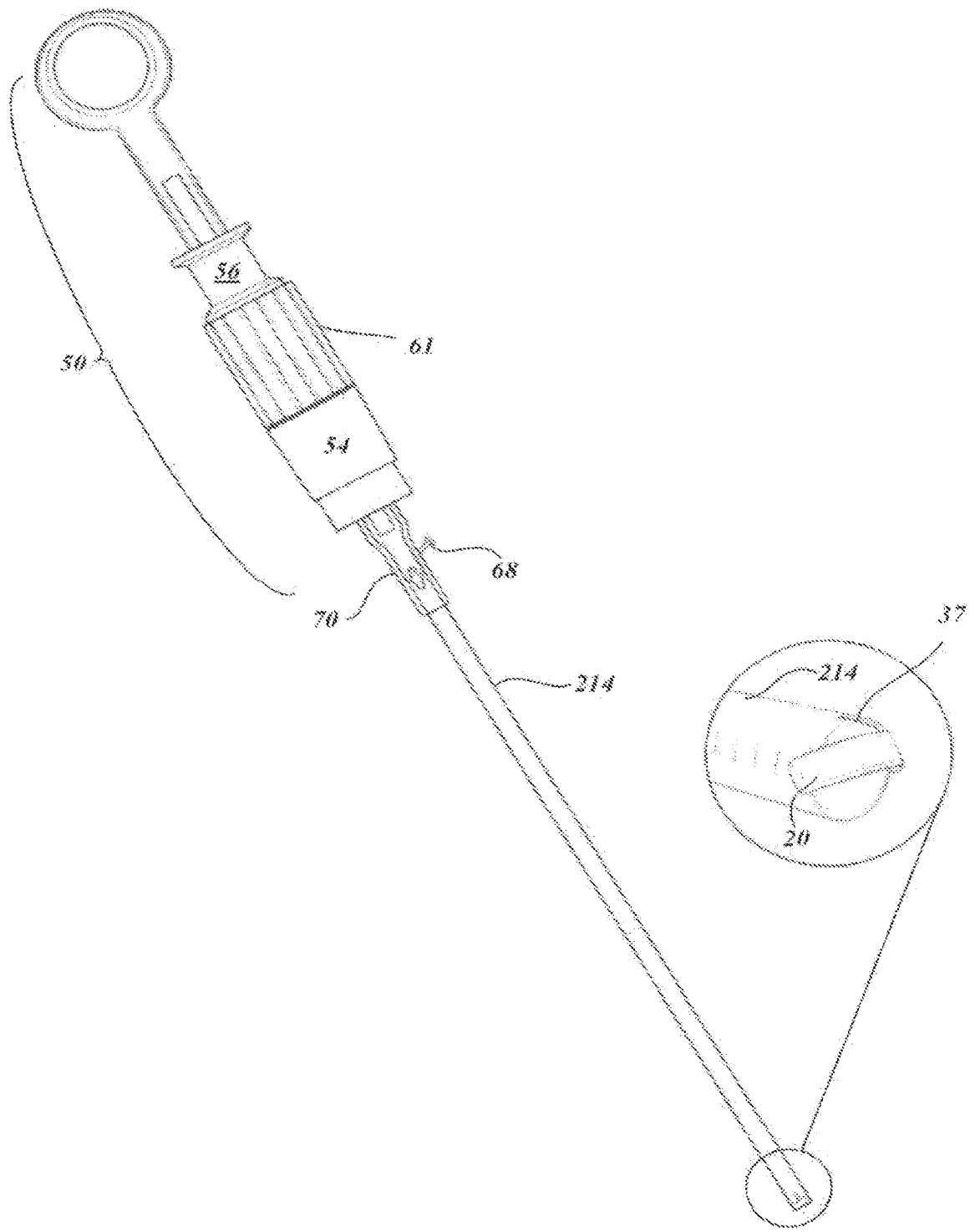
FIG. 35 presents another side view and perspective depiction of the rigid multi-core specimen biopsy device 200 depicted in FIG. 5 above.

FIG. 35 presents another side view and perspective depiction of the rigid multi-core specimen biopsy device 200 depicted in FIG. 5 above.

Figure 36:
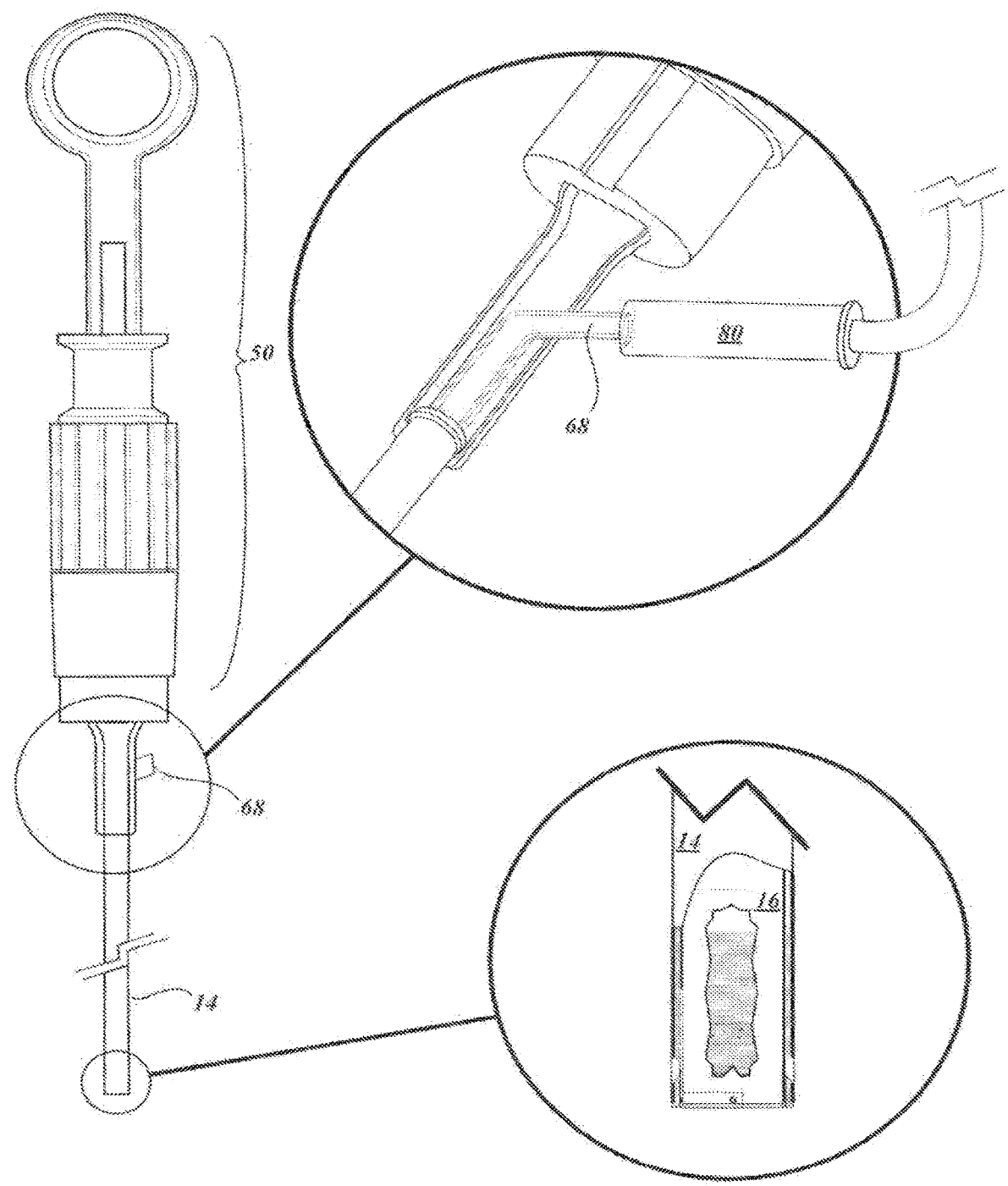
FIG. 36 schematically depicts side and cross-sectional views of another depiction of proximal specimen chamber 80 connectable with the multi-function handle 50 for specimen retrieval via aspiration from the distal chamber into the proximal chamber with preservation of sampling order and specimen orientation.

FIG. 36 schematically depicts side and cross-sectional views of another depiction of proximal specimen chamber 80 connectable with the multi-function handle 50 for specimen retrieval via aspiration or gentle suction directed to the biopsy access port 68 from the distal chamber 16 into the proximal chamber 80 with preservation of specimen sampling order and specimen orientation.

Figure 37:
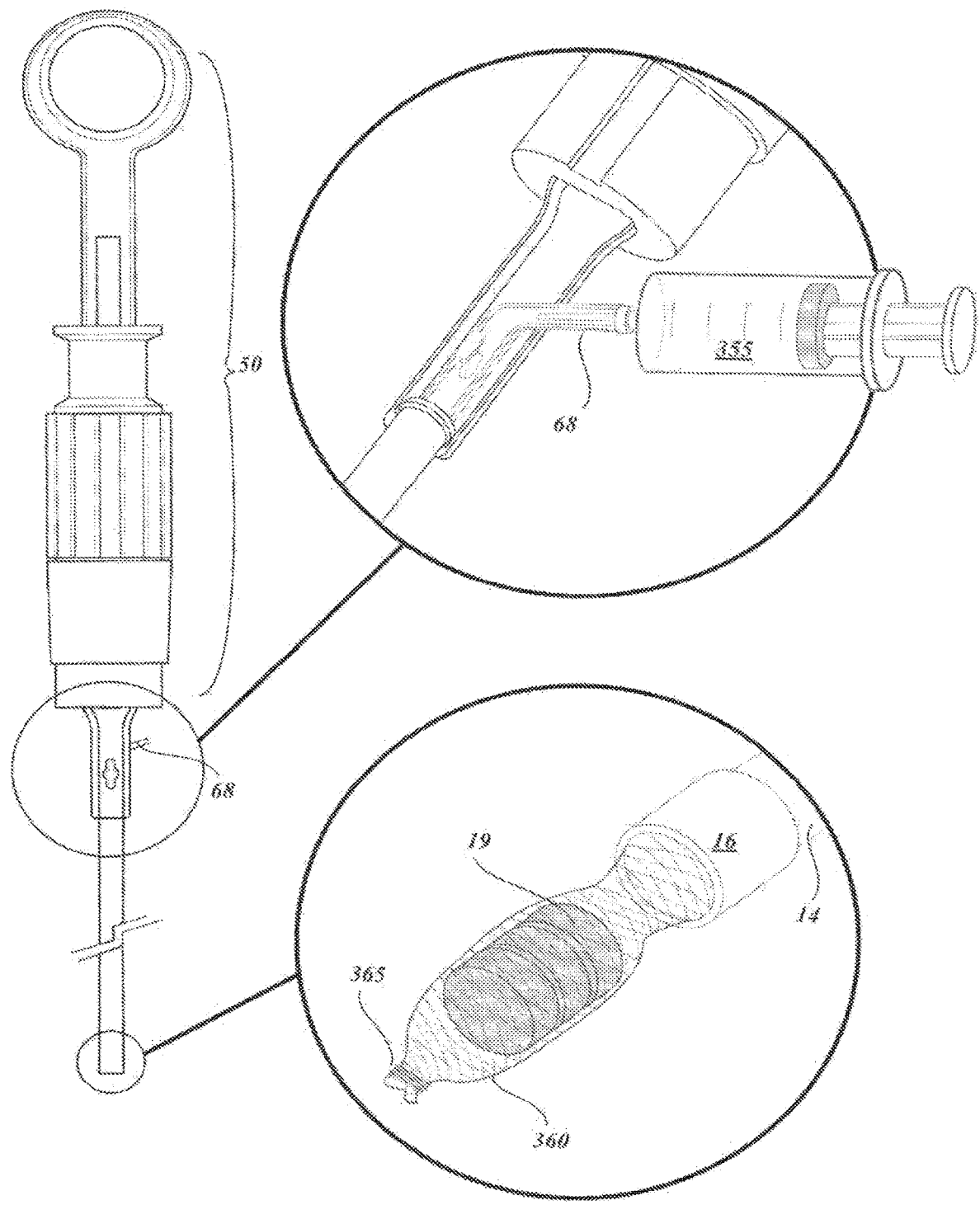
FIG. 37 schematically depicts side and cross-sectional views of retrieval of the multiple specimens from the distal chamber via fluid flushing from syringe 355 connected to the biopsy access port 68 into a net 360 with preservation of sampling order and specimen orientation.

FIG. 37 schematically depicts side and cross-sectional views of retrieval of the multiple tissue specimens 19 from the distal specimen chamber 16 via fluid flushing from syringe 355 connected to the biopsy access port 68. The flushed tissues are ejected from the distal specimen chamber 16 into a net 360 fitted with closure 365 with preservation of sampling order and specimen orientation.

The foregoing described above provides for embodiments of a MCB 10 and 100 devices and an SMS that quickly retrieves multiple anatomical tissue specimens for safe storage and management for histopathological assessment. The MCB and SMS intrinsic orientation saves a substantial amount of time for the pathologist and physician via sequential sampling of a single insertion event compared to single sampling of multiple insertion events.

Other embodiment of the MCB 10 or MCB 100 provide for complete aspiration of the multiple specimens into the proximal specimen management chamber attached to the proximal handle 50. This allows for unlimited number of biopsies taken in a single pass, in other words without removing the MCB from the endoscope.

Other embodiment of the MCB 10 or MCB 100 further provide for a stylet to be inserted into the center of the core biopsy to maintain rigidity as it is used to thrust into a submucosal tumor. Once positioned in direct view using an Endoscopic Ultrasound Scope the stylet is removed and a series of biopsies are taken as describe above.

While the preferred embodiment of the invention has been illustrated and described, as noted above, many changes can be made without departing from the spirit and scope of the invention. For example, other embodiments may include multiple ports for adaptable multiple flushing syringes having different fluids. Accordingly, the scope of the invention is not limited by the disclosure of the preferred embodiment. The design of taking multiple biopsies in this embodiment is applicable to any surgical and non-surgical endoscopy for any part of the body. It is not limited to only endoscopy but any surgical modality where tissue specimens are taken or used for tumors extraction. In fact this device can operate without the outer sheath and depth stops in certain surgical applications. Instead, the invention should be determined entirely by reference to the claims that follow.

What is claimed is:

1. A biopsy device, comprising:
a sheath equipped with a removable stylet, the sheath comprising a terminus with a distal chamber configured with a forward facing cutting edge comprising a plurality of movable blades, the plurality of movable blades including two counter rotating blades configured perpendicular or beveled relative to a long axis of the distal chamber, each counter rotating blade configured to pivot from a separate axis; and
a manipulation end controllable by a user to plunge the forward facing cutting edge at a sampling locus after removal of the removable stylet at a depth selected by the user and to engage a cutting action by the plurality of movable blades at the depth selected to acquire at least one specimen storable in the distal chamber.

2. The biopsy device of claim 1, wherein additional specimens are acquired at deeper depths at the sampling locus.

3. The biopsy device of claim 1, wherein the forward facing cutting edge includes a wire spanning across middle of the forward facing cutting edge.

4. The biopsy device of claim 3, wherein the forward facing cutting edge further includes a plate beneath the wire, and wherein the at least one specimen is cut along the long axis to form a plurality of specimen half pairs, the specimen half pair kept separated by the plate.

5. The biopsy device of claim 1, wherein at least one movable blade of the plurality of movable blades is initiated to pivot by a pulling action from the manipulation end.

6. The biopsy device of claim 1, wherein at least one movable blade of the plurality of movable blades is initiated to pivot by a pushing action from the manipulation end.

7. The biopsy device of claim 1, wherein a plurality of specimens is removed from the distal chamber by a flushing fluid conveyed from the manipulation end with preservation of specimen order and orientation.

8. An excisional device, comprising:
an outer sheath defining a diameter, a longitudinal axis, a proximal portion and a distal open portion; and
an inner assembly configured to be received within and, during operation of the excisional device, move parallel to the longitudinal axis of the outer sheath, the inner assembly defining a proximal portion, a distal portion and a body portion between the proximal and distal portions, the distal portion comprising at least one articulable curved blade whose actuation is independent of longitudinal movement of the inner assembly within the outer sheath, the articulable curved blade being configured to selectively open and close to provide a cored specimen by coring through and cutting parting-off the cored tissue, respectively.

9. The excisional device of claim 8, wherein the at least one articulable curved blade is configured to rotate and to sever the cored tissue from surrounding tissue by cutting through at least to the longitudinal axis of a central lumen of the outer sheath.

10. The excisional device of claim 8, wherein the inner assembly is configured to rotate within the outer sheath.

11. The excisional device of claim 8, wherein an outer edge of the at least one articulable blade is sharpened.

12. The excisional device of claim 8, wherein the at least one articulable curved blade comprises a surface having a substantially same curvature as a surface of the body portion.

13. The excisional device of claim 8, comprising at least two articulable curved blades configured to be selectively drawn closer to each other when a first force is applied to the distal portion and to be drawn away from each other when a second force is applied to the distal portion.

14. The excisional device of claim 13, further comprising respective tendons coupled to each of the at least two articulable curved blades, wherein the respective tendons are configured to selectively apply the first and second forces to the distal portion.

15. The excisional device of claim 8, wherein the at least one articulable curved blade is configured to selectively assume an open configuration to core through tissue and a closed configuration to sever the cored tissue from surrounding tissue and to advance the device through tissue.

16. A method, comprising:
providing a device comprising an outer sheath defining a diameter, a longitudinal axis, a proximal portion and a fixed distal open portion, an inner assembly configured to be received within the outer sheath, the inner assembly defining a proximal portion, a distal portion and a body portion between the proximal and distal portions, the distal portion comprising an articulable beak element configured to core through and cut tissue;

inserting the fixed distal open portion of the device into a body adjacent tissue to be sampled;

moving, during operation of the device, the inner assembly longitudinally within the outer sheath parallel to the longitudinal axis with the articulable beak element in a closed configuration relative to the fixed distal open portion;

opening the articulable beak element relative to the fixed distal open portion and coring through the tissue, and closing the articulable beak element to part-off the cored tissue, wherein opening and closing the articulable beak element is independent of longitudinal, movement of the inner assembly within the outer sheath.

17. The method of claim 16, further comprising transporting the parted-off cored tissue in a proximal direction within the inner assembly.

18. The method of claim 17, wherein drawing the tissue into the fixed distal scoop-shaped open portion comprises applying a vacuum.

19. An excisional device, comprising:

an outer sheath defining an inner and outer diameter, a longitudinal axis, a proximal portion and a distal open portion; and a tubular inner assembly configured to be received within and, during operation of the excisional device, move parallel to the longitudinal axis of the outer sheath, the inner assembly defining a proximal portion, a distal portion and a body portion between the proximal and distal portions, the distal portion being extendable beyond the outer sheath to be positioned adjacent tissue to be sampled, with the distal portion comprising a pair of articulable curved blades whose actuation is independent of longitudinal movement of the inner assembly within the outer sheath, the articulable curved blades being configured to selectively open apart and close together to provide a cored specimen by coring through and cutting parting-off the cored tissue, respectively;

wherein the articulable curved blades, when in the closed position within the outer sheath, are oriented adjacent to and follow the inner diameter of the outer sheath and have a sharp outwardly facing blade edge.

* * * * *